United States Patent [19]

Mollet et al.

[11] Patent Number: 5,786,184

[45] Date of Patent: Jul. 28, 1998

[54] LACTIC BACTERIA PRODUCING EXOPOLYSACCHARIDES

[75] Inventors: Beat Mollet, Mollie-Margot; Francesca Stingele, Lausanne, both of Switzerland

[73] Assignee: Nestec S.A., Vevey, Switzerland

[21] Appl. No.: 746,682

[22] Filed: Nov. 14, 1996

Related U.S. Application Data

[62] Division of Ser. No. 597,236, Feb. 6, 1996.

[30] Foreign Application Priority Data

Jun. 20, 1995 [EP] European Pat. Off. ............ 95201669

[51] Int. Cl.$^6$ ............................................. C12P 19/04
[52] U.S. Cl. .................... 435/101; 435/183; 435/193; 435/252.1; 435/252.3; 435/252.33; 435/252.5; 435/252.9; 435/320.1; 536/23.2; 536/23.7
[58] Field of Search ........................ 435/101, 193, 435/200, 69.1, 70.1, 183, 171, 252.3, 252.33, 252.1, 252.5, 252.9; 536/23.2, 23.7

[56] References Cited

FOREIGN PATENT DOCUMENTS

WO 88/00948  2/1988  WIPO.
WO 92/02142  2/1992  WIPO.

OTHER PUBLICATIONS

Rubens et al. Identification of cpsD, a gene essential for type III capsule expression in group B streptococci Mol. Microbiol. 8(5), 843–855, 1993.

Creighton, T. E. in "Proteins:Structure and Molecular Properties" Second Edition, W.H. Freeman and Company, New York, pp. 108, 109, 132 and 133, 1993.

Angelo Guidolin et al., "Nucleotide Sequence Analysis of Genes Essential for Capsular Polysaccharide Biosynthesis in *Streptococcus Pneumoniae* Type 19F", Infection and Immunity, vol. 62, No. 12, Dec. 1994, pp. 5384–5396.

Ernesto Garcis et al., "Cloning and Sequencing of a Gene involved in the Synthesis of the Capsular Polysaccharide of *Streptococcus Phenumoniae* Type 3" Molecular and General Genetics, vol. 239, No. 1–2, May 1993 Berlin de, pp 188–195.

Marisa Vescovo et al., "Plasmid–Encoded Ropiness Production in Lactobacillus Casei SSP. Casei" Biotechnology Letter, vol. 11 No. 10, Oct. 1989, pp. 709–712.

Thierry Doco et al., "Structure of an Exocellular Polysaccharide Produced by *Streptococucu Thermophilus*", Carbohydrate Research, vol. 198, No. 2, May 1, 1990 Amsterdam NL, pp. 313–321.

*Primary Examiner*—Robert A. Wax
*Assistant Examiner*—Nashaat T. Nashed
*Attorney, Agent, or Firm*—Pennie & Edmonds LLP

[57] ABSTRACT

DNA fragment of genomic origin coding for at least one enzyme involved in the biosynthesis of an EPS, and capable, following the transformation of a lactic bacteria, of restoring the production of an EPS in the said bacterium not initially producing any EPS, or of modifying the structure of the EPS initially produced by the said bacterium. Proteins of the *Streptococcus thermophilus* strain CNCM I-1590 encoded by the chromosome and which are involved in the biosynthesis of the EPS having the composition Glc:Gal:GalNac= 1:2:1. Method for the manufacture of a new EPS, in which a DNA fragment coding partially or totally for at least one enzyme involved in the biosynthesis of an EPS is cloned into a vector, lactic bacteria producing another EPS are transformed with the recombinant vector, and a lactic bacterium producing a new EPS is then selected.

21 Claims, 2 Drawing Sheets

LACTIC BACTERIA PRODUCING EXOPOLYSACCHARIDES

This is a division of application Ser. No. 08/597,236, filed Feb. 6, 1996.

TECHNICAL FIELD

The present invention relates to the use of chromosomal DNA fragments of lactic bacteria coding for at least one enzyme involved in the biosynthesis of exopolysaccharides, as well as to enzymes encoded by these fragments.

Prior art

Lactic bacteria are known to be capable of producing two classes of polysaccharides in their culture medium, namely homopolysaccharides such as dextrans or levans which consist of the repeated assembly of a single sugar, and heteropolysaccharides commonly called exopolysaccharides or EPSs (EPS is short for the term "exopolysaccharide") consisting of the assembly of several different sugars forming a repeating unit (Cerning J., Bactéeries lactiques, [Lactic bacteria], Vol I, by Rossart H and Luquet F. M., Lorica, 309–329, 1994).

A lactic bacterium producing an EPS can impart a ropy character and/or a smooth and creamy texture to an acidified milk (Cerning et al., FEMS Microbiol., 87, 113–130, 19/90). EPSs can also display biological activities which are especially advantageous for human or animal health, such as antitumour or probiotic activities, for example (Oda M. et al., Agric. Biol. Chem., 47, 1623–1625, 1983; EP94870139.6).

Moreover, the industry is confronted by a genetic instability of the biosynthesis of EPSs in lactic bacteria. This generally manifests itself during a fermentation by the loss of EPS production by all or part of the lactic bacteria (see "Cerning J." above). Industrial fermented products are thus subject to variations in their EPS content, which is not always acceptable. To remedy these problems, the industry resorts at the present time to the isolation and periodic characterization of its bacteria so as to separate the ones which have lost their original character.

EPS biosynthesis in mesophilic lactic bacteria, that is to say lactic bacteria having optimal growth at 28°–37° C., involves at least one enzyme which effects the linking of the sugars. No chromosomal or plasmid gene of mesophilic lactic bacteria coding for such an enzyme has yet been identified and sequenced, although plasmids involved in EPS biosynthesis are known.

Thus, WO 92/02142 discloses the existence of the plasmid pHV67 which produces in *Lactococcus lactis* subsp. *lactis* (mesophile) a substance capable of increasing the viscosity of a fermented milk. U.S. Pat. No. 5,066,588 describes two plasmids originating from a strain of *Streptococcus cremoris* (mesophile) capable of imparting a thickening character on a *Streptococcus lactis*. Similarly, Vescovo et al. have demonstrated a plasmid from a *Lactobacillus casei* subsp. *casei* strain (mesophile) coding for a Muc+ phenotype, that is to say for functions linked to the production of exocellular thickeners (Vescovo et al., Biotechnology Letters, Vol II, 709–712, 1989).

Lastly, Van den Berg et al., are seeking to isolate from a *Lactobacillus sake* (mesophile) a group of chromosomal genes involved in the biosynthesis of an EPS (Van den Berg D. J. C. et al., First International Conference on Polysaccharide Engineering, Trondheim, Norway, Jun. 6–8, 1994). However, no gene has yet been identified and/or sequenced.

Furthermore, EPS biosynthesis in thermophilic lactic bacteria, that is to say lactic bacteria having optimal growth at 37°–45° C., is not yet well known. It is known, however, not to be associated with a plasmid. Thus, Vescovo et al. showed that the Muc+ phenotype of *Lactobacillus delbrueckii* subsp. *Bulgaricus* strain 2o1 (thermophile) is linked to chromosomal functions (Vescoso et al., Biotechnology Letters, Vol II, 709–712, 1989).

Thus, to date, no chromosomal or plasmid gene or group of genes coding for an EPS of mesophilic or thermophilic lactic bacteria has been identified and/or sequenced.

Hence it would be very advantageous to have means for restoring or stabilizing the original EPS production in lactic bacteria. Furthermore, it would also be advantageous to have means for modifying the structure of an EPS, and thereby creating new EPSs capable of having advantageous properties.

SUMMARY OF THE INVENTION

The objective of the invention is to provide new means for controlling, modifying and/or restoring EPS synthesis in vivo and in vitro.

To this end, the present invention relates to any lactic bacterial DNA of chromosomal origin coding for at least one enzyme involved in the biosynthesis of the EPS possessing the repeat structure

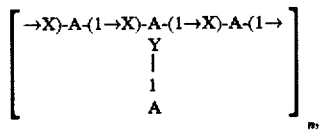

where n>1; A is chosen from the group composed of β-D-Galp, β-D-Glcp and their acetyl and phosphatyl derivatives; and x and y=2, 3, 4, 5 or 6, given that x≠y.

Another subject of the present invention relates to recombinant vectors comprising a DNA fragment according to the present invention.

Another subject of the present invention relates to a protein capable of being involved in the biosynthesis of the EPS having the repeat structure

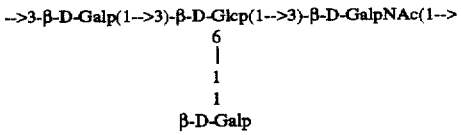

the said protein having the amino acid sequence chosen from the group composed of the sequences SEQ ID NO: 2, 3, 4, 5, 6, 7, 8, 9, 10, 11, 12, 13, 14 and the homologous sequences (sequences presented in the sequence listing below).

Another subject of the present invention relates to a lactic bacterium comprising, integrated in its chromosome or with the aid of a replicable plasmid, a DNA fragment according to the invention.

Another subject of the present invention relates to a method for the production of an EPS, in which (1) a DNA fragment coding for the enzymes according to the invention is cloned into a vector, the said vector comprising, in addition, a sequence permitting autonomous replication in a host cell or integration into the latter, (2) a host cell is transformed with the said vector, and (3) the transformed host cell is then cultured under suitable conditions for the production of an EPS.

The invention also relates to another method for the production of a new EPS, in which (1) a DNA fragment coding for at least one enzyme involved in the biosynthesis of an EPS is cloned into a vector, (2) a lactic bacterium is transformed with the said vector, and (3) the transformed lactic bacterium is then cultured under suitable conditions for the production of a new EPS.

Hence the present invention opens up the possibility of using DNA fragments according to the invention to restore or modify EPS production in a lactic bacterium. Thus it is possible to envisage expressing or overexpressing the DNAs according to the invention in a lactic bacterium, to produce EPSs intended for thickening, and making creamy, drinks or food such as liquid desserts, yoghurts, soups, dairy icecreams, coffee creams, sauces or mayonnaises, for example.

The present invention also makes it possible to have new means for identifying chromosomal genes of lactic bacteria involved in EPS biosynthesis.

Lastly, the present invention also provides new enzymes involved in the biosynthesis of the EPS which is described above. These enzymes may thus be advantageously used to synthesize or modify in vitro a polysaccharide such as an oligosaccharide or an EPS, for example (Ichikawa Y. et al., American Chemical Society, 114, 9283–9289, 1992).

BRIEF DESCRIPTION OF THE DRAWING FIGURES

FIG. 1.A. is a physical map of the operon involved in the synthesis of the EPS of the *S. thermophilus* strain CNCM I-1590. The promoters and terminators are represented, respectively, by flags and hairpins. The vertical arrow indicates the position of the insertion site of the transposon Tn916. The horizontal arrows indicate the presence of potential open reading frames (ORFs). The names of the genes corresponding to the ORFs appear below the arrows. The restriction enzymes are shown in abbreviated form (S=SacI; H=HindIII; E=EcoRI; B=BamHI).

FIG. 1.B. is a representation of the chromosomal inserts of the strain CNCM I-1590, present in the 11 pFS vectors. P1, P2 and P3 indicate the position of the probes which are used during screening.

FIG. 1.C. is a representation of the genomic insert pFS101 comprising the whole of the eps operon from the SacI restriction site to BamHI, which is cloned into pJIM2279.

FIG. 2. is a representation of the optical density at 485 nm of the gel filtration chromatography fractions comprising the sugars produced by *Lactococcus lactis* strain MG1363 transformed with pFS101 or pJIM2279. Fraction 9: $2 \times 10^6$ daltons (Da); fractions 11–13: $5 \times 10^5$ Da; fractions 14–16: $7.2 \times 10^4$ Da; fractions 17–18: $4 \times 10^4$ Da; fraction 19 and above: $<5 \times 10^3$ Da.

DETAILED DESCRIPTION OF THE INVENTION

Figures 1A, 1B, 1C:
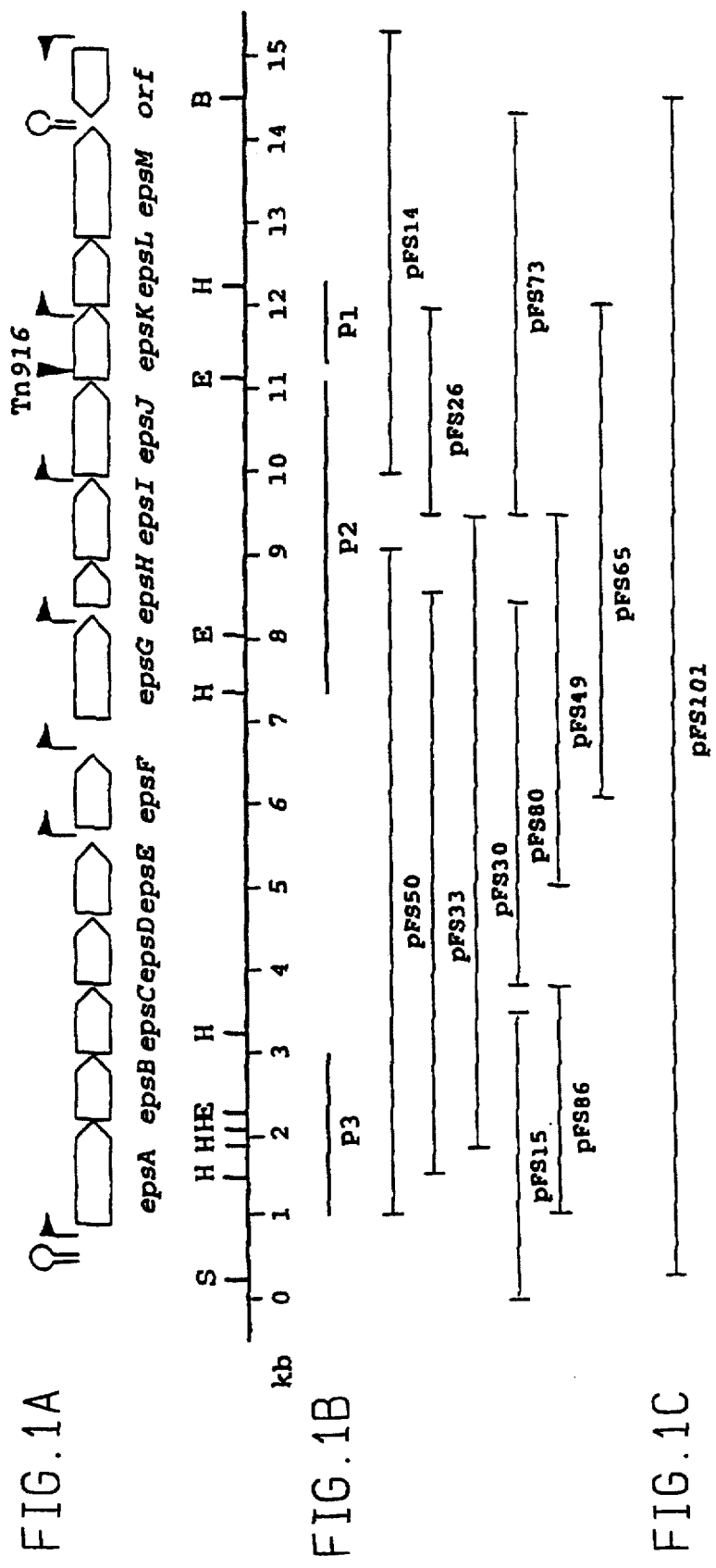

In the description which follows, the term "EPS" denotes an exopolysaccharide produced by a lactic bacterium which consists of the assembly of several different sugars forming a repeating unit.

The terms acetyl and phosphatyl derivatives are used to denote galactose or glucose comprising at least one acetyl and phosphatyl radical at positions $C_2$ to $C_6$ on the sugar ring.

For the purposes of the present invention, "homologous sequence" is understood to mean any nucleic acid or amino acid sequence having an identical function, differing from the sequences according to the invention only in the substitution, deletion or addition of a small number of nucleic acid or amino acid bases, for example 1 to 500 base pairs (bp) or 1 to 150 amino acids.

In this context, two DNA sequences which, as a result of the degeneracy of the genetic code, code for the same polypeptide will be considered, in particular, to be homologous. Similarly, two functional proteins which are recognized by the same antibody, the ratio of the values for intensity of recognition of the two proteins by the antibody not exceeding 1000, and preferably 100, for example, will be considered to be homologous.

A sequence will also be considered to be homologous if it displays more than 70% homology with the sequences according to the invention, especially more than 80% or 90%. In the latter case, the homology is determined by the ratio of the number of bases or of amino acids of a homologous sequence which are identical to those of a sequence according to the invention, to the total number of bases or of amino acids of the said sequence according to the invention.

For the purposes of the present invention, "fragment which hybridizes" is understood to mean any fragment capable of hybridizing with the fragments according to the invention by the Southern blotting method (Sambrook et al., Molecular Cloning, A Laboratory Manual, Cold Spring Harbor Laboratory Press, U.S.A., 1989., chapters 9.31 to 9.58). Preferably, the hybridization is conducted under stringent conditions so as to avoid nonspecific or unstable hybridizations.

Lastly, the term "fragment" or "DNA fragment" should be understood to be a double-stranded DNA of chromosomal origin, which may be synthesized, reproduced in vitro, for example, by the known method called the "polymerase chain reaction", or reproduced in vivo in a bacterium of the *Escherchia coli*, *Lactococcus lactis* or *Streptococcus thermophilus* type, for example.

To select a DNA fragment according to the present invention, it is possible to build a library of large DNA fragments from a lactic bacterium producing an EPS in a lactic bacterium not producing any EPS, and then to select the clone or clones producing an EPS. To this end, the genomic DNA of a lactic bacterium producing an EPS is digested with a restriction enzyme which is specific for a relatively rare restriction site (BamHI, SalI, PstI) or by a partial digestion with Sau3A, for example. The digestion product is cloned into an expression or integration plasmid which accepts large fragments (plasmid pSA3 described in Example II), the recombinant plasmids are introduced into the same species of lactic bacterium not producing any EPS, at least one transformed clone producing an EPS is selected and the DNA fragment responsible for EPS production is then identified, isolated and sequenced in a traditional manner.

In view of the fact that the DNA fragments according to the present invention are capable of being large-sized, since they can contain a group of genes involved in EPS biosynthesis, it may be preferable to introduce the recombinant plasmids into the same strain of lactic bacterium from which the fragments originate, apart from the fact that this strain has lost the capacity to produce EPSs following a mutagenic treatment (UV or chemical treatment or treatment with a transposon).

An alternative to the method described above can also consist in building a plasmid library of DNA fragments from a strain of lactic bacterium producing an EPS, in transforming the same strain of lactic bacterium with the plasmids incapable of replicating therein, in selecting the transformants which have integrated a plasmid into their genome by homologous recombination (selection by a resistance to an antibiotic, for example), in selecting the transformants no longer producing any EPS and then in isolating and sequencing the chromosomal DNA fragments of the selected transformants which are adjacent to the integrated plasmid. To this end, it is possible to digest the chromosome of the transformants, to ligate it and then to perform a reverse PCR using probes specific for the integrated plasmid or to introduce the ligation product into a strain in which the recircularized plasmid is capable of replicating, for example.

Another alternative to the selection method described above can also consist in transforming lactic bacteria producing an EPS with a plasmid comprising a transposon, in subjecting the bacteria to conditions under which the transposon is excised from the vector and integrates at random into the genome, in selecting the clones of bacteria which have lost the capacity to produce EPSs, and in isolating the genomic DNA fragments from the said clones into which a transposon has integrated. This method is described in greater detail in Example I presented below.

It should be pointed out that the selection methods described briefly above may be applied to all known lactic bacteria, in particular to mesophilic lactic bacteria such as, for example, *Streptococcus cremoris*, *Streptococcus lactis*, *Lactobacillus casei* subsp. *casei* and *Lactobacillus sake*, and thermophilic lactic bacteria such as, for example, *Streptococcus thermophilus*, *Lactobacillus delbruecki* subsp. *bulgaricus* and *Lactobacillus helveticus*. To this end, a person skilled in the art has transformation techniques at his disposal for each species of lactic bacterium, and especially for *Lactobacillus delbruecki* subsp. *bulgaricus* (Sasaki Y. et al., FEMS Microbiology Reviews, 12, Fourth Symposium on Lactic Acid Bacteria, Noodwijkerhout, The Netherlands, Sept. 1993).

Furthermore, the selection methods described above make it possible, more often than not, to isolate only a portion of a gene or of a group of genes involved in the biosynthesis of an EPS. Nevertheless, a person skilled in the art may readily identify the remaining portion of the gene or group of genes by selecting in a chromosomal library, using nucleic acid probes based on an isolated fragment, one or more clones containing the remaining portion, for example (see Example I.6).

It was thus possible to characterize a DNA sequence of 15.2 kb of the *Streptococcus thermophilus* strain deposited on 7th Jun. 1995 with the Collection Nationale de Culture de Microorganisme (C.N.C.M.) [National Collection of Microorganism Cultures] (CNCM), Pasteur Institute, 28 rue du Dr Roux, 75724 Paris cedex 15, France, where it received the deposit No. CNCM I-1590. Moreover, this Gram-positive strain in displays under the microscope an appearance of non-flagellated cocci forming small chains. This strain does not make spores and is a facultative anaerobe.

This sequence of 15.2 kb comprises genes coding for new enzymes involved in the biosynthesis of an EPS having the repeat structure

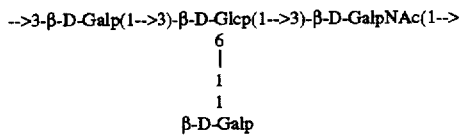

Nucleotides 648 to 15250 of this sequence of 15.2 kb are shown in the sequence SEQ ID NO: 1 given in the sequence listing below. 13 complete genes are delimited in the nucleic acid sequence SEQ ID NO:1 by nucleotides 352–1803, 1807–2535, 2547–3239, 3249–3995, 4051–4731, 4898–5854, 6425–7540, 7736–8212, 8221–9192, 9285–10364, 10392–11339, 11302–12222 and 12233–13651.

It was possible to show that all or part of the sequence SEQ ID NO: 1 makes it possible, following a transformation, to restore an EPS biosynthesis in a host cell such as a mesophilic or thermophilic lactic bacterium which was initially not producing any EPS, in particular in a Streptococcus or a Lactococcus. As an example, the DNA sequence according to the invention may thus be used to restore EPS production in a mutant of the *S. thermophilus* strain CNCM I-1590 no longer producing any EPS (natural mutant or one originating from a mutagenesis.

To restore the biosynthesis of an EPS, all or part of the sequence SEQ ID NO:1 comprising at least one of the abovementioned genes may be integrated into a host cell by means of the method described in EP 564,966, the said method being incorporated by reference in the teaching of the present invention. Briefly, this method makes it possible to be able (1) to transform the host cell with a donor plasmid which does not replicate therein, the said plasmid comprising the said fragment functionally integrated (the reading frame is preserved) into a portion of an operon originating from the host cell; (2) to identify the transformants comprising the whole of the plasmid, integrated; (3) to select transformants comprising only, integrated into the chromosome, the fragment according to the invention, the other sequences of the plasmid having been excised from the chromosome; and (4) to culture the selected transformants under suitable conditions for the production of an EPS.

It may be noted that this method makes it possible not to use functional promoter and translation activator sequences. Furthermore, the culture conditions suitable for EPS production are within the capacity of a person skilled in the art, who can use standard culture media and choose the pH, temperature and agitation of the optimum medium according to the strain used.

It is also possible to choose to clone all or part of the sequence SEQ ID NO:1 comprising at least one of the abovementioned genes into a self-replicating expression plasmid downstream of functional promoter and translation activator sequences and, where appropriate, upstream of a terminator, and then to transform a host cell with the recombinant plasmid.

Moreover, it may be observed that the EPS produced by a host cell transformed with the sequence SEQ ID NO:1, for example a *Lactococcus lactis* not initially producing an EPS, may be different from the EPS which should normally be synthesized by the recombinant enzymes, in this instance the EPS produced by the strain CNCM I-1590. The use of all or part of the sequence of 15.2 kb can hence permit the creation of variants of the EPS described above.

Similarly, it could be shown that all or part of the sequence SEQ ID NO:1 can also make it possible, following a transformation, to modify the repeat structure of an EPS initially produced by a host cell, for example by a mesophilic or thermophilic lactic bacterium, in particular a Streptococcus or a Lactococcus.

These observations thus open up the possibility of producing a novel method of production of a new EPS, in which (1) a DNA fragment coding partially or totally for at least one enzyme involved in the biosynthesis of an EPS is cloned into a vector; (2) lactic bacteria are transformed with the recombinant vector; (3) where appropriate, a lactic bacterium producing a new EPS is selected; and (4) the transformed lactic bacterium is then cultured under suitable conditions for the production of a new EPS. Preferably, the vector codes for the proteins according to the invention. Furthermore, the lactic bacterium can produce an EPS other than the one synthesized by the proteins encoded by the said vector.

In particular, a DNA fragment coding partially for at least one enzyme involved in the biosynthesis of a first EPS is cloned into an integration vector, the recombinant vector is introduced into mesophilic or thermophilic lactic bacteria capable, where appropriate, of producing a second EPS via one or more chromosomal or plasmid genes, the bacteria which have integrated the integration vector into their chromosome are isolated, and those which produce a new EPS are then selected on account of the inactivation of one or more genes involved in the biosynthesis of the second EPS. Preferably, the first and the second EPS are identical, and a DNA fragment coding partially (at least 15 base pairs) for at least one enzyme involved in the addition of a sugar to the side chain of the repeating unit or in the modification of a sugar, such as a sulpho-, phospho- or acetyltransferase, for example, is chosen.

Similarly, a DNA fragment coding totally for at least one enzyme involved in the biosynthesis of a first EPS may be cloned into a replicative expression vector, the recombinant vector may be introduced into mesophilic or thermophilic lactic bacteria capable, where appropriate, of producing a second EPS via one or more chromosomal or plasmid genes, the bacteria containing the replicative vector may be isolated, and those which produce a new EPS may then be selected on account of the expression of one or more genes involved in the biosynthesis of the first EPS. Preferably, DNA fragments coding for enzymes involved in the modification of a sugar, such as a sulpho-, phospho- or acetyltransferase, for example, or in the addition of the repeating unit of a sugar such as a glucosyl- or a galactosyltransferase, for example, are chosen.

Preferably, at least one of genes carried by the sequence SEQ ID NO:1 is used totally or partially. At least one plasmid gene of mesophilic lactic bacteria involved in the biosynthesis of an EPS (gene which may be sequenced from known plasmids) may also be used.

Lastly, the recombinant vector can be any linear or circular, single- or double-stranded expression or integration DNA fragment comprising a DNA sequence according to the invention, in particular all or part of the sequence SEQ ID NO: 1. In the event of the method described in EP 564,966 not being used, care should be taken that the vector can express the DNA according to the invention through appropriate nucleic acid sequences (promoter; ribosome binding site; preferred codon) and, where appropriate, that it comprises one or more origins of replication from various bacteria, in particular from *Escherichia coli* and/or from a Streptococcus, for example.

The invention also relates to new enzymes encoded by the genes of the sequence SEQ ID NO:1, in particular the sequences which are homologous with them. Their use to modify or synthesize in vitro an oligosaccharide or a polysaccharide such as an EPS, for example, may thus be envisaged. For this purpose, it is preferable to purify at least one of these enzymes, by overexpressing their gene in a traditional manner in a bacterium and isolating them in a traditional manner, by precipitation and/or chromatography of the cultural medium, for example.

Another subject of the present invention relates to a lactic bacterium comprising, integrated in its chromosome or with the aid of a replicable plasmid, a DNA sequence according to the invention. Preferably, the sequence comprises at least one of the genes of the sequence SEQ ID NO:1.

The invention also relates to any use of fragments of the sequence SEQ ID NO:1, or of fragments of the strand complementary to this sequence, of at least 15 base pairs, as primer for carrying out a PCR or as probe for detecting in vitro or inactivating in vivo genes of lactic bacteria involved in the biosynthesis of an EPS. This lower limit is set arbitrarily on account of the fact that small fragments which hybridize specifically are generally 15–25 bp in length.

EXAMPLES

The present invention is described in greater detail below by means of the additional description which follows, which relates to examples of obtaining DNA fragments, recombinant plasmids and transformed bacteria according to the invention. These examples are preceded by a description of the culture media. It is self-evident, however, that these examples are given by way of illustration of the subject-matter of the invention, of which they in no way constitute a limitation. DNA manipulation and the cloning and transformation of bacterial cells are, unless otherwise specified, performed according to the protocols described in the work by Sambrook et al. cited above. Percentages are given by weight except where otherwise stated.

Media: (add 1.5% of bacto-agar for a solid medium)
- M17 (Difco, U.S.A.): tryptone 0.5%, soytone 0.5%, hydrolysed meat 0.5%, yeast extract 0.25%, ascorbic acid 0.05%, magnesium sulphate 0.025%, disodium beta-glycerophosphate 1.9% and water.
- LM17: M17 medium comprising 1% of lactose.
- GM17: M17 medium comprising 1% of glucose.
- MSK: skimmed milk (10% reconstituted powder) comprising 0.1% of yeast extract.
- MAM: skimmed milk (10% reconstituted powder) comprising 10% of a mixture of amino acids (495 mg/l Ala, 343 mg/l Arg, 682 mg/l Asp, 59 mg/l Cys, 1229 mg/l Glu, 759 mg/l Gly, 153 mg/l His, 215 mg/l Iso, 470 mg/l Leu, 565 mg/l Lys, 122 mg/l Met, 255 mg/l Phe, 436 mg/l Pro, 68 mg/l Ser, 170 mg/l Thr, 61 mg/l Try, 304 mg/l Val adjusted to pH 5).
- HJL: tryptone 3%, beef extract 0.2%, yeast extract 1%, lactose 1% and $KH_2PO_4$ pH 6.5 0.5%.
- Ruthenium red: 0.5% yeast extract, skimmed milk powder 10%, sucrose 1%, agar 1.5% and 0.08 g/l of ruthenium red (see FR2,632,968).

Example I: cloning of a DNA fragment of *S thermophilus* strain Sfi6

I.1. Selection of an *S. thermophilus* strain producing EPS: the strains of lactic bacteria from the Nestlé collection are cultured in HJL liquid medium, and dilutions thereof are plated out on ruthenium red solid medium. Strains producing EPS remain white since the EPSs prevent the dye from staining their cell wall. In contrast, non-producing strains stain red on account of the affinity of the dye for the peptidoglycan of their cell wall.

In this way, *S. thermophilus* strain Sfi6, which received the deposit number CNCM I-1590 and which will be designated in the examples which follow by the expression "strain Sfi6", was selected from the lactic bacteria producing EPS.

I.2. Repeat structure of the EPS: the structure of the EPS produced by the strain Sfi6 has been published by Doco et al. (Carbohyd. Res., 198, 313–321, 1995). This EPS possesses the composition Glc:Gal:GalNac=1:2:1, and the tetrasaccharide repeat unit:

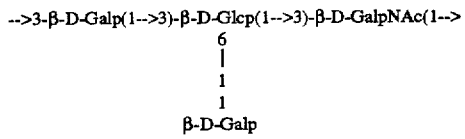

I.3. Mutagenesis with the transposon Tn916: the strain Sfi6 is rendered resistant to streptomycin by culturing it by repeated transfers in HJL medium supplemented with contents increasing from 20 to 2000 µg/ml of streptomycin, and by then selecting the strains which become naturally resistant.

The streptomycin-resistant strain Sfi6 and *Enterococcus faecalis* strain JH2-2, which possesses a plasmid pAM180 carrying the transposon Tn916 (Tn916 is known to carry a tetracycline resistant gene; Gawron et al., Nature, 300, 281–283, 1982) are conjugated. For this purpose, 1 ml of an overnight culture in M17 medium at 37° C. of *E. faecalis* strain JH2-2 is mixed with 10 ml of an overnight culture in HJL medium at 42° C. of the strain Sfi6, the cells are centrifuged and resuspended in tubes comprising 100 µl of HJL medium, the suspension is applied to LM17 solid medium which is incubated at 37° C. for 20 h, the cells are recovered by scraping and resuspended in tubes of 10 ml of HJL liquid medium, the tubes are incubated at 42° C. for 4 h, shaking them from time to time, and dilutions of the cultures are then plated out on solid LM17 medium supplemented with 2.5 µg/ml of tetracycline and 2000 µg/ml of streptomycin.

By carrying out 20 conjugations in parallel (independent mutations), it was possible in this way to select $2 \times 10^4$ tetracycline- and streptomycin-resistant transconjugents.

I.4. Selection of mutants of the strain Sfi6 no longer producing EPS [EPS(−)phenotype]: the resistant transconjugants are transferred onto ruthenium red solid medium supplemented with 2.5 µg/ml of tetracycline and 2000 µg/ml of streptomycin. Approximately 10% of the transconjugents form EPS(−) red colonies. Approximately 800 red colonies are then selected and cultured overnight in microtitration plates comprising 200 µl of HJL medium supplemented with 2.5 µg/ml of tetracycline. 100 µl of the HJL culture are then cultured in 1 ml of MSK milk. Approximately 25% of the red colonies tested display a stable EPS(−) phenotype in the milk (the milk is not thick and ropy, and analysis of the culture supernatant does not disclose any EPS). The other red colonies display an EPS(+) phenotype or recover the EPS(+) phenotype after several subcultures in the milk.

In conclusion, the EPS(−) stable mutants have lost their capacity to produce EPSs as a result of the integration of the transposon Tn916 into a chromosomal gene involved in the biosynthesis of EPSs. In effect, the EPS(−) stable mutants can recover an EPS(+) phenotype when they are cultured in a growth medium lacking tetracycline (excision and loss of the transposon).

I.5 Characterization of EPS(−) stable mutants: approximately 100 stable mutants are analysed by the Southern blotting of a chromosomal DNA preparation from the mutants, digested with HindIII, and hybridization of the Southern blot filter with the radioactive tetM gene (encodes a tetracycline resistance) originating from the plasmid pIC182 (Hill et al., Applied and Env. Micro., 54, 1230–1236, 1988). Approximately 85% of the mutants analysed display an identical preponderant band corresponding to a locus called "locus A". For some of the other mutants, two further preponderant bands (locus B and C), corresponding to known loci involved in the biosynthesis of the cell wall (publication in preparation), may be noted.

I.6 Characterization of the locus A: the chromosomal regions close to the integrated transposon Tn916 may be isolated by reverse PCR. For this purpose, 1 µg of a chromosomal DNA preparation from an arbitrarily chosen mutant (mutant No.1) is digested in a traditional manner with HindIII for 4h, the DNA is extracted with phenol/chloroform and diluted in 720 µl of water, the diluted DNA is heated to 56° C. for 5 minutes, the DNA is cooled on ice, 80 µl of a 10-fold concentrated ligation buffer and 5 units of a T4 ligase (Boehringer-Mannheim) are added to it, and it is incubated at 12° C. for 16 h, heated to 70° C. for 15 min to inactivate the ligase and then concentrated in a volume of 100 µl by several successive extractions in butanol. 10 µl of the ligation mixture, 100 pmol of primers, 15 mM dNTPs, 10 µl of buffer and 0.2 unit of Super-Taq polymerase (Stehlin GmbH) are then added into a PCR device. The nucleic acid primers are chosen on the basis of the known sequence of the transposon Tn916.

Using the primers having the sequence SEQ ID NO:15 and SEQ ID NO:16, a 1-kb fragment could be isolated by PCR. Furthermore, using the primers SEQ ID NO:17 and SEQ ID NO:18, a 4-kb fragment could be isolated (see the sequence listing below).

A third, 0.8-kb fragment may also be isolated from the mutant No.1, by carrying out a second reverse PCR from its chromosomal DNA digested with RsaI and using the primers having the sequences SEQ ID NO:18 and SEQ ID NO:19 (see the sequence listing below).

The 1-kb and 0.8-kb fragments were cloned into the linearized plasmid pGEMT (Promega, U.S.A.). Sequencing of these fragments by the dideoxynucleotide method (f-mol® DNA Sequencing System kit, Promega) shows two sequences which, on being matched up, cover three open reading frames (ORFs) corresponding to nucleotides 9933 to 11643 of the sequence SEQ ID NO:1.

The 1-kb and 4-kb fragments were also used to screen a λ-ZAP Express (Stratagene, U.S.A.) library containing DNA fragments of the strain Sfi6. For this purpose, according to the supplier's recommendations, a DNA preparation from the said mutant is partially digested with Sau3A, the fragments are separated by agarose gel electrophoresis, the bands corresponding to 5- to 12-kb fragments are cut from the gel, and the DNA is eluted and then ligated to the λ-ZAP Express vector previously digested with BamHI. The ligation product is encapsidated in vitro using the GigagoldIII system (Stratagene), the phages are then mixed with *Escherichia coli* XL1Blue (Stratagene) according to the supplier's recommendations and the mixture is then plated out on a Petri dish. The recombinant plagues are then analysed by hybridization of their DNA, transferred onto a Hybond N membrane (Amersham Life Sciences, UK), with the 1-kb and 4-kb fragments previously rendered radioactive (Random Primed DNA Labelling kit, Boehringer-Mannheim).

From 3000 recombinant plaques, approximately 20 positive plaques could be selected by hybridization, from which the λ-ZAP Express vectors were then isolated, and the pCMV vectors containing a chromosomal insert were thereafter excised (see the recommendations of the supplier Stratagene). These recombinant vectors are called "pFS" in the examples which follow.

The chromosomal inserts of 11 pFS vectors were then sequenced (f-mol® DNA Sequencing System kit), these being the vectors pFS14, pFS15, pFS26, pFS30, pFS33, pFS49, pFS50, pFS65, pFS73, pFS80 and pFS86 (see FIG. 1.B) which comprise, respectively, fragments corresponding to the nucleotides of the sequence SEQ ID NO:1, 9314–14602, 1–3159, 7988–11253, 1702–7991, 1361–7229, 4400–8477, 648–7676, 5997–11253, 8474–13489, 3550–7229 and 648–1702.

By matching up the nucleic acid sequences of the different chromosomal inserts, it was possible in this way to characterize a sequence of 15.2 kb corresponding to the locus A of the strain Sfi6 (see FIG. 1.A). Nucleotides 648 to 15250 of this sequence of 15.2 kb are shown in the sequence SEQ ID NO:1.

I.7. Analysis of the sequence SEQ ID NO:1:

The sequence SEQ ID NO:1 comprises the whole of the eps operon of the strain Sfi6. This sequence comprises 13 complete ORFs in the same orientation, which are called eps A, B, C, D, E, F, G, H, I, J, K, L and M, (see FIG. 1.A). This sequence comprises, in addition, one complete ORF at the 3' end of the sequence, which is encoded by the complementary strand. This ORF, called orfZ, probably marks the end of the operon on account of its reverse orientation relative to the other ORFs.

Comparison of the amino acid sequences encoded by the first 13 ORFs with those of the proteins present in the Swiss-Prot data bank, using the softwares FASTA, PEPPLOT and PILEUP from GCG-software, Wis., U.S.A., enables the function of the 13 proteins encoded by the eps operon to be deduced. The results are presented below.

The epsA ORF (nucleotides 352–1803) codes for an EpsA protein (SEQ ID NO:2) having 26.4% identity with the LytR protein of *Bacillus subtilis* which is involved in the regulation of the autolysin N-acetylmuramoyl-L-alanine (Lazaveric et al., J. Gen. Microbiol., 138, 1949–1961, 1992). Hence EpsA is probably a regulator protein for the eps operon. Moreover, since a regulator ORF of an operon is generally found upstream of the other ORFs, the epsA gene is probably the first gene of the eps operon. This is confirmed by the fact that a terminator is found at nucleotides 230–252, a promoter at nucleotides 274–302 and a ribosome binding site at nucleotides 340–345 of the sequence SEQ ID NO:1.

The epsB gene (nucleotides 1807–2535) codes for an EpsB protein (SEQ ID NO:3) having 67.5% identity with the CpsA protein of *Streptococcus agalactiae* and 30% identity with the CapC protein of *Staphylococcus aureus* (Rubens et al., Mol. Microbiol., 8, 843–885, 1993; Lin et al., J. Bacteriol., 176, 7005–7016, 1994). The precise function of these genes is still unknown, apart from the fact that they are essential for the synthesis of the capsule which consists of polysaccharides coupled to the phospholipids of the outer membrane of the bacteria.

The epsC gene (nucleotides 2547–3239) codes for an EpsC protein (SEQ ID NO:4) having 52% identity with the CpsB protein of *Streptococcus agalactiae* which is involved in the synthesis of the capsule (Rubens et al.). EpsC also has 23% identity, 49% similarity and a hydrophobicity profile comparable to that of the CLD proteins of *Salmonella typhimurium*, *Salmonella enterica* and *Escherichia coli* (Batchelor et al., J. Bacteriol., 174, 5228–5236, 1992; Bastin et al., Mol. Microbiol., 7, 725–734, 1993). It should be pointed out that the CLD proteins are involved in the control of the length of the polysaccharide chains during their biosynthesis.

The epsD gene (nucleotides 3249–3995) codes for an EpsD protein (SEQ ID NO:5) having 60.5% identity with the CpsC protein of *Streptococcus agalactiae*, having 34.5% identity with the CapA protein of *Staphylococcus aureus* and having 33% identity with the ExoP protein of *Rhizobium meliloti* (Rubens et al., Lin et al.; Becker et al., Mol. Gen. Genet., 241, 367–379, 1993). The ExoP protein is a membrane protein which is involved in the translocation of EPS and/or of EPS precursors.

The epsE gene (nucleotides 4051–4731) codes for an EpsE protein (SED ID-NO:6) displaying significant homologies with many proteins having galactosyltransferase activity (Rubens et al.). Hence this gene probably codes for a galactosyltransferase.

It may be noted that the epsB, C, D and E genes of *S. thermophilus* Sfi6 are similar to those of the operon of *S. agalactiae* comprising the cpsA, B, C and D genes (Rubens et al.,). Furthermore, they are organized in the same way. Although the polysaccharides of the capsule and the EPS of the two strains are very different, this indicates that a chromosomal region has probably been transferred between these two species.

The epsF gene (nucleotides 4898–5854) codes for an EpsF protein (SEQ ID NO:7) having, respectively, 24.5% and 23% identity with the CapH and CapM proteins of *S. mutans* which are probably involved as glycosyltransferases in the biosynthesis of the capsule (Lin et al.).

The epsG gene (nucleotides 6425–7540) codes for an EpsG protein (SEQ ID NO:8) having 20.5% identity and 50% similarity with the N-acetylglucosaminetransferase of *Salmonella typhimurium* LT2 which is involved in the biosynthesis of the LPS polysaccharide of the outer membrane (MacLachlan et al., J. Bacteriol., 173, 7151–7163, 1991). Since an N-acetylglucosamine is not involved in the biosynthesis of the EPS of the strain Sfi6 (there is no acetylated glucose), the epsG gene probably codes for a glucosyltransferase, an N-acetylgalactosyltransferase or an N-acetylglucosyltransferase having N-acetylglucosamine epimerase activity.

The epsH gene (nucleotides 7736–8212) codes for an EpsH protein (SEQ ID NO:9) having strong homologies with NodL-LacA-CysE acetyltransferases (Downie et al., Mol. Microbiol. 3, 1649–1651, 1989). Accordingly, the EpsH protein could be an acetyltransferase involved in the biosynthesis of the N-acetylgalactosamine of the EPS.

The epsI gene (nucleotides 8221–9192) codes for an EpsI protein (SEQ ID NO:10) having 24% identity with a protein, encoded by the RfbV ORF of the rfb cluster of *Salmonella typhimurium*, which is probably a glycosyltransferase (Jiang et al.; Liu et al., J. Bacteriol., 177, 4084–4088, 1995).

The epsJ gene (nucleotides 9285–10364) codes for an EpsJ protein (SEQ ID NO:11) having 20% identity and a hydrophobicity profile comparable to that of a protein of an ORF of the rfb cluster of *Salmonella enterica* which is itself similar to a polymerase of the O antigen of group B and C2 salmonellae (Lee et al., J. Gen. Microbiol., 138, 1843–1855, 1992; Morona et al., J. Bacteriol. 176, 733–747, 1994). The epsJ gene could hence encode an EPS polymerase which might polymerize the tetrasaccharide unit of the EPS.

The epsK gene (nucleotides 10392–11339) codes for an EpsK protein (SEQ ID NO: 12) having 18% identity and 42% similarity with the protein, encoded by the lipB gene of *Neisseria meningitidis*, which is involved in the biosynthesis of the capsule by coupling polysaccharides to the phospholipids of the outer membrane (Frosch et al., Mol. Microbiol., 8, 483–493, 1993). Given that the *S. thermophilus* bacteria do not have an outer membrane (Gram-positive), the epsK gene could hence encode an enzyme involved in the coupling of the EPSs to the phospholipids of the cell membrane which, in concert with an EPS transport molecule (probably EpsC and EpsD) and an enzyme which detaches EPSs, might participate in the transport of the EPS through the membrane (model in agreement with the one put forward by Frosch et al.).

Moreover, it may be pointed out that the transposon Tn916 is integrated into the epsK gene of the mutant No. 1 used to identify the eps operon (see point I.6 above), between nucleotides 10540–10541 of the sequence SEQ ID NO:1.

The epsL gene (nucleotides 11302–12222) codes for an EpsL protein (SEQ ID NO:14) which does not display any homology with known proteins. The first 38 nucleotides are covered by the 3' end of epsK, suggesting a coordinated expression of the two proteins and an activity of the EpsL protein in the membrane transport of the EPS.

The epsM gene (nucleotides 12233–13651) codes for an EpsM protein (SEQ ID NO:13) which does not display any homology with known proteins of the Swiss-Prot data bank. This gene is definitely involved in the biosynthesis of the EPS of the strain Sfi6, since there is not, upstream, a specific promoter for this gene.

The orfZ gene (13732–14305 on the complementary strand) is present in the reverse orientation relative to the remainder of the ORFs of the eps operon. Accordingly, it is probably not involved in the biosynthesis of the EPS of the strain Sfi6. Furthermore, it does not display any homology with known proteins of the Swiss-Prot data bank.

In conclusion, the chromosomal inserts isolated from the 11 pSF vectors (see point I.6 above) cover a chromosomal region of *S. thermophilus* strain Sfi6 which is manifestly involved in the biosynthesis of the EPS. 13 complete genes which comprise, upstream, a promoter delimiting the beginning of the eps operon could thus be identified.

Example II: inactivation of the epsJ gene

The epsJ gene of the eps operon is inactivated by homologous recombination in order to confirm its importance in the biosynthesis of the EPS.

For this purpose, a DraI-SalI fragment is isolated from plasmid pGEMT containing the 0.8-kb PCR fragment (see Example I.6 above) and ligated into the temperature-sensitive plasmid pSA3 (Dao et al., Appl. Environ. Microbiol., 49, 115–119, 1985) previously digested with EcoRV and SalI, the *E. coli* strain XL1-blue is transformed with the ligation product, transformants are selected, a recombinant plasmid is isolated, and *S. thermophilus* strain Sfi6 is transformed by electroporation with the recombinant plasmid by means of a method adapted from the one described by Slos et al. (Appl. Environ. Microbiol., 57, 1333–1339, 1991). The cells subjected to a discharge of 2.1 kV, 25 µF and 400Ω are resuspended in 1 ml of HJL medium, which is incubated for 4 h at 37° C. (permissive temperature), the cells are plated out on LM17 solid medium supplemented with 2.5 µg/ml of erythromycin, which is incubated for 16 h at 37° C., and the transformed colonies which survive are then selected. The selected colonies are then incubated in 2 ml of HJL medium supplemented with 2.5 µg/ml of erythromycin until the optical density at 600 nm ($OD_{600}$) of the culture reaches 0.2, the culture is subjected to 45° C. until the $OD_{600}$ reaches 1.0 (the plasmid no longer replicates), and dilutions of the culture are then plated out on solid LM17 medium supplemented with 2.5 µg/ml of erythromycin, which is incubated for 12 h at 45° C.

The colonies which survive have integrated the recombinant pSA3 plasmid into the epsJ gene. This may be verified by Southern blotting of a chromosomal DNA preparation of the surviving colonies, digested with EcoRI (cuts only once in pSA3), and hybridization of the Southern blot filter with the abovementioned radioactive DraI-SalI fragment. Colonies which have integrated plasmid pSA3 display two bands on the Southern blot filter. Furthermore, colonies which have integrated the recombinant pSA3 plasmid into epsJ display an EPS(−) phenotype on ruthenium red solid medium, and have lost their ropy character in MSK milk (see Example I.4 above).

Example III: inactivation of the eps A, B, C, D, E, F, G, H, I, K, L and M genes It was shown in Examples I and II that inactivation of the epsK and epsJ genes, by insertion of a transposon or of an integrative plasmid, interrupts EPS biosynthesis in the strain Sfi6.

Similarly, the other genes of the eps operon of the strain Sfi6 may be inactivated by homologous recombination, and an interruption of EPS biosynthesis may thus be observed. For this purpose, a fragment of an ORF originating from one of the 11 pFS vectors described in Example I.6 above is amplified by PCR. It is cloned into plasmid pSA3, then transformed and integrated into the strain Sfi6 under the same conditions as those described in the previous example.

Example IV: restoration of EPS production pFS30 is cut with EcoRI, the fragments are separated, the 5.5-kb fragment is ligated to pFS14 previously digested with EcoRI, XL1-blue cells are transformed with the ligation product, transformed clones displaying a correct orientation of the inserts are selected, a plasmid called pFS30-14 is isolated, a central EcoRI fragment of pFS65 is ligated to pFS30-14 previously cut with EcoRI, XL1-blue cells are transformed with the ligation product, and transformed clones displaying a correct orientation of the inserts are then selected. The resultant recombinant plasmid, called pFS30-65-14, comprises nucleotides 1702 to 14602 of the sequence SEQ ID NO: 1.

pFS30-65-14 is then cut with SalI and SmaI, the 12.9 kb fragment is separated and ligated to pSA3 previously cut with EcoRV and SalI. XL1-blue cells are transformed with the ligation product, transformed clones are selected and recombinant pSA3 plasmids are isolated.

The *S. thermophilus* strain CNCM I-1292, deposited on 29th Mar. 1993, is transformed by electroporation with the recombinant pSA3 plasmids. This Gram-positive strain displays under the microscope an appearance of non-flagellated cocci forming small chains, does not make spores, is a facultative anaerobe, does not produce any EPS and possesses in its genome 1000 bp corresponding to the 5' end of the eps operon. The recombinant pSA3 plasmid can hence integrate into the genome of the strain CNCM I-1292. Some of the transformed clones display an EPS(+) phenotype on ruthenium red solid medium, and a ropy character in MSK milk.

Example V: restoration of EPS production

The chromosome of the strain Sfi6 is digested with enzymes which do not cut in the sequence SEQ ID NO:1 (BamHI, SalI, NruI, StuI), the digestion product is separated on agarose gel, the 15–25-kb bands are eluted and ligated into pSA3 previously cut with a suitable restriction enzyme, the *S. thermophilus* strain CNCM I-1292 is transformed by electroporation, and transformants are then selected by transfer of the colonies onto a filter followed by hybridization of their DNA with the insert of pFS14 previously made radioactive. Some of the transformed clones display an EPS(+) phenotype on ruthenium red solid medium, and a ropy character in MSK milk.

Example VI: modification of an EPS

The *S. thermophilus* strain CNCM I-1422, deposited on 18th May 1994, is transformed by electroporation with the recombinant pSA3 plasmid of Example V. This Gram-positive strain displays under the microscope an appearance of non-flagellated cocci forming small chains, does not make spores, is a facultative anaerobe and produces an EPS having the composition Glc:Gal=2:2.

Example VII: modification of an EPS

The *S. thermophilus* strain CNCM I-1351, deposited on 5th Aug. 1993, is transformed by electroporation with the recombinant pSA3 plasmid of Example V. This Gram-positive strain displays under the microscope an appearance of non-flagellated cocci forming small chains, does not make spores, is a facultative anaerobe and produces an EPS having the composition Glc:Gal:Rha=1:3:2.

Example VIII: modification of an EPS

The chromosomal DNA of the strain CNCM I-1590 is isolated by the method of Slos et al. (Appl. Environ. Microbiol., 57, 1333–1339, 1991). The DNA preparation is digested with SacI and BamHI, the DNA fragments are separated by electrophoresis on 0.7% agarose gel, the 12- to 16-kb fragments are eluted, and the DNA extracted is ligated to the vector pJIM2279 (obtained from P. Renault, INRA, Jouy-en-Josas, Paris, France) previously digested with SacI and BamHI and then dephosphorylated. *Lactococcus lactis* strain MG1363 (J. Bacteriol., 154, 1–9, 1983), cultured on GM17 medium at 30° C., is transformed by the method of De Vos et al. (Gene, 85, 169–176, 1989). The transformed clones are selected by hybridization of the genomic DNA of the clones with one of the probes having the sequences SEQ ID NO: 15, 16, 17, 18 and 19. Among 400 transformants, 6 positive clones are selected, one of which comprises a plasmid called pFS101 shown in FIG. 1.C.

To determine whether plasmid pFS101 is capable of inducing the production of recombinant EPS, *L. lactis* MG1363 is retransformed with pFS101 and plated out directly on ruthenium red solid medium. For comparison, *L. lactis* MG1363 is transformed with the plasmid pJIM2279 and is then plated out directly on ruthenium red solid medium. The results show that all the colonies comprising pJIM2279 have a red phenotype (3000 EPS(−) colonies), while more than 99.5% of the colonies comprising pFS101 have a white phenotype (800 EPS(+) colonies, apart from 2 colonies). Hence *L. lactis* strain MG1363 transformed with pFS101 produces a recombinant EPS.

Production of the EPS of *L. lactis* strain MG1363 transformed with pFS101 is brought about by culturing the organism in MAM medium, at a pH of 5.5, at 30° C. with magnetic stirring at 60 rpm. The recombinant EPS is isolated by mixing the culture medium with 40% of trichloroacetic acid, centrifuging the mixture for 20 min at 8000 g, mixing the precipitate with an equal volume of acetone, incubating the mixture at 4° C. for 12 h, precipitating the mixture at 10,000 g for 1 h, suspending the precipitate in water, adjusting the pH of the mixture to 7, dialysing it against water for 24 h, ultracentrifuging it at 100,000 g for 1 h, recovering the supernatant and then lyophilizing the supernatant. For comparison, *L. lactis* strain MG1363 transformed with pJIM2279 is cultured under the same conditions and the sugars are isolated in the same manner.

The total amount of neutral sugars is determined by the method of Dubois et al. (Anal. Chem., 28, 350–356, 1956). The results show that the strain transformed with pFS101 produces 10 mg/l of sugars, expressed as glucose equivalents, while the strain transformed with pJIM2279 produces traces of sugar (<1 mg/l).

Figure 2:
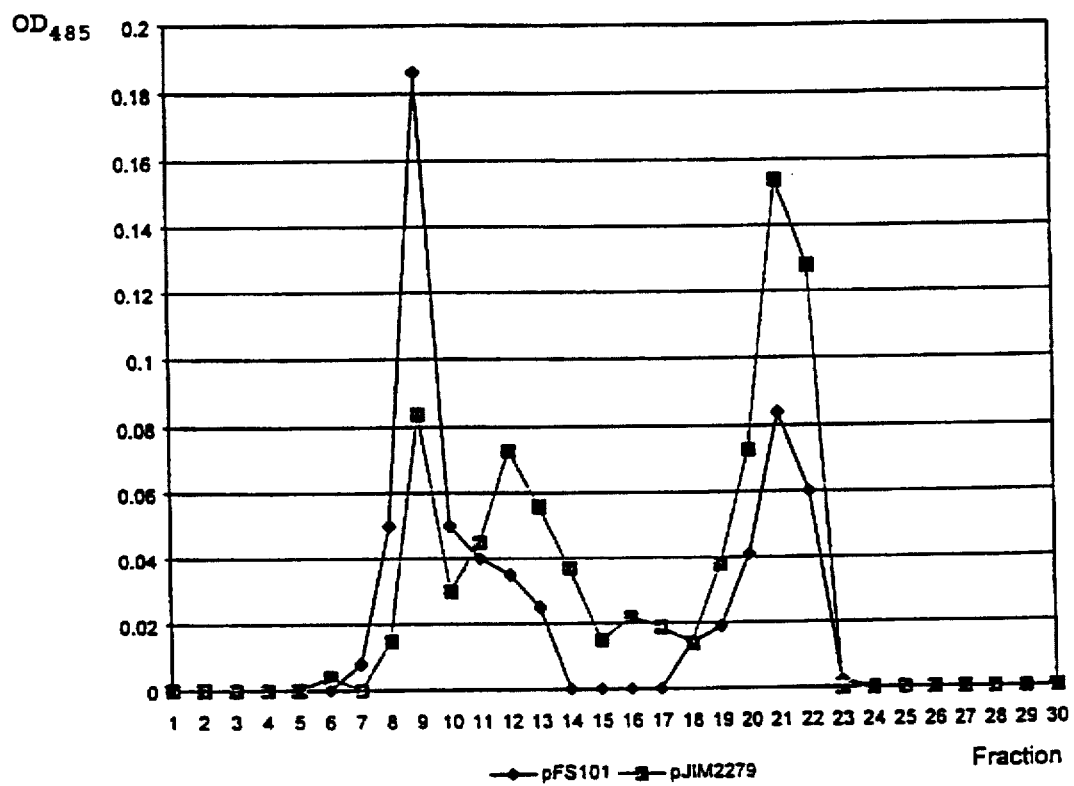

The molecular weight of the recombinant EPS is estimated by chromatography on a Superose-6 (Pharmacia) gel filtration column which is connected to the FPLC system (Pharmacia) previously calibrated with commercial dextran (Sigma) of $2 \times 10^6$ to $5 \times 10^3$ daltons (Da). For this purpose, 0.25 to 1 ml of a sample comprising 250 µg of neutral sugars is applied to the column, which is eluted with a flow of 0.5 ml/min in 50 mM phosphate buffer pH 7.2. For comparison, the sugars produced by the strain transformed with pJIM2279 are separated in the same manner. The results presented in FIG. 2 show that the strain transformed with pJIM2279 produces a small amount of heterogeneous polysaccharides whose origin is definitely the cell wall ($2-0.5 \times 10^6$ Da; fractions 8–15 ) and a large amount of low molecular weight oligosaccharides (mono-and disaccharides; fractions 20–22). In contrast, the strain transformed with pFS101 manifestly displays a recombinant EPS with a high molecular weight of approximately $2 \times 10^6$ Da (fraction 9).

The sugar composition of the recombinant EPS is determined by gas chromatography by the method of Neeser et al. (Anal. Biochem., 142, 58–67, 1984). The results show that the culture medium of the strain transformed with pFS101 comprises, in terms of molarity, a 1:3 ratio of Glc:Gal. Traces of rhamnose originating from the cell wall may be detected. In contrast, no GalNac is detected.

Hence the composition of the EPS produced by *L. lactis* strain MG1363 transformed with pFS101 is different from that of the EPS produced by the *S. thermophilus* strain CNCM I-1590. It may reasonably be estimated that the structure of the recombinant EPS is the same as that of the EPS of the strain CNCM I-1590, except for the fact that GalNac is replaced by a galactose.

---

What is claimed is:

1. Method for the production of an exopolysaccharide comprising cloning a DNA fragment encoding amino acid sequences of SEQ ID NO's:2-14 into a vector construct, transforming a bacterial host cell with the vector construct, and culturing the transformed bacterial host cell under suitable conditions for the production of an exopolysaccharide.

2. Method according to claim 1, in which the vector comprises, in addition, a promoter sequence and a translation activator sequence which are functional in the said host cell.

3. Method for restoring the production of an exopolysaccharide in vivo comprising cloning a DNA fragment encoding at least one amino acid sequence or a fragment of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, and SEQ ID NO:14 into a vector construct, transforming a bacterial host cell with the vector construct and culturing the transformed bacterial host cell under suitable conditions for the production of an exopolysaccharide.

4. Method according to claim 1, wherein the DNA fragment comprises the DNA sequence of SEQ ID NO:1.

5. Method according to claim 1, wherein the vector comprises sequences permitting integration into the bacterial host cell.

6. Method according to claim 1, wherein the bacterial host cell is a lactic bacterium.

7. Method according to claim 6, wherein the lactic bacterium is a member selected from the group consisting of Streptococcus cremoris, Streptococcus lactis, Lactobacillus casei, subsp. casei, Lactobacillus sake, Streptococcus thermophilus, Lactobacillus delbruecki subsp. bulgaricus and Lactobacillus helveticus.

8. Method according to claim 3, wherein the DNA fragment comprises at least one gene or a fragment of at least one gene chosen from the group of genes delimited in the nucleic acid sequence SEQ ID NO:1 by nucleotides 352-1803, 1807-2535, 2547-3239, 3249-3995, 4051-4731, 4898-5854, 6425-7540, 7736-8212, 8221-9192, 9285-10364, 10392-11339, 11302-12222 and 12233-13651.

9. Method according to claim 3, wherein the vector comprises a sequence permitting autonomous replication into the bacterial host cell.

10. Method according to claim 3 wherein the vector comprises a sequence permitting integration into the bacterial host cell.

11. Method according to claim 3, wherein the bacterial host cell is a lactic bacterium.

12. Method according to claim 3, wherein the lactic bacterium is a member selected from the group consisting of Streptococcus cremoris, streptococcus lactis, Lactobacillus casei, subsp. casei, Lactobacillus sake, Streptococcus thermophilus, Lactobacillus delbruecki subsp. bulgaricus and Lactobacillus helveticus.

13. Method for the production of an exopolysaccharide comprising cloning a DNA fragment which is more than 90% homologous to the nucleic acid sequence of at least one gene chosen from the group of genes delimited in the nucleic acid sequence of SEQ ID NO:1 by nucleotides 352-1803, 1807-2535, 2547-3239, 3249-3995, 4051-4731, 4898-5854, 6425-7540, 7736-8212, 8221-9192, 9285-10364, 10392-11339, 11302-12222 and 12233-13651 and which encodes a protein involved in the biosynthesis of an exopolysaccharide possessing the repeat structure:

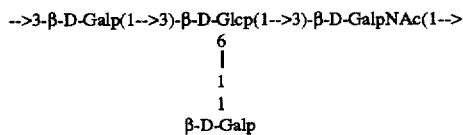

into a vector construct, transforming a bacterial host cell with the vector construct, and culturing the transformed bacterial host cell under suitable conditions for the production of an exopolysaccharide.

14. Method according to claim 13, wherein the vector comprises a sequence permitting autonomous replication in the bacterial host cell.

15. Method according to claim 13, wherein the vector comprises a sequence permitting integration into the bacterial host cell.

16. Method according to claim 13, wherein the bacterial host cell is a lactic bacterium.

17. Method according to claim 16, wherein the lactic bacterium is a member selected from the group consisting of Streptococcus cremoris, Streptococcus lactis, Lactobacillus casei, subsp. casei, Lactobacillus sake, Streptococcus thermophilus, Lactobacillus delbruecki subsp. bulgaricus and Lactobacillus helveticus.

18. Method according to claim 1, wherein the bacterial host cell does not produce an exopolysaccharide having the tetrasaccharide repeat structure:

→3)-β-D-Galp(1→3)-β-D-Glcp(1→3)-β-D-GalpNAc(1→.
```
        6
        |
        1
     β-D-Galp
```

19. Method according to claim 3, wherein the bacterial host cell does not produce an exopolysaccharide having the tetrasaccharide repeat structure:

→3)-β-D-Galp(1→3)-β-D-Glcp(1→3)-β-D-GalpNAc(1→.
```
        6
        |
        1
     β-D-Galp
```

20. Method according to claim 13, wherein the bacterial host cell does not produce an exopolysaccharide having the tetrasaccharide repeat structure:

→3)-β-D-Galp(1→3)-β-D-Glcp(1→3)-β-D-GalpNAc(1→.
```
        6
        |
        1
     β-D-Galp
```

21. Method according to claim 3, in which the vector comprises, in addition, a promoter sequence and translation activator sequence which are functional in the bacterial host cell.

* * * * *

UNITED STATES PATENT AND TRADEMARK OFFICE
CERTIFICATE OF CORRECTION

PATENT NO. : 5,786,184

DATED : July 28, 1998

INVENTOR(S) : B. Mollet et al.

It is certified that error appears in the above-identified patent and that said Letters Patent is hereby corrected as shown below:

Column 72, lines 39-43, change the repeat structure to the following:

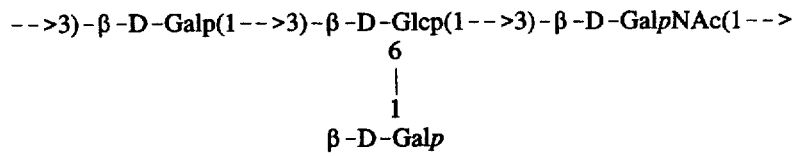

$$\begin{array}{c} \text{-->3)-}\beta\text{-D-Galp(1-->3)-}\beta\text{-D-Glcp(1-->3)-}\beta\text{-D-Gal}p\text{NAc(1-->}\\ 6\\ |\\ 1\\ \beta\text{-D-Gal}p \end{array}$$

Signed and Sealed this

Twenty-ninth Day of September, 1998

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:

( A ) LENGTH: 14602 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 352..1803
    ( D ) OTHER INFORMATION: /product="epsA"

( i x ) FEATURE:
    ( A ) NAME/KEY: CDS
    ( B ) LOCATION: 1807..2535
    ( D ) OTHER INFORMATION: /product="epsB"

( i x ) FEATURE:
    ( A ) NAME/KEY: CDS
    ( B ) LOCATION: 2547..3239
    ( D ) OTHER INFORMATION: /product="epsC"

( i x ) FEATURE:
    ( A ) NAME/KEY: CDS
    ( B ) LOCATION: 3249..3995
    ( D ) OTHER INFORMATION: /product="epsD"

( i x ) FEATURE:
    ( A ) NAME/KEY: CDS
    ( B ) LOCATION: 4051..4731
    ( D ) OTHER INFORMATION: /product="epsE"

( i x ) FEATURE:
    ( A ) NAME/KEY: CDS
    ( B ) LOCATION: 4898..5854
    ( D ) OTHER INFORMATION: /product="epsF"

( i x ) FEATURE:
    ( A ) NAME/KEY: CDS
    ( B ) LOCATION: 6425..7540
    ( D ) OTHER INFORMATION: /product="epsG"

( i x ) FEATURE:
    ( A ) NAME/KEY: CDS
    ( B ) LOCATION: 7736..8212
    ( D ) OTHER INFORMATION: /product="epsH"

( i x ) FEATURE:
    ( A ) NAME/KEY: CDS
    ( B ) LOCATION: 8221..9192
    ( D ) OTHER INFORMATION: /product="epsI"

( i x ) FEATURE:
    ( A ) NAME/KEY: CDS
    ( B ) LOCATION: 9285..10364
    ( D ) OTHER INFORMATION: /product="epsJ"

( i x ) FEATURE:
    ( A ) NAME/KEY: CDS
    ( B ) LOCATION: 10392..11339
    ( D ) OTHER INFORMATION: /product="epsK"

( i x ) FEATURE:
    ( A ) NAME/KEY: misc_feature
    ( B ) LOCATION: 11302..12222
    ( D ) OTHER INFORMATION: /product="CDS (eps L) covering CDS
        ( e p s   k ) on nucleotides 10392-11339"

( i x ) FEATURE:
    ( A ) NAME/KEY: CDS
    ( B ) LOCATION: 12233..13651
    ( D ) OTHER INFORMATION: /product="epsM"

( i x ) FEATURE:
    ( A ) NAME/KEY: misc_feature
    ( B ) LOCATION: 13732..14305
    ( D ) OTHER INFORMATION: /function="CDS on the
        complementary strand"
        / product="orfz"

( i x ) FEATURE:
    ( A ) NAME/KEY: terminator
    ( B ) LOCATION: 230..252

-continued ( i x ) FEATURE:
    ( A ) NAME/KEY: promoter
    ( B ) LOCATION: 274..302

( i x ) FEATURE:
    ( A ) NAME/KEY: RBS
    ( B ) LOCATION: 340..345

( x i ) SEQUENCE DESCRIPTION: SEQ ID NO:1:

```
TAGTTTGTAA AAGGACGCCA TTTGGTCGTC CTTTTGTGTT GTAGCTAATA TCTGTTCGAA        60

GTGATAATAA GTTAAAATTT TTCAAACTAC TAGAAAAAAT AAAAATATTT GGAAGAAGAA       120

GACTTATAAT AAATAGGTAA ATATCTGACA ATTTAAAGTT TAACTACTAA AAATGTAAAA       180

GATAGTTCAC AATATAATGG AAAATGATAT AAATTAAATG ATTGATATCA TAATGAAAAA       240

CGTTTTCTTA TTTTTTTGAA AAAAGAATGA CAATTGAAAT GAGGTTGTAT TAATGTTATA       300

ATAATAATAA TAATGGGGAA TACCTAATTT TAATTTTTAG GAGCAATTTA T ATG AGT        357
                                                         Met Ser
                                                         1

TCG CGT ACG AAT CGT AAG CAA AAG CAT ACG AGT AAT GGA TCG TGG GGG         405
Ser Arg Thr Asn Arg Lys Gln Lys His Thr Ser Asn Gly Ser Trp Gly
        5                  10                 15

ATG GTC AAC GTT GGG TTG ACC ATC CTG TAT GCT ATT TTA GCA TTG GTC         453
Met Val Asn Val Gly Leu Thr Ile Leu Tyr Ala Ile Leu Ala Leu Val
     20                 25                 30

TTA TTA TTC ACC ATG TTC AAT TAT AAT TTC CTA TCC TTT AGG TTT TTG         501
Leu Leu Phe Thr Met Phe Asn Tyr Asn Phe Leu Ser Phe Arg Phe Leu
 35                 40                 45                 50

AAC ATC ATT ATC ACC ATT GGT TTG TTG GTA GTT CTT GCT ATT AGC ATC         549
Asn Ile Ile Ile Thr Ile Gly Leu Leu Val Val Leu Ala Ile Ser Ile
                 55                 60                 65

TTC CTT CAG AAG ACT AAG AAA TTA CCA CTA GTG ACA ACG GTT GTA CTG         597
Phe Leu Gln Lys Thr Lys Lys Leu Pro Leu Val Thr Thr Val Val Leu
         70                 75                 80

GTT ATC TTC TCG CTA GTT TCT CTG GTT GGT ATT TTT GGT TTT AAA CAA         645
Val Ile Phe Ser Leu Val Ser Leu Val Gly Ile Phe Gly Phe Lys Gln
             85                 90                 95

ATG ATT GAC ATC ACT AAC CGT ATG AAT CAG ACA GCA GCA TTT TCT GAA         693
Met Ile Asp Ile Thr Asn Arg Met Asn Gln Thr Ala Ala Phe Ser Glu
100                105                110

GTA GAA ATG AGC ATC GTG GTT CCT AAG GAA AGT GAC ATC AAA GAT GTG         741
Val Glu Met Ser Ile Val Val Pro Lys Glu Ser Asp Ile Lys Asp Val
115                120                125                130

AGC CAG CTT ACT AGC GTA CAG GCA CCT ACT AAG GTT GAT AAG AAC AAT         789
Ser Gln Leu Thr Ser Val Gln Ala Pro Thr Lys Val Asp Lys Asn Asn
                135                140                145

ATC GAG ATC TTG ATG TCA GCT CTC AAA AAA GAT AAA AAA GTT GAT GTT         837
Ile Glu Ile Leu Met Ser Ala Leu Lys Lys Asp Lys Lys Val Asp Val
            150                155                160

AAA GTT GAT GAT GTT GCC TCA TAT CAA GAA GCT TAT GAT AAT CTC AAG         885
Lys Val Asp Asp Val Ala Ser Tyr Gln Glu Ala Tyr Asp Asn Leu Lys
        165                170                175

TCT GGC AAA TCT AAA GCT ATG GTC TTG AGT GGC TCT TAT GCT AGC CTA         933
Ser Gly Lys Ser Lys Ala Met Val Leu Ser Gly Ser Tyr Ala Ser Leu
180                185                190

TTA GAG TCT GTC GAT AGT AAT TAT GCT TCA AAT CTA AAA ACA ATT TAT         981
Leu Glu Ser Val Asp Ser Asn Tyr Ala Ser Asn Leu Lys Thr Ile Tyr
195                200                205                210

ACT TAT AAA ATT AAA AAG AAG AAT AGC AAC TCT GCA AAC CAA GTA GAT        1029
Thr Tyr Lys Ile Lys Lys Lys Asn Ser Asn Ser Ala Asn Gln Val Asp
            215                220                225
```

| | | | | | | | | | | | | | | | | |
|---|---|---|---|---|---|---|---|---|---|---|---|---|---|---|---|---|
| TCA | AGA | GTC | TTC | AAT | ATT | TAT | ATT | AGT | GGT | ATT | GAT | ACC | TAC | GGT | CCG | 1077 |
| Ser | Arg | Val | Phe 230 | Asn | Ile | Tyr | Ile | Ser 235 | Gly | Ile | Asp | Thr | Tyr 240 | Gly | Pro | |
| ATT | TCA | ACA | GTG | TCA | CGT | TCA | GAT | GTC | AAT | ATC | ATT | ATG | ACA | GTA | AAC | 1125 |
| Ile | Ser | Thr 245 | Val | Ser | Arg | Ser | Asp 250 | Val | Asn | Ile | Ile | Met 255 | Thr | Val | Asn | |
| ATG | AAT | ACA | CAT | AAG | ATT | CTC | TTG | ACG | ACT | ACT | CCA | CGT | GAT | GCA | TAC | 1173 |
| Met | Asn | Thr 260 | His | Lys | Ile | Leu | Leu 265 | Thr | Thr | Thr | Pro 270 | Arg | Asp | Ala | Tyr | |
| GTT | AAG | ATT | CCT | GGT | GGT | GGG | GCA | GAC | CAG | TAT | GAT | AAA | TTA | ACC | CAC | 1221 |
| Val 275 | Lys | Ile | Pro | Gly 280 | Gly | Gly | Ala | Asp | Gln 285 | Tyr | Asp | Lys | Leu | Thr 290 | His | |
| GCA | GGT | ATT | TAT | GGC | GTT | GAA | ACA | TCT | GAA | CAA | ACT | CTA | GAA | GAT | CTT | 1269 |
| Ala | Gly | Ile | Tyr | Gly 295 | Val | Glu | Thr | Ser 300 | Glu | Gln | Thr | Leu | Glu 305 | Asp | Leu | |
| TAT | GGT | ATT | AAG | CTT | GAT | TAC | TAT | GCA | CGA | ATT | AAC | TTC | ACA | TCT | TTC | 1317 |
| Tyr | Gly | Ile | Lys 310 | Leu | Asp | Tyr | Tyr | Ala 315 | Arg | Ile | Asn | Phe | Thr 320 | Ser | Phe | |
| CTT | AAG | TTG | ATT | GAC | CAA | CTT | GGT | GGT | GTG | ACA | GTC | CAT | AAT | GAT | CAA | 1365 |
| Leu | Lys | Leu 325 | Ile | Asp | Gln | Leu | Gly 330 | Gly | Val | Thr | Val | His 335 | Asn | Asp | Gln | |
| GCT | TTC | ACA | CAA | GAG | AAG | TTT | GAT | TTC | CCG | GTT | GGA | GAT | ATC | CAA | ATG | 1413 |
| Ala | Phe 340 | Thr | Gln | Glu | Lys | Phe 345 | Asp | Phe | Pro | Val | Gly 350 | Asp | Ile | Gln | Met | |
| AAT | TCA | GAG | CAA | GCA | CTT | GGA | TTT | GTT | CGT | GAA | CGC | TAT | AAT | TTA | GAT | 1461 |
| Asn 355 | Ser | Glu | Gln | Ala | Leu 360 | Gly | Phe | Val | Arg | Glu 365 | Arg | Tyr | Asn | Leu | Asp 370 | |
| GGC | GGA | GAT | AAT | GAC | CGT | GGT | AAA | AAC | CAG | GAG | AAA | GTT | ATT | TCT | GCG | 1509 |
| Gly | Gly | Asp | Asn | Asp 375 | Arg | Gly | Lys | Asn | Gln 380 | Glu | Lys | Val | Ile | Ser 385 | Ala | |
| ATT | TTA | AAC | AAG | TTG | GCT | TCT | CTA | AAA | TCT | GTA | TCA | AAC | TTT | ACT | TCA | 1557 |
| Ile | Leu | Asn | Lys 390 | Leu | Ala | Ser | Leu | Lys 395 | Ser | Val | Ser | Asn | Phe 400 | Thr | Ser | |
| ATC | GTT | AAT | AAT | CTC | CAA | GAC | TCT | GTC | CAA | ACG | AAT | ATG | TCT | TTG | AAT | 1605 |
| Ile | Val | Asn 405 | Asn | Leu | Gln | Asp | Ser 410 | Val | Gln | Thr | Asn | Met 415 | Ser | Leu | Asn | |
| ACC | ATT | AAC | GCT | TTG | GCT | AAT | ACA | CAA | CTT | GAA | TCA | GGT | TCT | AAA | TTT | 1653 |
| Thr | Ile | Asn | Ala | Leu 420 | Ala | Asn | Thr | Gln | Leu 425 | Glu | Ser | Gly | Ser 430 | Lys | Phe | |
| ACG | GTG | ACT | TCT | CAA | GCA | GTA | ACA | GGT | ACA | GGT | TCA | ACC | GGA | CAA | TTG | 1701 |
| Thr | Val | Thr 435 | Ser | Gln | Ala | Val | Thr 440 | Gly | Thr | Gly | Ser | Thr 445 | Gly | Gln | Leu 450 | |
| ATC | TCT | TAT | GCG | ATG | CCA | AAT | TCT | AGT | CTT | TAC | ATG | ATG | AAA | CTA | GAT | 1749 |
| Ile | Ser | Tyr | Ala | Met 455 | Pro | Asn | Ser | Ser | Leu 460 | Tyr | Met | Met | Lys | Leu 465 | Asp | |
| AAT | TCG | AGT | GTG | GAA | AGT | GCC | TCT | CAA | GCT | ATC | AAA | AAA | TTG | ATG | GAG | 1797 |
| Asn | Ser | Ser | Val 470 | Glu | Ser | Ala | Ser | Gln 475 | Ala | Ile | Lys | Lys | Leu 480 | Met | Glu | |
| GAA | AAA | TAA | GTG | ATT | GAC | GTT | CAC | TCA | CAT | ATT | GTT | TTT | GAT | GTT | GAT | 1845 |
| Glu | Lys | | Val 1 | Ile | Asp | Val | His 5 | Ser | His | Ile | Val | Phe 10 | Asp | Val | Asp | |
| GAT | GGT | CCT | GAA | ACT | TTA | GAA | GAA | AGT | TTA | GAC | CTC | ATT | GGT | GAA | AGT | 1893 |
| Asp | Gly | Pro 15 | Glu | Thr | Leu | Glu | Glu 20 | Ser | Leu | Asp | Leu | Ile 25 | Gly | Glu | Ser | |
| TAC | GCC | CAG | GGG | GTA | CGT | AAG | ATT | GTT | TCA | ACA | TCC | CAT | CGT | CGT | AAG | 1941 |
| Tyr | Ala | Gln 30 | Gly | Val | Arg | Lys 35 | Ile | Val | Ser | Thr | Ser 40 | His | Arg | Arg | Lys 45 | |
| GGG | ATG | TTT | GAG | ACT | CCA | GAG | GAT | AAA | ATT | TTT | GCC | AAC | TTT | AAA | AAA | 1989 |
| Gly | Met | Phe | Glu | Thr 50 | Pro | Glu | Asp | Lys | Ile 55 | Phe | Ala | Asn | Phe | Lys 60 | Lys | |

| | | | | | | | | | | | | | | | | |
|---|---|---|---|---|---|---|---|---|---|---|---|---|---|---|---|---|
| GTA | AAA | GCA | GAA | GCA | GAA | GCA | CTT | TAT | CCA | GAC | TTA | ACT | ATT | TAT | TAT | 2037 |
| Val | Lys | Ala | Glu<br>65 | Ala | Glu | Ala | Leu | Tyr<br>70 | Pro | Asp | Leu | Thr | Ile<br>75 | Tyr | Tyr | |
| GGA | GGT | GAA | CTT | TAT | TAC | ACC | TCA | GAC | ATT | GTG | GAG | AAA | CTT | GAA | AAG | 2085 |
| Gly | Gly | Glu<br>80 | Leu | Tyr | Tyr | Thr | Ser | Asp<br>85 | Ile | Val | Glu | Lys<br>90 | Leu | Glu | Lys | |
| AAT | CTC | ATT | CCG | CGC | ATG | CAC | AAC | ACT | CAA | TTT | GCT | TTA | ATT | GAG | TTT | 2133 |
| Asn | Leu<br>95 | Ile | Pro | Arg | Met | His<br>100 | Asn | Thr | Gln | Phe | Ala<br>105 | Leu | Ile | Glu | Phe | |
| AGT | GCT | CGC | ACA | TCT | TGG | AAA | GAA | ATT | CAT | AGT | GGG | CTT | AGT | AAT | GTT | 2181 |
| Ser<br>110 | Ala | Arg | Thr | Ser | Trp<br>115 | Lys | Glu | Ile | His | Ser<br>120 | Gly | Leu | Ser | Asn | Val<br>125 | |
| TTG | AGA | GCG | GGG | GTA | ACG | CCT | ATT | GTT | GCT | CAT | ATT | GAG | CGC | TAT | GAT | 2229 |
| Leu | Arg | Ala | Gly | Val<br>130 | Thr | Pro | Ile | Val | Ala<br>135 | His | Ile | Glu | Arg | Tyr<br>140 | Asp | |
| GCC | CTC | GAA | GAA | AAT | GCT | GAC | CGT | GTT | CGA | GAA | ATC | ATC | AAT | ATG | GGC | 2277 |
| Ala | Leu | Glu | Glu<br>145 | Asn | Ala | Asp | Arg | Val<br>150 | Arg | Glu | Ile | Ile | Asn<br>155 | Met | Gly | |
| TGC | TAT | ACT | CAA | GTC | AAT | AGC | TCA | CAT | GTC | CTC | AAA | CCA | AAG | CTC | TTT | 2325 |
| Cys | Tyr | Thr<br>160 | Gln | Val | Asn | Ser | Ser<br>165 | His | Val | Leu | Lys | Pro<br>170 | Lys | Leu | Phe | |
| GGA | GAT | AAA | GAT | AAA | GTA | AGA | AAG | AAA | CGT | GTT | CGC | TTT | TTC | TTG | GAG | 2373 |
| Gly | Asp<br>175 | Lys | Asp | Lys | Val | Arg<br>180 | Lys | Lys | Arg | Val | Arg<br>185 | Phe | Phe | Leu | Glu | |
| AAA | AAT | TTG | GTT | CAT | ATG | GTT | GCT | AGC | GAC | ATG | CAT | AAT | CTT | GGG | CCG | 2421 |
| Lys<br>190 | Asn | Leu | Val | His | Met<br>195 | Val | Ala | Ser | Asp | Met<br>200 | His | Asn | Leu | Gly | Pro<br>205 | |
| AGA | CCA | CCA | TTT | ATG | AAA | GAT | GCT | TAT | GAA | ATT | GTT | AAA | AAG | AAC | TAC | 2469 |
| Arg | Pro | Pro | Phe | Met<br>210 | Lys | Asp | Ala | Tyr | Glu<br>215 | Ile | Val | Lys | Lys | Asn<br>220 | Tyr | |
| GGC | TCC | AAA | CGT | GCT | AAG | AAT | CTT | TTT | ATT | GAA | AAT | CCC | AAA | ACA | TTA | 2517 |
| Gly | Ser | Lys | Arg<br>225 | Ala | Lys | Asn | Leu | Phe<br>230 | Ile | Glu | Asn | Pro | Lys<br>235 | Thr | Leu | |
| CTA | GAA | AAT | CAA | TAT | TTA | TAGGAGATAT T | | ATG | AAT | CAA | GAT | AAC | ACT | AAA | | 2567 |
| Leu | Glu | Asn<br>240 | Gln | Tyr | Leu | | | Met<br>1 | Asn | Gln | Asp | Asn | Thr | Lys<br>5 | | |
| AGT | GAT | GAA | ATC | GAC | GTA | CTA | GCA | TTG | CTA | CAT | AAA | CTT | TGG | ACG | AAG | 2615 |
| Ser | Asp | Glu<br>10 | Ile | Asp | Val | Leu<br>15 | Ala | Leu | Leu | His | Lys<br>20 | Leu | Trp | Thr | Lys | |
| AAG | CTT | TTG | ATT | CTT | TTC | ACA | GCT | TTT | TAT | TTC | GCT | GTT | TTC | AGT | TTC | 2663 |
| Lys | Leu<br>25 | Leu | Ile | Leu | Phe<br>30 | Thr | Ala | Phe | Tyr | Phe<br>35 | Ala | Val | Phe | Ser | Phe | |
| TTA | GGT | ACT | TAT | TTC | TTT | ATC | CAA | CCA | ACA | TAT | ACA | TCA | ACA | ACG | CGT | 2711 |
| Leu<br>40 | Gly | Thr | Tyr | Phe | Phe<br>45 | Ile | Gln | Pro | Thr | Tyr<br>50 | Thr | Ser | Thr | Thr | Arg<br>55 | |
| ATC | TAT | GTT | GTT | AAT | CAG | GCA | ACA | GAT | AAT | AAG | AAT | CTT | TCT | GCT | CAA | 2759 |
| Ile | Tyr | Val | Val | Asn<br>60 | Gln | Ala | Thr | Asp | Asn<br>65 | Lys | Asn | Leu | Ser | Ala<br>70 | Gln | |
| GAT | TTG | CAA | GCT | GGT | ACC | TAT | TTG | GCA | AAT | GAC | TAT | AAA | GAG | ATT | ATT | 2807 |
| Asp | Leu | Gln | Ala<br>75 | Gly | Thr | Tyr | Leu | Ala<br>80 | Asn | Asp | Tyr | Lys | Glu<br>85 | Ile | Ile | |
| GCA | TCA | AAT | GAT | GTA | TTA | TCA | GAA | GTT | ATT | AAA | GAT | GAA | AAA | TTG | AAT | 2855 |
| Ala | Ser | Asn<br>90 | Asp | Val | Leu | Ser | Glu<br>95 | Val | Ile | Lys | Asp | Glu<br>100 | Lys | Leu | Asn | |
| TTG | AGT | GAG | GCA | GAA | CTG | TCT | AAA | ATG | GTT | TCA | GTT | AAT | ATT | CCT | ACT | 2903 |
| Leu | Ser<br>105 | Glu | Ala | Glu | Leu | Ser<br>110 | Lys | Met | Val | Ser | Val<br>115 | Asn | Ile | Pro | Thr | |
| GAT | ACT | CGT | CTT | ATT | TCA | ATT | TCT | GTT | AAT | GCT | AAA | ACT | GGT | CAA | GAT | 2951 |
| Asp | Thr | Arg<br>120 | Leu | Ile | Ser | Ile | Ser<br>125 | Val | Asn | Ala | Lys | Thr<br>130 | Gly | Gln | Asp<br>135 | |

| | | | | | | | | | | | | | | | | |
|---|---|---|---|---|---|---|---|---|---|---|---|---|---|---|---|---|
| GCG | CAA | ACA | CTT | GCC | AAT | AAG | GTT | CGT | GAA | GTT | GCT | TCA | AAA | AAA | ATC | 2999 |
| Ala | Gln | Thr | Leu | Ala | Asn | Lys | Val | Arg | Glu | Val | Ala | Ser | Lys | Lys | Ile | |
| | | | 140 | | | | 145 | | | | | | 150 | | | |
| AAG | AAG | GTG | ACA | AAA | GTT | GAA | GAT | GTC | ACA | ACG | CTC | GAA | GAA | GCT | AAA | 3047 |
| Lys | Lys | Val | Thr | Lys | Val | Glu | Asp | Val | Thr | Thr | Leu | Glu | Glu | Ala | Lys | |
| | | | 155 | | | | 160 | | | | | | 165 | | | |
| TTG | CCA | GAG | TCA | CCA | TCT | TCA | CCA | AAT | ATC | AAA | CTT | AAT | GTG | CTT | CTT | 3095 |
| Leu | Pro | Glu | Ser | Pro | Ser | Ser | Pro | Asn | Ile | Lys | Leu | Asn | Val | Leu | Leu | |
| | | | 170 | | | | 175 | | | | | | 180 | | | |
| GGG | GCA | GTG | CTT | GGA | GGA | TTC | CTT | GCA | GTG | GTT | GGT | GTA | TTG | GTA | CGT | 3143 |
| Gly | Ala | Val | Leu | Gly | Gly | Phe | Leu | Ala | Val | Val | Gly | Val | Leu | Val | Arg | |
| | | | 185 | | | | 190 | | | | | | 195 | | | |
| GAA | ATC | CTA | GAT | GAT | CGT | GTT | CGC | CGT | CCA | GAA | GAT | GTG | GAA | GAT | GCC | 3191 |
| Glu | Ile | Leu | Asp | Asp | Arg | Val | Arg | Arg | Pro | Glu | Asp | Val | Glu | Asp | Ala | |
| 200 | | | | | 205 | | | | 210 | | | | | | 215 | |
| CTT | GGA | ATG | ACA | CTT | CTT | GGA | ATT | GTC | CCT | GAT | ACA | GAT | AAA | ATT | TAA | 3239 |
| Leu | Gly | Met | Thr | Leu | Leu | Gly | Ile | Val | Pro | Asp | Thr | Asp | Lys | Ile | * | |
| | | | 220 | | | | 225 | | | | | | 230 | | | |
| GGAGAAGAA | ATG | CCT | TTA | TTA | AAG | TTA | GTT | AAA | TCA | AAA | GTA | GAC | TTT | | | 3287 |
| | Met | Pro | Leu | Leu | Lys | Leu | Val | Lys | Ser | Lys | Val | Asp | Phe | | | |
| | 1 | | | | 5 | | | | | | 10 | | | | | |
| GCT | AAA | AAG | ACG | GAA | GAG | TAT | TAT | AAC | GCT | ATT | CGC | ACA | AAT | ATT | CAA | 3335 |
| Ala | Lys | Lys | Thr | Glu | Glu | Tyr | Tyr | Asn | Ala | Ile | Arg | Thr | Asn | Ile | Gln | |
| | 15 | | | | | 20 | | | | 25 | | | | | | |
| TTT | TCT | GGT | GCT | CAG | ATG | AAA | GTG | ATT | GCG | ATT | AGC | TCT | GTT | GAA | GCT | 3383 |
| Phe | Ser | Gly | Ala | Gln | Met | Lys | Val | Ile | Ala | Ile | Ser | Ser | Val | Glu | Ala | |
| 30 | | | | | 35 | | | | 40 | | | | | | 45 | |
| GGT | GAA | GGA | AAA | TCA | ATG | ATA | TCT | GTT | AAC | TTG | GCG | ATT | TCA | TTT | GCT | 3431 |
| Gly | Glu | Gly | Lys | Ser | Met | Ile | Ser | Val | Asn | Leu | Ala | Ile | Ser | Phe | Ala | |
| | | | | 50 | | | | 55 | | | | | 60 | | | |
| AGT | GTT | GGG | CTC | CGA | ACA | CTT | CTG | ATT | GAT | GCG | GAA | ACG | CGT | AAT | TCT | 3479 |
| Ser | Val | Gly | Leu | Arg | Thr | Leu | Leu | Ile | Asp | Ala | Glu | Thr | Arg | Asn | Ser | |
| | | | 65 | | | | 70 | | | | | 75 | | | | |
| GTT | TTG | TCA | GGT | ACA | TTT | AAA | TCA | AAT | GAG | CCT | TAT | AAA | GGT | CTT | TCA | 3527 |
| Val | Leu | Ser | Gly | Thr | Phe | Lys | Ser | Asn | Glu | Pro | Tyr | Lys | Gly | Leu | Ser | |
| | | 80 | | | | | 85 | | | | | 90 | | | | |
| AAT | TTC | CTT | TCA | GGA | AAT | GCC | GAT | CTA | AAT | GAA | ACG | ATT | TGC | CAA | ACT | 3575 |
| Asn | Phe | Leu | Ser | Gly | Asn | Ala | Asp | Leu | Asn | Glu | Thr | Ile | Cys | Gln | Thr | |
| | 95 | | | | | 100 | | | | | 105 | | | | | |
| GAT | ATT | TCT | GGT | TTA | GAT | GTT | ATT | GCA | TCT | GGT | CCT | GTT | CCA | CCT | AAT | 3623 |
| Asp | Ile | Ser | Gly | Leu | Asp | Val | Ile | Ala | Ser | Gly | Pro | Val | Pro | Pro | Asn | |
| 110 | | | | | 115 | | | | 120 | | | | | | 125 | |
| CCA | ACA | AGT | CTT | TTG | CAA | AAT | GAT | AAT | TTT | AGA | CAT | TTG | ATG | GAA | GTT | 3671 |
| Pro | Thr | Ser | Leu | Leu | Gln | Asn | Asp | Asn | Phe | Arg | His | Leu | Met | Glu | Val | |
| | | | | 130 | | | | | 135 | | | | | 140 | | |
| GCT | CGT | AGT | TGT | TAT | GAT | TAT | GTC | ATC | ATC | GAT | ACA | CCA | CCA | GTT | GGT | 3719 |
| Ala | Arg | Ser | Cys | Tyr | Asp | Tyr | Val | Ile | Ile | Asp | Thr | Pro | Pro | Val | Gly | |
| | | | 145 | | | | | 150 | | | | | 155 | | | |
| CTG | GTT | ATT | GAT | GCA | GTT | ATT | ATT | GCC | CAT | CAG | GCT | GAT | GCC | AGT | CTT | 3767 |
| Leu | Val | Ile | Asp | Ala | Val | Ile | Ile | Ala | His | Gln | Ala | Asp | Ala | Ser | Leu | |
| | | | 160 | | | | | 165 | | | | | 170 | | | |
| TTG | GTT | ACA | GAA | GCT | GGG | AAA | ATT | AAA | CGT | CGT | TTC | GTA | ACT | AAG | GCC | 3815 |
| Leu | Val | Thr | Glu | Ala | Gly | Lys | Ile | Lys | Arg | Arg | Phe | Val | Thr | Lys | Ala | |
| | | 175 | | | | | 180 | | | | | 185 | | | | |
| GTT | GAA | CAA | TTG | GTA | GAA | AGT | GGT | TCT | CAG | TTC | TTA | GGG | GTC | GTC | CTT | 3863 |
| Val | Glu | Gln | Leu | Val | Glu | Ser | Gly | Ser | Gln | Phe | Leu | Gly | Val | Val | Leu | |
| | 190 | | | | | 195 | | | | | 200 | | | | 205 | |
| AAT | AAA | GTT | GAC | ATG | ACA | GTT | GAT | AAA | TAT | GGA | TTT | TAT | GGT | TCT | TAC | 3911 |
| Asn | Lys | Val | Asp | Met | Thr | Val | Asp | Lys | Tyr | Gly | Phe | Tyr | Gly | Ser | Tyr | |
| | | | 210 | | | | | 215 | | | | | 220 | | | |

| | | | | | | | | | | | | | | | | |
|---|---|---|---|---|---|---|---|---|---|---|---|---|---|---|---|---|
| GGA | TCA | TAT | GGC | GAG | TAT | GGA | AAA | AAA | TCT | GAC | CAA | AAA | GAA | GGT | CAT | 3959 |
| Gly | Ser | Tyr | Gly | Glu | Tyr | Gly | Lys | Lys | Ser | Asp | Gln | Lys | Glu | Gly | His | |
| | | 225 | | | | | 230 | | | | | 235 | | | | |

| | | | | | | | | | | |
|---|---|---|---|---|---|---|---|---|---|---|
| TCA | AGA | GCA | CAT | CGT | CGT | AGA | AAA | GTC | GGT | TGG | AAT TAACGCGTTA | 4005 |
| Ser | Arg | Ala | His | Arg | Arg | Arg | Lys | Val | Gly | Trp | Asn |
| | | 240 | | | | | 245 | | | | |

GTGTGTTTTA AGATGTCGTT GGGAACGACA AGTGGAGGGA ATGAG ATG TCA CAA 4059
                                                  Met Ser Gln
                                                   1

| | | | | | | | | | | | | | | | |
|---|---|---|---|---|---|---|---|---|---|---|---|---|---|---|---|
| GCT | AAA | GAG | GAA | ATT | TCA | GAT | GTT | ATG | ACT | TAT | TCA | GAG | CTA | ACA | AGT | 4107 |
| Ala | Lys | Glu | Glu | Ile | Ser | Asp | Val | Met | Thr | Tyr | Ser | Glu | Leu | Thr | Ser |
| | 5 | | | | | 10 | | | | | 15 | | | | |

| CAT | AAG | CCC | AAA | ATT | ATT | TAT | AGC | TTG | ATT | AAG | CGG | ATT | GGT | GAT | ATT | 4155 |
| His | Lys | Pro | Lys | Ile | Ile | Tyr | Ser | Leu | Ile | Lys | Arg | Ile | Gly | Asp | Ile |
| 20 | | | | | 25 | | | | | 30 | | | | | 35 |

| TTG | GTT | AGT | TCT | ATT | GGT | TTA | ATT | ATT | TTG | ATA | CCG | CTA | TTT | TTG | ATA | 4203 |
| Leu | Val | Ser | Ser | Ile | Gly | Leu | Ile | Ile | Leu | Ile | Pro | Leu | Phe | Leu | Ile |
| | | | | 40 | | | | | 45 | | | | | 50 | |

| GTT | GCT | TTG | ATC | ATG | AAA | TGC | TCT | GAA | CCA | ACA | GCA | CCT | ATA | TTT | TTC | 4251 |
| Val | Ala | Leu | Ile | Met | Lys | Cys | Ser | Glu | Pro | Thr | Ala | Pro | Ile | Phe | Phe |
| | | | | 55 | | | | | 60 | | | | | 65 | |

| TCA | CAT | ATT | AGA | AAT | GGT | AAA | AAT | GGC | AAA | AAG | TTC | AAA | ATG | TAT | AAA | 4299 |
| Ser | His | Ile | Arg | Asn | Gly | Lys | Asn | Gly | Lys | Lys | Phe | Lys | Met | Tyr | Lys |
| | | 70 | | | | | 75 | | | | | 80 | | | |

| TTT | AGA | ACC | ATG | TGT | CAG | GAC | GCA | GAA | TCG | ATT | TTG | ATG | AAA | GAT | ACG | 4347 |
| Phe | Arg | Thr | Met | Cys | Gln | Asp | Ala | Glu | Ser | Ile | Leu | Met | Lys | Asp | Thr |
| | 85 | | | | | 90 | | | | | 95 | | | | |

| GAA | CTT | TTT | GCA | AAA | TTT | AAG | GCA | AAT | GGT | TAT | AAA | CTT | GAA | ACG | CAT | 4395 |
| Glu | Leu | Phe | Ala | Lys | Phe | Lys | Ala | Asn | Gly | Tyr | Lys | Leu | Glu | Thr | His |
| 100 | | | | | 105 | | | | | 110 | | | | | 115 |

| GAA | GAT | CCT | AGA | ATT | ACA | AAA | ATC | GGT | GGC | ATA | TTA | AGG | AAA | ACA | AGT | 4443 |
| Glu | Asp | Pro | Arg | Ile | Thr | Lys | Ile | Gly | Gly | Ile | Leu | Arg | Lys | Thr | Ser |
| | | | | 120 | | | | | 125 | | | | | 130 | |

| ATT | GAT | GAA | TTG | CCA | CAA | CTG | ATT | AAT | GTT | TTT | TTA | GGA | CAA | ATG | TCA | 4491 |
| Ile | Asp | Glu | Leu | Pro | Gln | Leu | Ile | Asn | Val | Phe | Leu | Gly | Gln | Met | Ser |
| | | | | 135 | | | | | 140 | | | | | 145 | |

| TTA | GTG | GGT | CCA | CGT | CCA | CTA | CCA | GAT | AGA | GAA | ATC | ATT | GAA | TAC | GGT | 4539 |
| Leu | Val | Gly | Pro | Arg | Pro | Leu | Pro | Asp | Arg | Glu | Ile | Ile | Glu | Tyr | Gly |
| | | 150 | | | | | 155 | | | | | 160 | | | |

| GAT | AAC | CAA | GAA | AAA | TTT | TTA | AGC | GTT | AAA | CCA | GGC | ATG | ACA | GGA | TGG | 4587 |
| Asp | Asn | Gln | Glu | Lys | Phe | Leu | Ser | Val | Lys | Pro | Gly | Met | Thr | Gly | Trp |
| 165 | | | | | 170 | | | | | 175 | | | | | |

| TGG | CAA | GTT | TCA | GGG | AGA | AGT | ACT | ATT | GGG | TAT | CCT | GAG | CGG | TGT | CAT | 4635 |
| Trp | Gln | Val | Ser | Gly | Arg | Ser | Thr | Ile | Gly | Tyr | Pro | Glu | Arg | Cys | His |
| 180 | | | | | 185 | | | | | 190 | | | | | 195 |

| CTT | GAG | CTT | TAT | TAT | GTA | GAA | AAG | TGT | TGT | TTT | ACT | TTC | GAT | GTT | CTT | 4683 |
| Leu | Glu | Leu | Tyr | Tyr | Val | Glu | Lys | Cys | Cys | Phe | Thr | Phe | Asp | Val | Leu |
| | | | | 200 | | | | | 205 | | | | | 210 | |

| ATA | TTA | CTT | AAG | ACA | ATT | GGG | ATT | GTT | TTG | AAG | AGA | GTT | GGA | GCG | CGT | 4731 |
| Ile | Leu | Leu | Lys | Thr | Ile | Gly | Ile | Val | Leu | Lys | Arg | Val | Gly | Ala | Arg |
| | | | | 215 | | | | | 220 | | | | | 225 | |

TAGTACTGAT GAAACAAAAA TTATTATTGA TAATAGAAGC GATGAGTGGT GGAGCCGGTC 4791

GTCATGTACA AGACTTGATT AGTCATCTAC CTCAAGAAAA ATTTGATATT TATGTGATTT 4851

ATTCAAATCA TAGAACAAAT CCTGTTTTTT GGAAAAAATA GTAACG ATG AAT GAG 4906
                                                    Met Asn Glu
                                                     1

| CAA | GTA | ACT | TTT | ATT | TTA | TGT | GAT | TTT | CTC | GTA | AGA | GAA | ATT | AAA | CCG | 4954 |
| Gln | Val | Thr | Phe | Ile | Leu | Cys | Asp | Phe | Leu | Val | Arg | Glu | Ile | Lys | Pro |
| | 5 | | | | | 10 | | | | | 15 | | | | |

```
AAA TAT GAT TTG CTT GCT TAT CAA TTT ATT TCT AAA AAG ATT AAA GAA         5002
Lys Tyr Asp Leu Leu Ala Tyr Gln Phe Ile Ser Lys Lys Ile Lys Glu
 20              25                  30                  35

ATC AAA CCA GAT ATT GTA CAT TGT CAC AGT TCA AAA GCT GGT GTT ATT         5050
Ile Lys Pro Asp Ile Val His Cys His Ser Ser Lys Ala Gly Val Ile
                 40                  45                  50

GGT CGT TTA GCT GCC AAA AGA CGA GGT GTT AAA AAA ATA TTT TAT ACG         5098
Gly Arg Leu Ala Ala Lys Arg Arg Gly Val Lys Lys Ile Phe Tyr Thr
             55                  60                  65

CCA CAT GCT TAT TCG TTT TTG GCA CCT GAA TTT AGT GGG AAG AAA AAG         5146
Pro His Ala Tyr Ser Phe Leu Ala Pro Glu Phe Ser Gly Lys Lys Lys
             70                  75                  80

TTT CTA TTT GTT CAA ATT GAA AAG TTT TTA AGC CGA TTT GCG ACA ACT         5194
Phe Leu Phe Val Gln Ile Glu Lys Phe Leu Ser Arg Phe Ala Thr Thr
         85                  90                  95

AAG ATA TTT TGT GTG TCA ATA GCG GAA ATG CAA GCT GCT CTT GAA GTA         5242
Lys Ile Phe Cys Val Ser Ile Ala Glu Met Gln Ala Ala Leu Glu Val
100                 105                 110                 115

AAT CTA GAT AAA ACC GAT AAG TTT CAG GTA ATT TAT AAT GGT TTG CCA         5290
Asn Leu Asp Lys Thr Asp Lys Phe Gln Val Ile Tyr Asn Gly Leu Pro
                120                 125                 130

GAA ATT GAT TTA CCA AGC AAA GAA ACG ATT CGG GCG CAA TTA GGA CTG         5338
Glu Ile Asp Leu Pro Ser Lys Glu Thr Ile Arg Ala Gln Leu Gly Leu
            135                 140                 145

GAA AAG GCA GCA GTT GTT ATA GGC AAT AAT GCA AAA ATG TCG GAA CAG         5386
Glu Lys Ala Ala Val Val Ile Gly Asn Asn Ala Lys Met Ser Glu Gln
        150                 155                 160

AAA AAT CCT ATG TTT TTT ATG GAA ATT GCC CGA AAA ATG ATT AGA CAA         5434
Lys Asn Pro Met Phe Phe Met Glu Ile Ala Arg Lys Met Ile Arg Gln
165                 170                 175

AAC GCA AAT TGG CAT TTT GTG TGG GTA GGT GAT GGT CAG CTG ATG CCA         5482
Asn Ala Asn Trp His Phe Val Trp Val Gly Asp Gly Gln Leu Met Pro
180                 185                 190                 195

CTT TTT CAA TCA TTT ATT AAG CAA AAT GGA CTA GAG GGA AAT ATC CAT         5530
Leu Phe Gln Ser Phe Ile Lys Gln Asn Gly Leu Glu Gly Asn Ile His
                200                 205                 210

TTG CTT GGC GAG CGT CCT GAT AGT GAA ATA GTT GTG ACA GCC TAT GAC         5578
Leu Leu Gly Glu Arg Pro Asp Ser Glu Ile Val Val Thr Ala Tyr Asp
            215                 220                 225

ATC TTC TTG ACG ACT TCC CAA TAT GAA GGT TTA CCT TAT GCA CCA ATT         5626
Ile Phe Leu Thr Thr Ser Gln Tyr Glu Gly Leu Pro Tyr Ala Pro Ile
        230                 235                 240

GAA GCG ATG CGA GCT GGT GTC CCG ATT CTT GCG ACA AAA GTT GTT GGC         5674
Glu Ala Met Arg Ala Gly Val Pro Ile Leu Ala Thr Lys Val Val Gly
245                 250                 255

AAT AGT GAG CTT GTG ATA GAG GGC AAA AAT GGT TAT TTG ATT GAC TTA         5722
Asn Ser Glu Leu Val Ile Glu Gly Lys Asn Gly Tyr Leu Ile Asp Leu
260                 265                 270                 275

GAG TGG TCA AAA TCT GTC GAA GAA AAA TTA TAT AAG GCA GCG AAA ATA         5770
Glu Trp Ser Lys Ser Val Glu Glu Lys Leu Tyr Lys Ala Ala Lys Ile
                280                 285                 290

GAT GCA CAA ATG ATT AAA GCA GAT TTT AGG CAA AGG TTT GCG ATT GAT         5818
Asp Ala Gln Met Ile Lys Ala Asp Phe Arg Gln Arg Phe Ala Ile Asp
            295                 300                 305

CAG ATA TTA AAG CAA ATT GAA ACA ATT TAT TTA GCT TGAATGAAGA              5864
Gln Ile Leu Lys Gln Ile Glu Thr Ile Tyr Leu Ala
        310                 315

ATGAGGAGGC ATAAATGCTG ATTTTGAAAT TAAAATTTCA TCTTAATTGG TACACAAACG       5924

AAAACCATTA TTACACGTGA GTATTCGAAG ACCTGGAAAC GAGGCGATGA GCCGTATTAT       5984
```

| | | | | | |
|---|---|---|---|---|---|
| CCAGTGAACA | ATGATCGTAA | CAACAAACTC | TATACTGCCT | ATAAGCGTCT | TGCCGAGCAA | 6044 |
| CAAGAGAATG | TCATTTTCGG | TGGACGTCTA | GGTCACTACC | GTTACTACGA | TATGCACCAG | 6104 |
| GTAATTGGAG | CTGCCTTGCA | GTGTGTCAGA | AATGAAGTGA | AGTAAATCTT | GATGAAGTTG | 6164 |
| AATAACTTTA | AGTAATTTTA | TACTTAATCC | AATTGATGAA | ATATTTTTG | TATCGATTTA | 6224 |
| TCTTCTGTAA | GAAGAGTCCT | AATCGTTTAA | AAAATGTACA | ATTGAGTTTT | TATATTTTA | 6284 |
| AATAAAGTTA | CTTTTAAGTC | GTGTTATAGA | ATATACATGA | ATAGGTGTAT | TAGAAAATTT | 6344 |
| ATTAATCTAA | TCCTCGAAAA | TAACTGACTG | TAAGGAATCA | AGTTGTGGAG | TGTAAGTTGT | 6404 |
| CAAATGGAGA | GGAAAATAAT | ATG AAA AAA ATT TCA ATT TTA CAC TTT TCC | | | 6454 |
| | | Met Lys Lys Ile Ser Ile Leu His Phe Ser | | | |
| | | 1        5              10 | | | |

| | | | | | | | | | | |
|---|---|---|---|---|---|---|---|---|---|---|
| CAA | GTA | TCA | GGC | GGG | GGA | GTT | GAA | AAG | TAC | ATA | AAA | TTA | TTT | TTA | AAG | 6502 |
| Gln | Val | Ser | Gly | Gly | Gly | Val | Glu | Lys | Tyr | Ile | Lys | Leu | Phe | Leu | Lys | |
| | | | | 15 | | | | 20 | | | | | 25 | | | |

| TAT TCT GAT GTG ACA AAA TTT AAT AAT TAT TTA GTT GCA CCT AAT CTT | 6550 |
|---|---|
| Tyr Ser Asp Val Thr Lys Phe Asn Asn Tyr Leu Val Ala Pro Asn Leu | |
|           30              35              40 | |

| GAA AAT TAT GAC GAA TTT AAT GGA TAT TTA AAG ATG TCT GTC AAT TTT | 6598 |
|---|---|
| Glu Asn Tyr Asp Glu Phe Asn Gly Tyr Leu Lys Met Ser Val Asn Phe | |
|       45              50              55 | |

| AAT ATG GAA CAA ACT TTT TCT CCG CTA AAA ATA TTC AAA AAT GTC TTT | 6646 |
|---|---|
| Asn Met Glu Gln Thr Phe Ser Pro Leu Lys Ile Phe Lys Asn Val Phe | |
|   60              65              70 | |

| TTT ATT CGT AGT GTA CTC AAA AAA ATA AAC CCA GAT ATA GTA TAC CTA | 6694 |
|---|---|
| Phe Ile Arg Ser Val Leu Lys Lys Ile Asn Pro Asp Ile Val Tyr Leu | |
| 75              80              85              90 | |

| CAT AGT ACA TTT GCA GGT GTC GTA GGT CGT ATT GCT TCA ATA GGT TTG | 6742 |
|---|---|
| His Ser Thr Phe Ala Gly Val Val Gly Arg Ile Ala Ser Ile Gly Leu | |
|           95              100             105 | |

| CCA ACA AAA GTA GTA TAC AAT CCT CAC GGA TGG TCC TTC AAA ATG GAC | 6790 |
|---|---|
| Pro Thr Lys Val Val Tyr Asn Pro His Gly Trp Ser Phe Lys Met Asp | |
|       110             115             120 | |

| AAC AGC TAT TTG AAA AAG CTT ATT TTT AAA TTA ATC GAA TTT TCT TTA | 6838 |
|---|---|
| Asn Ser Tyr Leu Lys Lys Leu Ile Phe Lys Leu Ile Glu Phe Ser Leu | |
|   125             130             135 | |

| TCT TTT TTA ACT GAT AAG TTT ATT TTA ATT TCG GAA TCT GAG TAT ATT | 6886 |
|---|---|
| Ser Phe Leu Thr Asp Lys Phe Ile Leu Ile Ser Glu Ser Glu Tyr Ile | |
| 140             145             150 | |

| TTG GCT AAC CAT ATT TCA TTT AAT AAA AGC AAG TTT TCA CTA ATT AAT | 6934 |
|---|---|
| Leu Ala Asn His Ile Ser Phe Asn Lys Ser Lys Phe Ser Leu Ile Asn | |
| 155             160             165             170 | |

| AAT GGT GTT GAA GTG ATT ACA GGG GAT TCA AGA AAT GAG ATA GAA GAG | 6982 |
|---|---|
| Asn Gly Val Glu Val Ile Thr Gly Asp Ser Arg Asn Glu Ile Glu Glu | |
|           175             180             185 | |

| ATA TTT CCA AAT GAG GAT TTT ATA ATT GGC ATG GTT GGC AGA CTA AGC | 7030 |
|---|---|
| Ile Phe Pro Asn Glu Asp Phe Ile Ile Gly Met Val Gly Arg Leu Ser | |
|       190             195             200 | |

| CCA CCC AAA GAG TTT TTC TTT TTT ATT GAT TTT GCA AAA AAA ATA TTA | 7078 |
|---|---|
| Pro Pro Lys Glu Phe Phe Phe Phe Ile Asp Phe Ala Lys Lys Ile Leu | |
|   205             210             215 | |

| CAA ATT CGA AAC GAT ACC AAT TTT ATT ATC GTG GGT GAT GGA GAG TTA | 7126 |
|---|---|
| Gln Ile Arg Asn Asp Thr Asn Phe Ile Ile Val Gly Asp Gly Glu Leu | |
| 220             225             230 | |

| CGA AGT GAA ATA GAA AGA ATG ATA CTA GAT AAT GGG TTA GGA GAT AAA | 7174 |
|---|---|
| Arg Ser Glu Ile Glu Arg Met Ile Leu Asp Asn Gly Leu Gly Asp Lys | |
| 235             240             245             250 | |

| ATC TAT ATT ACT GGG TGG GTT GAT AAT CCG AGA AAC TAT ATA GAG AAG | 7222 |
|---|---|
| Ile Tyr Ile Thr Gly Trp Val Asp Asn Pro Arg Asn Tyr Ile Glu Lys | |

```
                    255                      260                              265
TTT GAT CAA GCT ATT CTG TTT TCT AGA TGG GAG GGT CTT AGC CTA ACG       7270
Phe Asp Gln Ala Ile Leu Phe Ser Arg Trp Glu Gly Leu Ser Leu Thr
                270                     275                 280

ATT GCG GAA TAT ATG TCT CAG AAG AAA ACA ATT TTA GCA ACA AAT ATT       7318
Ile Ala Glu Tyr Met Ser Gln Lys Lys Thr Ile Leu Ala Thr Asn Ile
            285                     290                 295

GGT GGC ATT AAT GAT TTA ATC ACT GAT GGT GAA ACA GGA ATG CTG ATT       7366
Gly Gly Ile Asn Asp Leu Ile Thr Asp Gly Glu Thr Gly Met Leu Ile
        300                     305                 310

GAA GTT GGA GAC TTG AAT TCA GCA GTA TCT AAA TCT TTC GAG CTA AGA       7414
Glu Val Gly Asp Leu Asn Ser Ala Val Ser Lys Ser Phe Glu Leu Arg
315                 320                 325                 330

AAT AAT AAA GAG GTT TCG AAT CAA TTA GCG AAT AAC GCT TAT AAT AAA       7462
Asn Asn Lys Glu Val Ser Asn Gln Leu Ala Asn Asn Ala Tyr Asn Lys
                335                 340                 345

GTT GTT GAA CAG TTT TCG ATT GAA AAA CAG ATG GCT GAG ATA GAA AGT       7510
Val Val Glu Gln Phe Ser Ile Glu Lys Gln Met Ala Glu Ile Glu Ser
            350                 355                 360

TTA TTT ATA GAG ATG TGT AAC AAT GAG AAA TAGAGACTTA AAGAAAATAC         7560
Leu Phe Ile Glu Met Cys Asn Asn Glu Lys
        365                 370

AGGTTATTTG ATTGACTTAG AGTGGTCAAA ATCTGTCGAA GAAAAATTAT ATAAGGCAGC     7620

GAAAATGGAT GCACAAATGA TTAAAGCAGA TTTTAGGCAA AGGTTTGCGA TTGATCAGAT     7680

GTTAAAGCAA ATTAAAACAA TTTATTTAGC TTGAATGAAG AAAGAGGAGG CATAA ATG      7738
                                                                 Met
                                                                  1

CTG ATT TTG AAA TTA AAA TTT CAT CTT AAA TCG TTA TTC CTT AAA TGG       7786
Leu Ile Leu Lys Leu Lys Phe His Leu Lys Ser Leu Phe Leu Lys Trp
          5                  10                  15

ATT TAT CGA TTA CTT TAT CTA AAA AAG TTT CAG TTT GGT GCA CGC TTG       7834
Ile Tyr Arg Leu Leu Tyr Leu Lys Lys Phe Gln Phe Gly Ala Arg Leu
         20                  25                  30

ACG TTT CGA GAT GGG TTT CAT TTG TTA ATT GAA AAA TCT GGG AAA GTT       7882
Thr Phe Arg Asp Gly Phe His Leu Leu Ile Glu Lys Ser Gly Lys Val
     35                  40                  45

ATC ATC GGG AAT CAT GTT TTT TTT AAT AAC TTT TGT TCA ATT AAT GCC       7930
Ile Ile Gly Asn His Val Phe Phe Asn Asn Phe Cys Ser Ile Asn Ala
 50                  55                  60                  65

ATG TTA TCA GTA ACG ATT GGT GAT GAC TGT ATT TTT GGT GAA AAC GTT       7978
Met Leu Ser Val Thr Ile Gly Asp Asp Cys Ile Phe Gly Glu Asn Val
                 70                  75                  80

AAA ATT TAT GAT CAC AAT CAT TGT TAT CAA AAT AAA AGT CAA CCT ATT       8026
Lys Ile Tyr Asp His Asn His Cys Tyr Gln Asn Lys Ser Gln Pro Ile
             85                  90                  95

TCA AAA CAA GGT TTT TCA ACT GCT GCT ATC CAG ATT GGT CGT AAC TGT       8074
Ser Lys Gln Gly Phe Ser Thr Ala Ala Ile Gln Ile Gly Arg Asn Cys
         100                 105                 110

TGG ATA GGT AGT CAA GTG ACG ATT TTA AAA GGT GTA ACC ATA GGT GAT       8122
Trp Ile Gly Ser Gln Val Thr Ile Leu Lys Gly Val Thr Ile Gly Asp
     115                 120                 125

AAT AGT ATC ATT GGT GCT GGT GTG GTA GTT TAT CAA GAT GTG CCA GAA       8170
Asn Ser Ile Ile Gly Ala Gly Val Val Val Tyr Gln Asp Val Pro Glu
130                 135                 140                 145

AAT TCG ATT GTT TTA TCT AAT GGA GAA ATT AGA AAG CGT GGC                8212
Asn Ser Ile Val Leu Ser Asn Gly Glu Ile Arg Lys Arg Gly
            150                 155

TAATTAAA ATG TAT CTT AAA AGT CTA ATC TCT ATT GTT ATT CCA GTA TAT      8262
         Met Tyr Leu Lys Ser Leu Ile Ser Ile Val Ile Pro Val Tyr
```

|   |   |   |   |   |   |   |   |   |   |   |   |   |   |   |   |
|---|---|---|---|---|---|---|---|---|---|---|---|---|---|---|---|
| | 1 | | | | 5 | | | | | 10 | | | | | |
| AAT | GTA | GAG | AAA | TAT | TTA | GAA | AAA | TGT | TTG | CAA | TCT | GTT | CAA | AAT | CAG | 8310
| Asn | Val | Glu | Lys | Tyr | Leu | Glu | Lys | Cys | Leu | Gln | Ser | Val | Gln | Asn | Gln |
| 15 | | | | 20 | | | | | 25 | | | | | 30 | |
| ACT | TAC | AAT | AAT | TTT | GAA | GTG | ATT | TTA | GTG | AAT | GAT | GGC | TCA | ACC | GAT | 8358
| Thr | Tyr | Asn | Asn | Phe | Glu | Val | Ile | Leu | Val | Asn | Asp | Gly | Ser | Thr | Asp |
| | | | | 35 | | | | | 40 | | | | | 45 | |
| TCA | TCA | CTT | TCA | ATA | TGC | GAA | AAA | TTT | GTT | AAT | CAG | GAT | AAA | AGA | TTT | 8406
| Ser | Ser | Leu | Ser | Ile | Cys | Glu | Lys | Phe | Val | Asn | Gln | Asp | Lys | Arg | Phe |
| | | | 50 | | | | | 55 | | | | | 60 | | |
| TCT | GTT | TTT | TCT | AAA | GAA | AAT | GGT | GGT | ATG | TCA | TCT | GCA | CGA | AAT | TTT | 8454
| Ser | Val | Phe | Ser | Lys | Glu | Asn | Gly | Gly | Met | Ser | Ser | Ala | Arg | Asn | Phe |
| | | 65 | | | | | 70 | | | | | 75 | | | |
| GGA | ATT | AAA | AAG | GCT | AAA | GGA | TCG | TTT | ATC | ACA | TTT | GTA | GAT | AGT | GAT | 8502
| Gly | Ile | Lys | Lys | Ala | Lys | Gly | Ser | Phe | Ile | Thr | Phe | Val | Asp | Ser | Asp |
| | 80 | | | | | 85 | | | | | 90 | | | | |
| GAC | TAC | ATA | GTA | AAA | GAT | TAT | CTT | TCT | CAT | TTG | GTA | GCT | GGG | ATA | AAA | 8550
| Asp | Tyr | Ile | Val | Lys | Asp | Tyr | Leu | Ser | His | Leu | Val | Ala | Gly | Ile | Lys |
| 95 | | | | | 100 | | | | | 105 | | | | | 110 |
| AGT | GAG | ACC | TCT | ATA | GTT | TGT | TCA | AAG | TTT | TTT | CTT | GTA | GAT | GAA | AAA | 8598
| Ser | Glu | Thr | Ser | Ile | Val | Cys | Ser | Lys | Phe | Phe | Leu | Val | Asp | Glu | Lys |
| | | | | 115 | | | | | 120 | | | | | 125 | |
| GGA | AGT | TTA | TTG | ACT | AAA | AAA | GAG | GCA | CCT | AAA | AAG | AAA | TCA | GAA | GTC | 8646
| Gly | Ser | Leu | Leu | Thr | Lys | Lys | Glu | Ala | Pro | Lys | Lys | Lys | Ser | Glu | Val |
| | | | 130 | | | | | 135 | | | | | 140 | | |
| GTT | TCA | ATT | GAG | GAA | AGT | ATT | AAA | ATT | CTT | CTG | TTG | CAA | CAA | AAT | GGC | 8694
| Val | Ser | Ile | Glu | Glu | Ser | Ile | Lys | Ile | Leu | Leu | Leu | Gln | Gln | Asn | Gly |
| | | 145 | | | | | 150 | | | | | 155 | | | |
| TAT | GAT | CTC | GCT | GTC | TGG | GGA | AAA | TTA | TAC | CCC | GTT | TCT | TTC | TTT | GAA | 8742
| Tyr | Asp | Leu | Ala | Val | Trp | Gly | Lys | Leu | Tyr | Pro | Val | Ser | Phe | Phe | Glu |
| | 160 | | | | | 165 | | | | | 170 | | | | |
| ACA | ATT | TCT | TTC | CCA | GAA | GGA | AAA | CTT | TAC | GAA | GAT | ATG | GGA | ACA | ACT | 8790
| Thr | Ile | Ser | Phe | Pro | Glu | Gly | Lys | Leu | Tyr | Glu | Asp | Met | Gly | Thr | Thr |
| 175 | | | | | 180 | | | | | 185 | | | | | 190 |
| TAC | AAA | TTA | CTA | AAA | TTG | GCA | AGT | GAA | GTG | GTC | TTC | TTG | GAT | GCG | TAT | 8838
| Tyr | Lys | Leu | Leu | Lys | Leu | Ala | Ser | Glu | Val | Val | Phe | Leu | Asp | Ala | Tyr |
| | | | | 195 | | | | | 200 | | | | | 205 | |
| GAT | TAT | GCC | TAC | GTA | CAG | CGA | CCT | AAT | AGT | ATC | ATG | AAT | AGT | TCT | TTT | 8886
| Asp | Tyr | Ala | Tyr | Val | Gln | Arg | Pro | Asn | Ser | Ile | Met | Asn | Ser | Ser | Phe |
| | | | 210 | | | | | 215 | | | | | 220 | | |
| AAT | TTG | AAA | AAG | TTG | GAT | ATA | ATA | GAA | ATG | GTT | CAT | GAA | ATG | GAA | AAC | 8934
| Asn | Leu | Lys | Lys | Leu | Asp | Ile | Ile | Glu | Met | Val | His | Glu | Met | Glu | Asn |
| | | 225 | | | | | 230 | | | | | 235 | | | |
| GAT | ATA | TTA | GCA | CAG | TTT | CCA | AAT | TTA | GCA | TTA | TAT | GTT | AAG | AAT | CGA | 8982
| Asp | Ile | Leu | Ala | Gln | Phe | Pro | Asn | Leu | Ala | Leu | Tyr | Val | Lys | Asn | Arg |
| | 240 | | | | | 245 | | | | | 250 | | | | |
| GCA | TTT | GCC | GCG | GAA | GTG | AAA | ATC | TTT | TTA | GAG | ATT | CCA | AAA | GAA | AAA | 9030
| Ala | Phe | Ala | Ala | Glu | Val | Lys | Ile | Phe | Leu | Glu | Ile | Pro | Lys | Glu | Lys |
| 255 | | | | | 260 | | | | | 265 | | | | | 270 |
| GAA | TTT | GAG | CAA | GCG | CAA | AAG | CAA | CTT | TGG | CAT | GAT | ATC | AAA | AAG | AAT | 9078
| Glu | Phe | Glu | Gln | Ala | Gln | Lys | Gln | Leu | Trp | His | Asp | Ile | Lys | Lys | Asn |
| | | | | 275 | | | | | 280 | | | | | 285 | |
| AGA | AAA | GCA | CCA | TTT | ATG | ACA | AAA | GGT | GCT | AGA | TTG | AAG | AAT | AGG | CTC | 9126
| Arg | Lys | Ala | Pro | Phe | Met | Thr | Lys | Gly | Ala | Arg | Leu | Lys | Asn | Arg | Leu |
| | | | 290 | | | | | 295 | | | | | 300 | | |
| GGA | GCT | AGT | CTG | TCG | TTT | TTA | GGT | AAA | TCT | TTA | TTT | TTG | ACT | ATT | GGG | 9174
| Gly | Ala | Ser | Leu | Ser | Phe | Leu | Gly | Lys | Ser | Leu | Phe | Leu | Thr | Ile | Gly |
| | | 305 | | | | | 310 | | | | | 315 | | | |
| AAG | CAG | TTA | GTA | GAT | AGA | TAATGATATT | GAAAGCGATA | CGATACAATC | | | | | | | 9222
| Lys | Gln | Leu | Val | Asp | Arg | | | | | | | | | | |

```
              320
GTAAACTTCT TTTGGTGTTG ACTAGGAGTT AGCTTGAAAT TTGAATATAA AGGAAGCAAC                9282

AC ATG GTA ATT TAT TTT TTA CTT TTC CCG ATG ATC GCA ATG ATT TAT                   9329
   Met Val Ile Tyr Phe Leu Leu Phe Pro Met Ile Ala Met Ile Tyr
   1               5                   10                  15

TTA ATG ACA TTG CTC TTA CGG CAA AAA GCA CAA ATC CAA AAA ACG ATT                  9377
Leu Met Thr Leu Leu Leu Arg Gln Lys Ala Gln Ile Gln Lys Thr Ile
                20                  25                  30

TTT TGT GTT CTT ACG TTT GGT ACA CTA GGC TTT ATT TCA GCA AGT CGT                  9425
Phe Cys Val Leu Thr Phe Gly Thr Leu Gly Phe Ile Ser Ala Ser Arg
            35                  40                  45

GCA TCA AGT GTT GGG ACG GAC GTT ACT TTA TAC GAA AAT ATT TTT AAA                  9473
Ala Ser Ser Val Gly Thr Asp Val Thr Leu Tyr Glu Asn Ile Phe Lys
        50                  55                  60

TCT ATA AAT TAC GGG ATA AGT GCT GAG AAT AAT TGG GGA TAC GTC ATC                  9521
Ser Ile Asn Tyr Gly Ile Ser Ala Glu Asn Asn Trp Gly Tyr Val Ile
    65                  70                  75

TAT AAC AAG CTG ATT GGT AGT GTA TTT GGC TAT ACA GGA CAT GAA ATC                  9569
Tyr Asn Lys Leu Ile Gly Ser Val Phe Gly Tyr Thr Gly His Glu Ile
80                  85                  90                  95

ACG GCC GCT AAT TCA GTT TTG ATT ACA ATA CTT ATT GGT ATT TTT ATT                  9617
Thr Ala Ala Asn Ser Val Leu Ile Thr Ile Leu Ile Gly Ile Phe Ile
                100                 105                 110

TGG AAA GTA GCG GAA CAT TAT TTT GTT GCG ACG TTT TTA TAC ATT AGC                  9665
Trp Lys Val Ala Glu His Tyr Phe Val Ala Thr Phe Leu Tyr Ile Ser
            115                 120                 125

TTG TTT TAT TAT GCT ACA AGT TTT AAT ATT TCA AGA CAA TTT ATT GCC                  9713
Leu Phe Tyr Tyr Ala Thr Ser Phe Asn Ile Ser Arg Gln Phe Ile Ala
        130                 135                 140

ATG GGG CTT GTA TTG GTA GCA ATT TCT TTT GCT TTA GAT AAA AAG GTT                  9761
Met Gly Leu Val Leu Val Ala Ile Ser Phe Ala Leu Asp Lys Lys Val
    145                 150                 155

ATG CCT TGG TTT ATC TTG ACA GTT TTG GCT ACC TTA TTT CAT GCG ACA                  9809
Met Pro Trp Phe Ile Leu Thr Val Leu Ala Thr Leu Phe His Ala Thr
160                 165                 170                 175

GCA ATC GTT GCT TTT CCT GTC TAT TGG CTT ACA AAA GTA CAT TGG GAT                  9857
Ala Ile Val Ala Phe Pro Val Tyr Trp Leu Thr Lys Val His Trp Asp
                180                 185                 190

GTG AAA AAG ACA TTA AGT ATT TTT CCA ATC ACG ATT TTT GCA AGT TTT                  9905
Val Lys Lys Thr Leu Ser Ile Phe Pro Ile Thr Ile Phe Ala Ser Phe
            195                 200                 205

ATT TTT GAT GCT ATT TTA AAC ATT TTT GTA CGT TTT TTC CCA CAT TAT                  9953
Ile Phe Asp Ala Ile Leu Asn Ile Phe Val Arg Phe Phe Pro His Tyr
        210                 215                 220

GAG ATG TAT ATC ACT GGA ACA CAA TTT AAT ATT TCA GAT CAG GGG CAG                  10001
Glu Met Tyr Ile Thr Gly Thr Gln Phe Asn Ile Ser Asp Gln Gly Gln
    225                 230                 235

GGA CGT GTG GTT TTG GTC AAA ATA TTT ATC TTG CTC ATT TTG TTT ACT                  10049
Gly Arg Val Val Leu Val Lys Ile Phe Ile Leu Leu Ile Leu Phe Thr
240                 245                 250                 255

TTA TTC TTG TTT TAT AAA AAA AGC TAT GCT TTG ATT TCT GAA TGT CAT                  10097
Leu Phe Leu Phe Tyr Lys Lys Ser Tyr Ala Leu Ile Ser Glu Cys His
                260                 265                 270

CAA AGT TTG ATA GCT TTG ACA ACC GTT GGA TTA AGT ATC GGT ATT GTA                  10145
Gln Ser Leu Ile Ala Leu Thr Thr Val Gly Leu Ser Ile Gly Ile Val
            275                 280                 285

TTT TAT AAT AAT ATT TTA CTC AAT AGA ATA GAA ATG TTT TAT TCA ATT                  10193
Phe Tyr Asn Asn Ile Leu Leu Asn Arg Ile Glu Met Phe Tyr Ser Ile
        290                 295                 300
```

| | | | | | | | | | | | | | | | | |
|---|---|---|---|---|---|---|---|---|---|---|---|---|---|---|---|---|
| TTA | AGC | ATC | GTA | TTT | ATT | CCA | ATT | GCT | ATA | GAT | TAC | ATT | AGT | TTG | AAA | 10241 |
| Leu | Ser | Ile | Val | Phe | Ile | Pro | Ile | Ala | Ile | Asp | Tyr | Ile | Ser | Leu | Lys | |
| | 305 | | | | 310 | | | | | 315 | | | | | | |
| TTT | AAA | CAA | AAA | GAT | GCT | GTG | CGA | CTA | ATG | CTG | ACG | ATA | GGT | ATT | TTG | 10289 |
| Phe | Lys | Gln | Lys | Asp | Ala | Val | Arg | Leu | Met | Leu | Thr | Ile | Gly | Ile | Leu | |
| 320 | | | | | 325 | | | | | 330 | | | | | 335 | |
| TTA | ATT | ACA | CTT | GTG | CCT | TAC | TAT | ATA | CAG | GTT | AGC | GGT | AAT | TAT | TCA | 10337 |
| Leu | Ile | Thr | Leu | Val | Pro | Tyr | Tyr | Ile | Gln | Val | Ser | Gly | Asn | Tyr | Ser | |
| | | | | 340 | | | | | 345 | | | | | 350 | | |
| GGA | ATA | TTG | CCT | TAT | GTT | ATT | CAA | CAA | TAAAAAATAA | | AGTTTAGAGA | | | | | 10384 |
| Gly | Ile | Leu | Pro | Tyr | Val | Ile | Gln | Gln | | | | | | | | |
| | | | 355 | | | | | 360 | | | | | | | | |
| GGAAATA | ATG | GAG | GAT | AGA | AAG | AAA | CAA | GTA | ATT | TTG | ATA | CTA | TCC | CAC | | 10433 |
| | Met | Glu | Asp | Arg | Lys | Lys | Gln | Val | Ile | Leu | Ile | Leu | Ser | His | | |
| | 1 | | | | 5 | | | | | 10 | | | | | | |
| AGA | AAT | ACT | CTC | GCT | CTA | AAA | TCA | ACA | ATA | GAG | CTT | TTG | GAT | TCT | CAA | 10481 |
| Arg | Asn | Thr | Leu | Ala | Leu | Lys | Ser | Thr | Ile | Glu | Leu | Leu | Asp | Ser | Gln | |
| 15 | | | | | 20 | | | | | 25 | | | | | 30 | |
| TAC | TTT | GAT | TTC | TTT | CTT | CAT | ATA | GAT | AAA | AAA | AGT | AGA | ATT | CAA | GAT | 10529 |
| Tyr | Phe | Asp | Phe | Phe | Leu | His | Ile | Asp | Lys | Lys | Ser | Arg | Ile | Gln | Asp | |
| | | | | 35 | | | | | 40 | | | | | 45 | | |
| TTT | TTT | TAT | TTA | AAA | AAA | ATT | ACA | AAA | TTC | TCC | ACT | ATT | CAT | TTT | TCA | 10577 |
| Phe | Phe | Tyr | Leu | Lys | Lys | Ile | Thr | Lys | Phe | Ser | Thr | Ile | His | Phe | Ser | |
| | | | 50 | | | | | 55 | | | | | 60 | | | |
| GAA | AGA | AAA | AAT | GTA | CAT | TGG | GGA | GGT | TTT | TCT | ATG | GTA | GAA | GCA | ATG | 10625 |
| Glu | Arg | Lys | Asn | Val | His | Trp | Gly | Gly | Phe | Ser | Met | Val | Glu | Ala | Met | |
| | 65 | | | | 70 | | | | | 75 | | | | | | |
| TTT | GCG | CTA | TTA | GAA | TGT | GCA | CGT | GAT | ACA | GGA | GAA | TAT | TCT | TAT | TTT | 10673 |
| Phe | Ala | Leu | Leu | Glu | Cys | Ala | Arg | Asp | Thr | Gly | Glu | Tyr | Ser | Tyr | Phe | |
| 80 | | | | | 85 | | | | | 90 | | | | | | |
| CAT | TTT | TTA | TCT | GGA | GAT | GAT | ATG | CCA | ATC | AAA | GAT | AAT | GAA | ATA | GTA | 10721 |
| His | Phe | Leu | Ser | Gly | Asp | Asp | Met | Pro | Ile | Lys | Asp | Asn | Glu | Ile | Val | |
| 95 | | | | | 100 | | | | | 105 | | | | | 110 | |
| TTT | AAT | TTT | TTT | GAA | AAT | AGT | TAT | CCT | AAA | AAT | TTT | ATT | GAT | ATT | CTA | 10769 |
| Phe | Asn | Phe | Phe | Glu | Asn | Ser | Tyr | Pro | Lys | Asn | Phe | Ile | Asp | Ile | Leu | |
| | | | | 115 | | | | | 120 | | | | | 125 | | |
| GAT | TTT | GAA | AAT | GTC | AAT | AAA | AAT | TCA | TAT | TTC | TAC | GAA | CCC | CCT | GAG | 10817 |
| Asp | Phe | Glu | Asn | Val | Asn | Lys | Asn | Ser | Tyr | Phe | Tyr | Glu | Pro | Pro | Glu | |
| | | | 130 | | | | | 135 | | | | | 140 | | | |
| ATG | ATA | GAG | GAG | AGA | GTG | AAG | TAC | TAC | TAT | CCT | CAT | ATG | GAT | ATT | CTA | 10865 |
| Met | Ile | Glu | Glu | Arg | Val | Lys | Tyr | Tyr | Tyr | Pro | His | Met | Asp | Ile | Leu | |
| | | 145 | | | | | 150 | | | | | 155 | | | | |
| AAC | AGA | AAA | GGA | ACA | AAT | TTC | ATA | GGG | AAA | AAA | CTA | ATT | TAT | CTA | CAA | 10913 |
| Asn | Arg | Lys | Gly | Thr | Asn | Phe | Ile | Gly | Lys | Lys | Leu | Ile | Tyr | Leu | Gln | |
| | 160 | | | | | 165 | | | | | 170 | | | | | |
| AAA | TTG | TTG | AAA | GTT | AAT | CGC | TTG | AAA | AAT | AGA | GAG | ATA | GAA | ATT | TTC | 10961 |
| Lys | Leu | Leu | Lys | Val | Asn | Arg | Leu | Lys | Asn | Arg | Glu | Ile | Glu | Ile | Phe | |
| 175 | | | | | 180 | | | | | 185 | | | | | 190 | |
| AAG | GGT | CAT | CAA | TGG | TGT | AGT | TTG | ACA | AAT | CAA | TTT | GTA | GAT | ATT | TTA | 11009 |
| Lys | Gly | His | Gln | Trp | Cys | Ser | Leu | Thr | Asn | Gln | Phe | Val | Asp | Ile | Leu | |
| | | | | 195 | | | | | 200 | | | | | 205 | | |
| TTG | GAT | AAA | GAG | GAA | AGA | AGA | GTA | GGT | AAG | TCT | TAT | TTT | TCA | TCT | AGT | 11057 |
| Leu | Asp | Lys | Glu | Glu | Arg | Arg | Val | Gly | Lys | Ser | Tyr | Phe | Ser | Ser | Ser | |
| | | | 210 | | | | | 215 | | | | | 220 | | | |
| TTA | ATA | CCA | GAT | GAA | TGT | TAT | TTT | CAA | ACG | TTT | GCT | ATG | ATA | AAA | AAA | 11105 |
| Leu | Ile | Pro | Asp | Glu | Cys | Tyr | Phe | Gln | Thr | Phe | Ala | Met | Ile | Lys | Lys | |
| | | 225 | | | | | 230 | | | | | 235 | | | | |
| GTT | GAA | ATT | TAT | CAA | CAG | AAA | AAT | ATG | TCA | GCA | CGC | TTA | ATT | GAT | TGG | 11153 |
| Val | Glu | Ile | Tyr | Gln | Gln | Lys | Asn | Met | Ser | Ala | Arg | Leu | Ile | Asp | Trp | |
| 240 | | | | | 245 | | | | | 250 | | | | | | |

| | | | | | | | | | | | | | | | | |
|---|---|---|---|---|---|---|---|---|---|---|---|---|---|---|---|---|
| ACA | AGA | GGG | AAA | CCA | TAT | ATT | TGG | CGA | CAG | GAT | GAT | TTT | TTT | GAA | ATT | 11201 |
| Thr | Arg | Gly | Lys | Pro | Tyr | Ile | Trp | Arg | Gln | Asp | Asp | Phe | Phe | Glu | Ile | |
| 255 | | | | | 260 | | | | 265 | | | | | | 270 | |
| ATG | AAT | GAT | AAA | GAT | TCA | ATG | TTT | TCT | AGG | AAG | TTT | GAT | GAA | AAT | GTA | 11249 |
| Met | Asn | Asp | Lys | Asp | Ser | Met | Phe | Ser | Arg | Lys | Phe | Asp | Glu | Asn | Val | |
| | | | | 275 | | | | 280 | | | | | 285 | | | |
| GAT | CGT | AAA | ATA | ATT | GAA | GAA | ATT | TAT | ATA | AAA | ATA | AGA | GGA | AGA | AGT | 11297 |
| Asp | Arg | Lys | Ile | Ile | Glu | Glu | Ile | Tyr | Ile | Lys | Ile | Arg | Gly | Arg | Ser | |
| | | | 290 | | | | 295 | | | | | 300 | | | | |
| ACT | GAT | GAA | GCA | AAT | AAA | ATC | AAA | GAT | AAG | AGA | TTT | ACA | AAA | | | 11339 |
| Thr | Asp | Glu | Ala | Asn | Lys | Ile | Lys | Asp | Lys | Arg | Phe | Thr | Lys | | | |
| | | 305 | | | | | 310 | | | | | 315 | | | | |

| | | | | | |
|---|---|---|---|---|---|
| TAATTTTACC | TATGTTTTTG | GAAAGAAAAC | TTTTCTTGGA | AGGGGAGAAG | CGATTATCAT | 11399 |
| AGATGAACCT | GAGCATGGAA | ATTTGGGAGA | TCAAGCAATT | GCTTTTGCAG | AAAATCAATT | 11459 |
| TTAGTAAAT | CATGTATCAG | TACGAGATGT | AGAACATCTT | ATAGAAAGCA | AACTATTTC | 11519 |
| AGAAATAAAA | TCTATAAAAA | AAATATTGG | AAAAAAGAA | TTAGTTTTTT | TTCATGGGGG | 11579 |
| AGGAAATTTC | GGGACACTTT | ATCTAAAGTA | TGAGCGCATT | AGAAGATTGG | CAGTATCAAA | 11639 |
| GCTTCCCTTT | AATAAAATGA | TTCTATTTCC | TCAGTCAATT | TCATTTGAAG | ATAGTAGGTT | 11699 |
| TGGTCAGAAG | CAGCTGAATA | AAAGTAAAAA | AATATACAGT | CAAAATACAA | ATTTTATTTT | 11759 |
| GACTGCAAGA | GAACCAAAAT | CTTATGGTTT | AATGAAGAAA | TGTTTTCCAT | ATAACAAAGT | 11819 |
| AATCTTGACA | CCGGATATCG | TGCTCTCATT | TAAATTGAA | GTCACCATTT | CTGATACGCA | 11879 |
| TATTGGGAAA | GAAAAGGATA | GTGTTATAAC | TTATGAAAAT | CGTCAACACT | ATCTTGAGAT | 11939 |
| AAAGTGGGAT | GAAATTGCGC | AGCATGAGGT | CGCCTTAACT | GATAGATTAC | ATGGTATGAT | 11999 |
| TTTTTCATAT | ATCACAGGCA | CACCATGTGT | TGTTTTGGCT | AATAATAATC | ATAAAATTGA | 12059 |
| AGGAACATAC | AAACATTGGT | TGAATGAAGT | CAACTATATT | CGTTTATTG | AAAATCCGAC | 12119 |
| TGTTGAAAAT | ATTTTAGATG | CAATCAATGA | CTTAAAGCAA | ATCGAACCTC | ACTATATTGA | 12179 |
| TTTATCTGAT | AAATTTCAAC | CACTAATTGA | TGCGATAAAA | GGGTAAAGGT | TTA ATG | 12235 |
| | | | | | Met | |
| | | | | | 1 | |

| | | | | | | | | | | | | | | | | |
|---|---|---|---|---|---|---|---|---|---|---|---|---|---|---|---|---|
| AAT | AAA | TAT | AAA | AAA | CTA | CTA | TCC | AAC | TCT | CTT | GTT | TTC | ACG | ATA | GGA | 12283 |
| Asn | Lys | Tyr | Lys | Lys | Leu | Leu | Ser | Asn | Ser | Leu | Val | Phe | Thr | Ile | Gly | |
| | | | 5 | | | | | 10 | | | | | 15 | | | |
| AAC | TTA | GGC | AGC | AAA | CTG | TTA | GTC | TTT | TTA | CTC | GTA | CCG | CTC | TAC | ACC | 12331 |
| Asn | Leu | Gly | Ser | Lys | Leu | Leu | Val | Phe | Leu | Leu | Val | Pro | Leu | Tyr | Thr | |
| | | | 20 | | | | 25 | | | | | 30 | | | | |
| TAT | GCG | ATG | ACA | CCG | CAA | GAG | TAT | GGT | ATG | GCA | GAC | TTA | TAT | CAA | ACA | 12379 |
| Tyr | Ala | Met | Thr | Pro | Gln | Glu | Tyr | Gly | Met | Ala | Asp | Leu | Tyr | Gln | Thr | |
| | | 35 | | | | 40 | | | | | 45 | | | | | |
| ACA | GCA | AAT | CTA | CTT | TTG | CCA | TTA | ATT | ACA | ATG | AAT | GTA | TTT | GAT | GCA | 12427 |
| Thr | Ala | Asn | Leu | Leu | Leu | Pro | Leu | Ile | Thr | Met | Asn | Val | Phe | Asp | Ala | |
| 50 | | | | | 55 | | | | 60 | | | | | | 65 | |
| ACT | TTA | CGT | TTT | GCT | ATG | GAA | AAG | TCA | ATG | ACA | AAA | GAG | AGT | GTG | TTA | 12475 |
| Thr | Leu | Arg | Phe | Ala | Met | Glu | Lys | Ser | Met | Thr | Lys | Glu | Ser | Val | Leu | |
| | | | 70 | | | | | 75 | | | | | 80 | | | |
| ACA | AAT | TCT | CTT | GTG | GTT | TGG | TGT | TTT | AGC | GCG | GTG | TTC | ACT | TGT | TTG | 12523 |
| Thr | Asn | Ser | Leu | Val | Val | Trp | Cys | Phe | Ser | Ala | Val | Phe | Thr | Cys | Leu | |
| | | | 85 | | | | | 90 | | | | | 95 | | | |
| GGC | GCT | TGT | ATT | ATC | TAT | GCG | TTG | AAC | TTG | AGT | AAT | AAA | TGG | TAT | TTA | 12571 |
| Gly | Ala | Cys | Ile | Ile | Tyr | Ala | Leu | Asn | Leu | Ser | Asn | Lys | Trp | Tyr | Leu | |
| | | | 100 | | | | | 105 | | | | | 110 | | | |
| GCT | TTA | CTT | TTA | ACC | TTC | AAC | TTA | TTT | CAA | GGT | GGA | CAA | AGT | ATA | TTA | 12619 |
| Ala | Leu | Leu | Leu | Thr | Phe | Asn | Leu | Phe | Gln | Gly | Gly | Gln | Ser | Ile | Leu | |
| | | | 115 | | | | | 120 | | | | | 125 | | | |

| | | | | | | | | | | | | | | | | |
|---|---|---|---|---|---|---|---|---|---|---|---|---|---|---|---|---|
| AGC | CAG | TAT | GCT | AGA | GGT | ATA | GGA | AAG | TCG | AAA | ATA | TTT | GCA | GCT | GGC | 12667 |
| Ser | Gln | Tyr | Ala | Arg | Gly | Ile | Gly | Lys | Ser | Lys | Ile | Phe | Ala | Ala | Gly | |
| 130 | | | | 135 | | | | | 140 | | | | | | 145 | |
| GGA | GTT | ATT | TTA | ACC | TTT | TTG | ACA | GGC | GCT | TTA | AAT | ATT | CTT | TTT | TTG | 12715 |
| Gly | Val | Ile | Leu | Thr | Phe | Leu | Thr | Gly | Ala | Leu | Asn | Ile | Leu | Phe | Leu | |
| | | | | 150 | | | | | 155 | | | | | 160 | | |
| GTA | TAT | TTA | CCG | CTT | GGG | ATT | ACG | GGC | TAT | TTA | ATG | TCC | CTG | GTT | TTA | 12763 |
| Val | Tyr | Leu | Pro | Leu | Gly | Ile | Thr | Gly | Tyr | Leu | Met | Ser | Leu | Val | Leu | |
| | | | 165 | | | | | 170 | | | | | 175 | | | |
| GCG | AAT | GTA | GGT | ACG | ATT | CTA | TTT | TTT | GCT | GGC | ACA | CTT | TCC | ATT | TGG | 12811 |
| Ala | Asn | Val | Gly | Thr | Ile | Leu | Phe | Phe | Ala | Gly | Thr | Leu | Ser | Ile | Trp | |
| | | 180 | | | | | 185 | | | | | 190 | | | | |
| AAG | GAA | ATT | AGT | TTT | AAA | ATA | ATT | GAT | AAA | AAA | CTG | ATT | TGG | CAA | ATG | 12859 |
| Lys | Glu | Ile | Ser | Phe | Lys | Ile | Ile | Asp | Lys | Lys | Leu | Ile | Trp | Gln | Met | |
| | | 195 | | | | 200 | | | | | 205 | | | | | |
| CTC | TAT | TAT | GCC | TTA | CCT | TTG | ATT | CCT | AGT | TCC | ATC | CTG | TGG | TGG | TTA | 12907 |
| Leu | Tyr | Tyr | Ala | Leu | Pro | Leu | Ile | Pro | Ser | Ser | Ile | Leu | Trp | Trp | Leu | |
| 210 | | | | 215 | | | | | 220 | | | | | 225 | | |
| CTG | AAT | GCT | TCT | AGT | CGC | TAT | TTC | GTT | TTA | TTC | TTT | TTA | GGA | GCA | GGT | 12955 |
| Leu | Asn | Ala | Ser | Ser | Arg | Tyr | Phe | Val | Leu | Phe | Phe | Leu | Gly | Ala | Gly | |
| | | | | 230 | | | | | 235 | | | | | 240 | | |
| GCT | AAT | GGT | CTT | TTG | GCG | GTC | GCT | ACC | AAA | ATT | CCA | AGT | ATT | ATT | TCC | 13003 |
| Ala | Asn | Gly | Leu | Leu | Ala | Val | Ala | Thr | Lys | Ile | Pro | Ser | Ile | Ile | Ser | |
| | | | 245 | | | | | 250 | | | | | 255 | | | |
| ATT | TTT | AAT | ACG | ATT | TTT | ACA | CAG | GCG | TGG | CAA | ATT | TCA | GCC | ATA | GAA | 13051 |
| Ile | Phe | Asn | Thr | Ile | Phe | Thr | Gln | Ala | Trp | Gln | Ile | Ser | Ala | Ile | Glu | |
| | | 260 | | | | 265 | | | | | 270 | | | | | |
| GAA | TAT | GAT | TCT | CAT | CAA | AAA | TCA | AAA | TAT | TAT | TCG | GAT | GTT | TTT | CAC | 13099 |
| Glu | Tyr | Asp | Ser | His | Gln | Lys | Ser | Lys | Tyr | Tyr | Ser | Asp | Val | Phe | His | |
| | 275 | | | | | 280 | | | | | 285 | | | | | |
| TAC | TTA | GCA | ACT | TTT | CTA | TTG | TTA | GGG | ACA | TCA | GCT | TTT | ATG | ATT | GTG | 13147 |
| Tyr | Leu | Ala | Thr | Phe | Leu | Leu | Gly | Thr | Ser | Ala | Phe | Met | Ile | Val | |
| 290 | | | | | 295 | | | | | 300 | | | | | 305 | |
| CTT | AAA | CCA | ATT | GTC | GAA | AAA | GTC | GTT | TCA | AGT | GAC | TAT | GCA | AGT | TCA | 13195 |
| Leu | Lys | Pro | Ile | Val | Glu | Lys | Val | Val | Ser | Ser | Asp | Tyr | Ala | Ser | Ser | |
| | | | | 310 | | | | | 315 | | | | | 320 | | |
| TGG | CAA | TAT | GTT | CCT | TTC | TTT | ATG | TTG | TCG | ATG | CTA | TTT | TCC | TCG | TTT | 13243 |
| Trp | Gln | Tyr | Val | Pro | Phe | Phe | Met | Leu | Ser | Met | Leu | Phe | Ser | Ser | Phe | |
| | | | 325 | | | | | 330 | | | | | 335 | | | |
| TCT | GAT | TTT | TTT | GGG | ACT | AAT | TAT | ATT | GCG | GCT | AAA | CAA | ACA | AAA | GGC | 13291 |
| Ser | Asp | Phe | Phe | Gly | Thr | Asn | Tyr | Ile | Ala | Ala | Lys | Gln | Thr | Lys | Gly | |
| | | 340 | | | | 345 | | | | | 350 | | | | | |
| GTA | TTT | ATG | ACA | TCT | ATC | TAT | GGT | ACC | ATT | GTT | TGT | GTC | TTA | CTC | CAA | 13339 |
| Val | Phe | Met | Thr | Ser | Ile | Tyr | Gly | Thr | Ile | Val | Cys | Val | Leu | Leu | Gln | |
| | 355 | | | | | 360 | | | | | 365 | | | | | |
| GTG | GTG | CTG | CTA | CCC | ATC | ATC | GGC | TTG | GAT | GGC | GCA | GGT | TTA | TCA | GCC | 13387 |
| Val | Val | Leu | Leu | Pro | Ile | Ile | Gly | Leu | Asp | Gly | Ala | Gly | Leu | Ser | Ala | |
| 370 | | | | | 375 | | | | | 380 | | | | | 385 | |
| ATG | CTT | GGA | TTT | TTA | ACA | ACG | TTT | TTA | TTG | CGT | GTC | AAA | GAT | ACG | CAA | 13435 |
| Met | Leu | Gly | Phe | Leu | Thr | Thr | Phe | Leu | Leu | Arg | Val | Lys | Asp | Thr | Gln | |
| | | | | 390 | | | | | 395 | | | | | 400 | | |
| AAA | TTT | GTG | GTG | ATT | CAG | ATT | AAG | TGG | CGG | ATT | TTT | ATC | AGT | AAT | TTA | 13483 |
| Lys | Phe | Val | Val | Ile | Gln | Ile | Lys | Trp | Arg | Ile | Phe | Ile | Ser | Asn | Leu | |
| | | | 405 | | | | | 410 | | | | | 415 | | | |
| TTG | ATC | GTT | TTG | GCA | CAA | ATT | TTA | TGT | TTG | TTT | TAT | CTA | CCG | AGT | GAA | 13531 |
| Leu | Ile | Val | Leu | Ala | Gln | Ile | Leu | Cys | Leu | Phe | Tyr | Leu | Pro | Ser | Glu | |
| | | 420 | | | | 425 | | | | | 430 | | | | | |
| TTT | TTG | TAT | TTT | GGT | CTT | GCC | CTA | TTA | TTT | TGT | GGC | ATG | TTA | GTG | GTT | 13579 |
| Phe | Leu | Tyr | Phe | Gly | Leu | Ala | Leu | Leu | Phe | Cys | Gly | Met | Leu | Val | Val | |
| | 435 | | | | | 440 | | | | | 445 | | | | | |

```
AAT CAG CGT ACA ATT TTA TAC ATT ATC ATG GCG CTA AAA ATA AAA AAT       13627
Asn Gln Arg Thr Ile Leu Tyr Ile Ile Met Ala Leu Lys Ile Lys Asn
450                 455                 460                 465

AAG ACA TTT GGA ATG AAA TCC TCA TAAAAATAGA CAGGAGGTGT ATCTCGAATG       13681
Lys Thr Phe Gly Met Lys Ser Ser
                470

GTATCGAGAT ATATCTCCTG TCTATTTTTA TGATACTTTT GTGTTAGCTC AACTCAACCG       13741
CCTTTTAATC TCCCAACAAC AATAATACCC AATCAAACAA CCCAAAAAAT TCAAGATAAT       13801
ATCACTAATG GCAAATGTGC CCAAATAAAA GATAAATTGA ATGGTTTCAA TTACTAAAAG       13861
AGTGACCAAA CTGACAATGA CAAACTGTTT GAAATCAGTA TTGATACAGT AAAGGCCACC       13921
TAAAGGAATG AAGTAGATAA TATTTAGCAC AGCCTCTTGA ATCGTTCTGG GATCCGCTTT       13981
TATAAAGTCA AAAGGATTCA GTGACATCGC CTGAAAATCC GTTATTTTAG TAAAAAGTAC       14041
CATGAATAAC AGTAATAAAT ACACACTGAA AGCAAGATAG AGATAAATAA CTGAAAAATA       14101
TTTGAGGTGA TACTGGATAC CAAACAACCA GATAATCAGC GTTAATAAGA GTATTAAAGT       14161
CAATGTGGTA TAGTCAAAGT GGTTAATCAA CTTAGCCAGG CTTTGATAGC GAGTGAGAAC       14221
GGGCATAATC AGCCAAGTAA TCGTCGCATA ACTCAGGATA AATGTGATCA ATAAACTGCT       14281
GAGGTAGATC ATATATTTTC GCAACTGTTT CTAACTCCTT TTCTTGATGA GATTAACCCT       14341
ATTTTAACAT ATTTTAAAAC TGTCATGTTT TTATGAATTT AAAATAAATG TTAAAGAAAA       14401
TAAAAATTCA CCAGTTGGTT CTGTTGCAAA GTTTCCAAA AAATCTATTT TAGTGTAAAA        14461
TTGAGAAAAA AGACAGAGAG GACAGAGTAA TGAATTATTT TAAAGGCAAA CAATTCAAAA       14521
AAGACGTCAT TATTGTCTCT GTTGGTTACT ACCTGCGTTA CAATCTAAGC TATCGTTAAG       14581
TTCAGGAATT GTTATATGAT C                                                14602
```

( 2 ) INFORMATION FOR SEQ ID NO:2:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Ser Arg Thr Asn Arg Lys Gln Lys His Thr Ser Asn Gly Ser
1               5                   10                  15

Trp Gly Met Val Asn Val Gly Leu Thr Ile Leu Tyr Ala Ile Leu Ala
            20                  25                  30

Leu Val Leu Leu Phe Thr Met Phe Asn Tyr Asn Phe Leu Ser Phe Arg
        35                  40                  45

Phe Leu Asn Ile Ile Ile Thr Ile Gly Leu Leu Val Val Leu Ala Ile
    50                  55                  60

Ser Ile Phe Leu Gln Lys Thr Lys Lys Leu Pro Leu Val Thr Thr Val
65                  70                  75                  80

Val Leu Val Ile Phe Ser Leu Val Ser Leu Val Gly Ile Phe Gly Phe
                85                  90                  95

Lys Gln Met Ile Asp Ile Thr Asn Arg Met Asn Gln Thr Ala Ala Phe
            100                 105                 110

Ser Glu Val Glu Met Ser Ile Val Val Pro Lys Glu Ser Asp Ile Lys
        115                 120                 125

Asp Val Ser Gln Leu Thr Ser Val Gln Ala Pro Thr Lys Val Asp Lys
    130                 135                 140

Asn Asn Ile Glu Ile Leu Met Ser Ala Leu Lys Lys Asp Lys Lys Val
```

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     | 150 |     |     |     | 155 |     |     |     |     |     |     | 160 |
| Asp | Val | Lys | Val | Asp | Val | Ala | Ser | Tyr | Gln | Glu | Ala | Tyr | Asp | Asn |     |
|     |     |     |     | 165 |     |     |     | 170 |     |     |     | 175 |     |     |     |
| Leu | Lys | Ser | Gly | Lys | Ser | Lys | Ala | Met | Val | Leu | Ser | Gly | Ser | Tyr | Ala |
|     |     |     | 180 |     |     |     |     | 185 |     |     |     |     | 190 |     |     |
| Ser | Leu | Leu | Glu | Ser | Val | Asp | Ser | Asn | Tyr | Ala | Ser | Asn | Leu | Lys | Thr |
|     |     | 195 |     |     |     |     | 200 |     |     |     |     | 205 |     |     |     |
| Ile | Tyr | Thr | Tyr | Lys | Ile | Lys | Lys | Asn | Ser | Asn | Ser | Ala | Asn | Gln |     |
|     | 210 |     |     |     | 215 |     |     |     |     | 220 |     |     |     |     |     |
| Val | Asp | Ser | Arg | Val | Phe | Asn | Ile | Tyr | Ile | Ser | Gly | Ile | Asp | Thr | Tyr |
| 225 |     |     |     |     | 230 |     |     |     |     | 235 |     |     |     |     | 240 |
| Gly | Pro | Ile | Ser | Thr | Val | Ser | Arg | Ser | Asp | Val | Asn | Ile | Ile | Met | Thr |
|     |     |     |     | 245 |     |     |     |     | 250 |     |     |     |     | 255 |     |
| Val | Asn | Met | Asn | Thr | His | Lys | Ile | Leu | Leu | Thr | Thr | Thr | Pro | Arg | Asp |
|     |     |     | 260 |     |     |     |     | 265 |     |     |     |     | 270 |     |     |
| Ala | Tyr | Val | Lys | Ile | Pro | Gly | Gly | Gly | Ala | Asp | Gln | Tyr | Asp | Lys | Leu |
|     |     | 275 |     |     |     |     | 280 |     |     |     |     | 285 |     |     |     |
| Thr | His | Ala | Gly | Ile | Tyr | Gly | Val | Glu | Thr | Ser | Glu | Gln | Thr | Leu | Glu |
|     | 290 |     |     |     | 295 |     |     |     |     | 300 |     |     |     |     |     |
| Asp | Leu | Tyr | Gly | Ile | Lys | Leu | Asp | Tyr | Tyr | Ala | Arg | Ile | Asn | Phe | Thr |
| 305 |     |     |     |     | 310 |     |     |     |     | 315 |     |     |     |     | 320 |
| Ser | Phe | Leu | Lys | Leu | Ile | Asp | Gln | Leu | Gly | Gly | Val | Thr | Val | His | Asn |
|     |     |     |     | 325 |     |     |     |     | 330 |     |     |     |     | 335 |     |
| Asp | Gln | Ala | Phe | Thr | Gln | Glu | Lys | Phe | Asp | Phe | Pro | Val | Gly | Asp | Ile |
|     |     |     | 340 |     |     |     |     | 345 |     |     |     |     | 350 |     |     |
| Gln | Met | Asn | Ser | Glu | Gln | Ala | Leu | Gly | Phe | Val | Arg | Glu | Arg | Tyr | Asn |
|     |     | 355 |     |     |     |     | 360 |     |     |     |     | 365 |     |     |     |
| Leu | Asp | Gly | Gly | Asp | Asn | Asp | Arg | Gly | Lys | Asn | Gln | Glu | Lys | Val | Ile |
|     | 370 |     |     |     | 375 |     |     |     |     | 380 |     |     |     |     |     |
| Ser | Ala | Ile | Leu | Asn | Lys | Leu | Ala | Ser | Leu | Lys | Ser | Val | Ser | Asn | Phe |
| 385 |     |     |     |     | 390 |     |     |     |     | 395 |     |     |     |     | 400 |
| Thr | Ser | Ile | Val | Asn | Asn | Leu | Gln | Asp | Ser | Val | Gln | Thr | Asn | Met | Ser |
|     |     |     |     | 405 |     |     |     |     | 410 |     |     |     |     | 415 |     |
| Leu | Asn | Thr | Ile | Asn | Ala | Leu | Ala | Asn | Thr | Gln | Leu | Glu | Ser | Gly | Ser |
|     |     |     | 420 |     |     |     |     | 425 |     |     |     |     | 430 |     |     |
| Lys | Phe | Thr | Val | Thr | Ser | Gln | Ala | Val | Thr | Gly | Thr | Gly | Ser | Thr | Gly |
|     |     | 435 |     |     |     |     | 440 |     |     |     |     | 445 |     |     |     |
| Gln | Leu | Ile | Ser | Tyr | Ala | Met | Pro | Asn | Ser | Ser | Leu | Tyr | Met | Met | Lys |
|     | 450 |     |     |     | 455 |     |     |     |     | 460 |     |     |     |     |     |
| Leu | Asp | Asn | Ser | Ser | Val | Glu | Ser | Ala | Ser | Gln | Ala | Ile | Lys | Lys | Leu |
| 465 |     |     |     | 470 |     |     |     |     | 475 |     |     |     |     |     | 480 |
| Met | Glu | Glu | Lys |     |     |     |     |     |     |     |     |     |     |     |     |

( 2 ) INFORMATION FOR SEQ ID NO:3:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

|     |     |     |     |     |     |     |     |     |     |     |     |     |     |     |
|-----|-----|-----|-----|-----|-----|-----|-----|-----|-----|-----|-----|-----|-----|-----|
| Val | Ile | Asp | Val | His | Ser | His | Ile | Val | Phe | Asp | Val | Asp | Asp | Gly | Pro |
| 1   |     |     |     | 5   |     |     |     |     | 10  |     |     |     |     | 15  |
| Glu | Thr | Leu | Glu | Glu | Ser | Leu | Asp | Leu | Ile | Gly | Glu | Ser | Tyr | Ala | Gln |

|  |  |  |  | 20 |  |  | 25 |  |  |  | 30 |  |  |
|---|---|---|---|---|---|---|---|---|---|---|---|---|---|
| Gly | Val | Arg 35 | Lys | Ile | Val | Ser | Thr 40 | Ser | His | Arg | Arg | Lys 45 | Gly | Met | Phe |
| Glu | Thr 50 | Pro | Glu | Asp | Lys | Ile 55 | Phe | Ala | Asn | Phe | Lys 60 | Lys | Val | Lys | Ala |
| Glu 65 | Ala | Glu | Ala | Leu | Tyr 70 | Pro | Asp | Leu | Thr | Ile 75 | Tyr | Tyr | Gly | Gly | Glu 80 |
| Leu | Tyr | Tyr | Thr | Ser 85 | Asp | Ile | Val | Glu | Lys 90 | Leu | Glu | Lys | Asn | Leu 95 | Ile |
| Pro | Arg | Met | His 100 | Asn | Thr | Gln | Phe | Ala 105 | Leu | Ile | Glu | Phe | Ser 110 | Ala | Arg |
| Thr | Ser | Trp 115 | Lys | Glu | Ile | His | Ser 120 | Gly | Leu | Ser | Asn | Val 125 | Leu | Arg | Ala |
| Gly | Val 130 | Thr | Pro | Ile | Val | Ala 135 | His | Ile | Glu | Arg | Tyr 140 | Asp | Ala | Leu | Glu |
| Glu 145 | Asn | Ala | Asp | Arg | Val 150 | Arg | Glu | Ile | Ile | Asn 155 | Met | Gly | Cys | Tyr | Thr 160 |
| Gln | Val | Asn | Ser | Ser 165 | His | Val | Leu | Lys | Pro 170 | Lys | Leu | Phe | Gly | Asp 175 | Lys |
| Asp | Lys | Val | Arg 180 | Lys | Lys | Arg | Val | Arg 185 | Phe | Phe | Leu | Glu | Lys 190 | Asn | Leu |
| Val | His | Met 195 | Val | Ala | Ser | Asp | Met 200 | His | Asn | Leu | Gly | Pro 205 | Arg | Pro | Pro |
| Phe | Met 210 | Lys | Asp | Ala | Tyr | Glu 215 | Ile | Val | Lys | Lys | Asn 220 | Tyr | Gly | Ser | Lys |
| Arg 225 | Ala | Lys | Asn | Leu | Phe 230 | Ile | Glu | Asn | Pro | Lys 235 | Thr | Leu | Leu | Glu | Asn 240 |
| Gln | Tyr | Leu |

( 2 ) INFORMATION FOR SEQ ID NO:4:

( i ) SEQUENCE CHARACTERISTICS:
        ( A ) LENGTH: 230 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met 1 | Asn | Gln | Asp | Asn 5 | Thr | Lys | Ser | Asp | Glu 10 | Ile | Asp | Val | Leu | Ala 15 | Leu |
|---|---|---|---|---|---|---|---|---|---|---|---|---|---|---|---|
| Leu | His | Lys | Leu 20 | Trp | Thr | Lys | Lys | Leu 25 | Leu | Ile | Leu | Phe | Thr 30 | Ala | Phe |
| Tyr | Phe | Ala 35 | Val | Phe | Ser | Phe | Leu 40 | Gly | Thr | Tyr | Phe | Phe 45 | Ile | Gln | Pro |
| Thr | Tyr 50 | Thr | Ser | Thr | Thr | Arg 55 | Ile | Tyr | Val | Val | Asn 60 | Gln | Ala | Thr | Asp |
| Asn 65 | Lys | Asn | Leu | Ser | Ala 70 | Gln | Asp | Leu | Gln | Ala 75 | Gly | Thr | Tyr | Leu | Ala 80 |
| Asn | Asp | Tyr | Lys | Glu 85 | Ile | Ile | Ala | Ser | Asn 90 | Asp | Val | Leu | Ser | Glu 95 | Val |
| Ile | Lys | Asp | Glu 100 | Lys | Leu | Asn | Leu | Ser 105 | Glu | Ala | Glu | Leu | Ser 110 | Lys | Met |
| Val | Ser | Val 115 | Asn | Ile | Pro | Thr | Asp 120 | Thr | Arg | Leu | Ile | Ser 125 | Ile | Ser | Val |
| Asn | Ala | Lys | Thr | Gly | Gln | Asp | Ala | Gln | Thr | Leu | Ala | Asn | Lys | Val | Arg |

|  |  |  |  | 130 |  |  |  | 135 |  |  |  | 140 |  |  |
|---|---|---|---|---|---|---|---|---|---|---|---|---|---|---|
| Glu<br>145 | Val | Ala | Ser | Lys<br>150 | Lys | Ile | Lys | Val<br>155 | Thr | Lys | Val | Glu | Asp | Val<br>160 |
| Thr | Thr | Leu | Glu | Glu<br>165 | Ala | Lys | Leu | Pro | Glu<br>170 | Ser | Pro | Ser | Ser<br>175 | Pro | Asn |
| Ile | Lys | Leu | Asn<br>180 | Val | Leu | Leu | Gly | Ala<br>185 | Val | Leu | Gly | Gly<br>190 | Phe | Leu | Ala |
| Val | Val | Gly<br>195 | Val | Leu | Val | Arg | Glu<br>200 | Ile | Leu | Asp | Asp | Arg<br>205 | Val | Arg | Arg |
| Pro | Glu<br>210 | Asp | Val | Glu | Asp | Ala<br>215 | Leu | Gly | Met | Thr | Leu<br>220 | Leu | Gly | Ile | Val |
| Pro<br>225 | Asp | Thr | Asp | Lys | Ile<br>230 |

(2) INFORMATION FOR SEQ ID NO:5:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO:5:

| Met<br>1 | Pro | Leu | Leu | Lys<br>5 | Leu | Val | Lys | Ser | Val<br>10 | Val | Asp | Phe | Ala | Lys<br>15 | Lys |
|---|---|---|---|---|---|---|---|---|---|---|---|---|---|---|---|
| Thr | Glu | Glu | Tyr<br>20 | Tyr | Asn | Ala | Ile | Arg<br>25 | Thr | Asn | Ile | Gln | Phe<br>30 | Ser | Gly |
| Ala | Gln | Met<br>35 | Lys | Val | Ile | Ala | Ile<br>40 | Ser | Ser | Val | Glu | Ala<br>45 | Gly | Glu | Gly |
| Lys | Ser<br>50 | Met | Ile | Ser | Val | Asn<br>55 | Leu | Ala | Ile | Ser | Phe<br>60 | Ala | Ser | Val | Gly |
| Leu<br>65 | Arg | Thr | Leu | Leu | Ile<br>70 | Asp | Ala | Glu | Thr | Arg<br>75 | Asn | Ser | Val | Leu | Ser<br>80 |
| Gly | Thr | Phe | Lys | Ser<br>85 | Asn | Glu | Pro | Tyr | Lys<br>90 | Gly | Leu | Ser | Asn | Phe<br>95 | Leu |
| Ser | Gly | Asn | Ala<br>100 | Asp | Leu | Asn | Glu | Thr<br>105 | Ile | Cys | Gln | Thr | Asp<br>110 | Ile | Ser |
| Gly | Leu | Asp<br>115 | Val | Ile | Ala | Ser | Gly<br>120 | Pro | Val | Pro | Pro | Asn<br>125 | Pro | Thr | Ser |
| Leu | Leu | Gln | Asn<br>130 | Asp | Asn | Phe<br>135 | Arg | His | Leu | Met | Glu<br>140 | Val | Ala | Arg | Ser |
| Cys<br>145 | Tyr | Asp | Tyr | Val | Ile<br>150 | Ile | Asp | Thr | Pro | Pro<br>155 | Val | Gly | Leu | Val | Ile<br>160 |
| Asp | Ala | Val | Ile | Ile<br>165 | Ala | His | Gln | Ala | Asp<br>170 | Ala | Ser | Leu | Leu | Val<br>175 | Thr |
| Glu | Ala | Gly | Lys<br>180 | Ile | Lys | Arg | Arg | Phe<br>185 | Val | Thr | Lys | Ala | Val<br>190 | Glu | Gln |
| Leu | Val | Glu<br>195 | Ser | Gly | Ser | Gln | Phe<br>200 | Leu | Gly | Val | Val | Leu<br>205 | Asn | Lys | Val |
| Asp | Met<br>210 | Thr | Val | Asp | Lys | Tyr<br>215 | Gly | Phe | Tyr | Gly | Ser<br>220 | Tyr | Gly | Ser | Tyr |
| Gly<br>225 | Glu | Tyr | Gly | Lys | Lys<br>230 | Ser | Asp | Gln | Lys | Glu<br>235 | Gly | His | Ser | Arg | Ala<br>240 |
| His | Arg | Arg | Arg | Lys<br>245 | Val | Gly | Trp | Asn |

( 2 ) INFORMATION FOR SEQ ID NO:6:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Gln Ala Lys Glu Glu Ile Ser Asp Val Met Thr Tyr Ser Glu
 1               5                  10                 15
Leu Thr Ser His Lys Pro Lys Ile Ile Tyr Ser Leu Ile Lys Arg Ile
                20                  25                 30
Gly Asp Ile Leu Val Ser Ser Ile Gly Leu Ile Ile Leu Ile Pro Leu
            35                  40                 45
Phe Leu Ile Val Ala Leu Ile Met Lys Cys Ser Glu Pro Thr Ala Pro
        50                  55                 60
Ile Phe Phe Ser His Ile Arg Asn Gly Lys Asn Gly Lys Lys Phe Lys
65                  70                  75                     80
Met Tyr Lys Phe Arg Thr Met Cys Gln Asp Ala Glu Ser Ile Leu Met
                85                  90                 95
Lys Asp Thr Glu Leu Phe Ala Lys Phe Lys Ala Asn Gly Tyr Lys Leu
            100                 105                110
Glu Thr His Glu Asp Pro Arg Ile Thr Lys Ile Gly Gly Ile Leu Arg
            115                 120                125
Lys Thr Ser Ile Asp Glu Leu Pro Gln Leu Ile Asn Val Phe Leu Gly
        130                 135                140
Gln Met Ser Leu Val Gly Pro Arg Pro Leu Pro Asp Arg Glu Ile Ile
145                 150                 155                    160
Glu Tyr Gly Asp Asn Gln Glu Lys Phe Leu Ser Val Lys Pro Gly Met
                165                 170                175
Thr Gly Trp Trp Gln Val Ser Gly Arg Ser Thr Ile Gly Tyr Pro Glu
            180                 185                190
Arg Cys His Leu Glu Leu Tyr Tyr Val Glu Lys Cys Cys Phe Thr Phe
            195                 200                205
Asp Val Leu Ile Leu Leu Lys Thr Ile Gly Ile Val Leu Lys Arg Val
        210                 215                220
Gly Ala Arg
225
```

( 2 ) INFORMATION FOR SEQ ID NO:7:

( i ) SEQUENCE CHARACTERISTICS:
        ( A ) LENGTH: 319 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Asn Glu Gln Val Thr Phe Ile Leu Cys Asp Phe Leu Val Arg Glu
 1               5                  10                 15
Ile Lys Pro Lys Tyr Asp Leu Leu Ala Tyr Gln Phe Ile Ser Lys Lys
                20                  25                 30
Ile Lys Glu Ile Lys Pro Asp Ile Val His Cys His Ser Ser Lys Ala
            35                  40                 45
Gly Val Ile Gly Arg Leu Ala Ala Lys Arg Arg Gly Val Lys Lys Ile
        50                  55                 60
```

| Phe 65 | Tyr | Thr | Pro | His 70 | Ala | Tyr | Ser | Phe | Ala 75 | Pro | Glu | Phe | Ser | Gly 80 |
| Lys | Lys | Lys | Phe | Leu 85 | Phe | Val | Gln | Ile | Glu 90 | Lys | Phe | Leu | Ser | Arg 95 | Phe |

Ala Thr Thr Lys Ile Phe Cys Val Ser Ile Ala Glu Met Gln Ala Ala
        100           105           110

Leu Glu Val Asn Leu Asp Lys Thr Asp Lys Phe Gln Val Ile Tyr Asn
        115           120           125

Gly Leu Pro Glu Ile Asp Leu Pro Ser Lys Glu Thr Ile Arg Ala Gln
    130           135           140

Leu Gly Leu Glu Lys Ala Ala Val Val Ile Gly Asn Asn Ala Lys Met
145           150           155           160

Ser Glu Gln Lys Asn Pro Met Phe Phe Met Glu Ile Ala Arg Lys Met
            165           170           175

Ile Arg Gln Asn Ala Asn Trp His Phe Val Trp Val Gly Asp Gly Gln
            180           185           190

Leu Met Pro Leu Phe Gln Ser Phe Ile Lys Gln Asn Gly Leu Glu Gly
        195           200           205

Asn Ile His Leu Leu Gly Glu Arg Pro Asp Ser Glu Ile Val Val Thr
    210           215           220

Ala Tyr Asp Ile Phe Leu Thr Thr Ser Gln Tyr Glu Gly Leu Pro Tyr
225           230           235           240

Ala Pro Ile Glu Ala Met Arg Ala Gly Val Pro Ile Leu Ala Thr Lys
            245           250           255

Val Val Gly Asn Ser Glu Leu Val Ile Glu Gly Lys Asn Gly Tyr Leu
            260           265           270

Ile Asp Leu Glu Trp Ser Lys Ser Val Glu Glu Lys Leu Tyr Lys Ala
        275           280           285

Ala Lys Ile Asp Ala Gln Met Ile Lys Ala Asp Phe Arg Gln Arg Phe
290           295           300

Ala Ile Asp Gln Ile Leu Lys Gln Ile Glu Thr Ile Tyr Leu Ala
305           310           315

(2) INFORMATION FOR SEQ ID NO:8:

(i) SEQUENCE CHARACTERISTICS:
      (A) LENGTH: 372 amino acids
      (B) TYPE: amino acid
      (D) TOPOLOGY: linear (ii) MOLECULE TYPE: protein (xi) SEQUENCE DESCRIPTION: SEQ ID NO:8:

Met Lys Lys Ile Ser Ile Leu His Phe Ser Gln Val Ser Gly Gly Gly
1           5           10           15

Val Glu Lys Tyr Ile Lys Leu Phe Leu Lys Tyr Ser Asp Val Thr Lys
            20           25           30

Phe Asn Asn Tyr Leu Val Ala Pro Asn Leu Glu Asn Tyr Asp Glu Phe
        35           40           45

Asn Gly Tyr Leu Lys Met Ser Val Asn Phe Asn Met Glu Gln Thr Phe
    50           55           60

Ser Pro Leu Lys Ile Phe Lys Asn Val Phe Phe Ile Arg Ser Val Leu
65           70           75           80

Lys Lys Ile Asn Pro Asp Ile Val Tyr Leu His Ser Thr Phe Ala Gly
            85           90           95

Val Val Gly Arg Ile Ala Ser Ile Gly Leu Pro Thr Lys Val Val Tyr

|   |   |   |   |   | 100 |   |   |   |   | 105 |   |   |   |   | 110 |   |   |
|---|---|---|---|---|---|---|---|---|---|---|---|---|---|---|---|---|---|
| Asn | Pro | His | Gly | Trp | Ser | Phe | Lys | Met | Asp | Asn | Ser | Tyr | Leu | Lys | Lys |
|   |   | 115 |   |   |   |   | 120 |   |   |   |   | 125 |   |   |   |

Leu Ile Phe Lys Leu Ile Glu Phe Ser Leu Ser Phe Leu Thr Asp Lys
    130             135                 140

Phe Ile Leu Ile Ser Glu Ser Glu Tyr Ile Leu Ala Asn His Ile Ser
145             150                 155                         160

Phe Asn Lys Ser Lys Phe Ser Leu Ile Asn Asn Gly Val Glu Val Ile
            165                 170                 175

Thr Gly Asp Ser Arg Asn Glu Ile Glu Glu Ile Phe Pro Asn Glu Asp
            180                 185                 190

Phe Ile Ile Gly Met Val Gly Arg Leu Ser Pro Pro Lys Glu Phe Phe
            195                 200                 205

Phe Phe Ile Asp Phe Ala Lys Lys Ile Leu Gln Ile Arg Asn Asp Thr
    210                 215                 220

Asn Phe Ile Ile Val Gly Asp Gly Glu Leu Arg Ser Glu Ile Glu Arg
225                 230                 235                 240

Met Ile Leu Asp Asn Gly Leu Gly Asp Lys Ile Tyr Ile Thr Gly Trp
            245                 250                 255

Val Asp Asn Pro Arg Asn Tyr Ile Glu Lys Phe Asp Gln Ala Ile Leu
            260                 265                 270

Phe Ser Arg Trp Glu Gly Leu Ser Leu Thr Ile Ala Glu Tyr Met Ser
        275                 280                 285

Gln Lys Lys Thr Ile Leu Ala Thr Asn Ile Gly Gly Ile Asn Asp Leu
    290                 295                 300

Ile Thr Asp Gly Glu Thr Gly Met Leu Ile Glu Val Gly Asp Leu Asn
305                 310                 315                 320

Ser Ala Val Ser Lys Ser Phe Glu Leu Arg Asn Asn Lys Glu Val Ser
            325                 330                 335

Asn Gln Leu Ala Asn Asn Ala Tyr Asn Lys Val Val Glu Gln Phe Ser
            340                 345                 350

Ile Glu Lys Gln Met Ala Glu Ile Glu Ser Leu Phe Ile Glu Met Cys
        355                 360                 365

Asn Asn Glu Lys
        370

(2) INFORMATION FOR SEQ ID NO:9:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:9:

Met Leu Ile Leu Lys Leu Lys Phe His Leu Lys Ser Leu Phe Leu Lys
1               5                   10                  15

Trp Ile Tyr Arg Leu Leu Tyr Leu Lys Lys Phe Gln Phe Gly Ala Arg
            20                  25                  30

Leu Thr Phe Arg Asp Gly Phe His Leu Leu Ile Glu Lys Ser Gly Lys
        35                  40                  45

Val Ile Ile Gly Asn His Val Phe Phe Asn Asn Phe Cys Ser Ile Asn
    50                  55                  60

Ala Met Leu Ser Val Thr Ile Gly Asp Asp Cys Ile Phe Gly Glu Asn
65                  70                  75                  80

| | | | | | | | | | | | | | | |
|---|---|---|---|---|---|---|---|---|---|---|---|---|---|---|
| Val | Lys | Ile | Tyr | Asp 85 | His | Asn | His | Cys | Tyr 90 | Gln | Asn | Lys | Ser | Gln 95 | Pro |
| Ile | Ser | Lys | Gln 100 | Gly | Phe | Ser | Thr | Ala 105 | Ala | Ile | Gln | Ile 110 | Gly | Arg | Asn |
| Cys | Trp | Ile 115 | Gly | Ser | Gln | Val | Thr 120 | Ile | Leu | Lys | Gly | Val 125 | Thr | Ile | Gly |
| Asp | Asn 130 | Ser | Ile | Ile | Gly 135 | Ala | Gly | Val | Val | Val 140 | Tyr | Gln | Asp | Val | Pro |
| Glu 145 | Asn | Ser | Ile | Val | Leu 150 | Ser | Asn | Gly | Glu | Ile 155 | Arg | Lys | Arg | Gly | |

( 2 ) INFORMATION FOR SEQ ID NO:10:

( i ) SEQUENCE CHARACTERISTICS:
( A ) LENGTH: 324 amino acids
( B ) TYPE: amino acid
( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met 1 | Tyr | Leu | Lys | Ser 5 | Leu | Ile | Ser | Ile | Val 10 | Ile | Pro | Val | Tyr | Asn 15 | Val |
| Glu | Lys | Tyr | Leu 20 | Glu | Lys | Cys | Leu | Gln 25 | Ser | Val | Gln | Asn | Gln 30 | Thr | Tyr |
| Asn | Asn | Phe 35 | Glu | Val | Ile | Leu | Val 40 | Asn | Asp | Gly | Ser | Thr 45 | Asp | Ser | Ser |
| Leu | Ser 50 | Ile | Cys | Glu | Lys | Phe 55 | Val | Asn | Gln | Asp | Lys 60 | Arg | Phe | Ser | Val |
| Phe 65 | Ser | Lys | Glu | Asn | Gly 70 | Gly | Met | Ser | Ser | Ala 75 | Arg | Asn | Phe | Gly 80 | Ile |
| Lys | Lys | Ala | Lys | Gly 85 | Ser | Phe | Ile | Thr | Phe 90 | Val | Asp | Ser | Asp 95 | Asp | Tyr |
| Ile | Val | Lys | Asp 100 | Tyr | Leu | Ser | His | Leu 105 | Val | Ala | Gly | Ile | Lys 110 | Ser | Glu |
| Thr | Ser | Ile 115 | Val | Cys | Ser | Lys | Phe 120 | Phe | Leu | Val | Asp | Glu 125 | Lys | Gly | Ser |
| Leu | Leu 130 | Thr | Lys | Lys | Glu | Ala 135 | Pro | Lys | Lys | Lys | Ser 140 | Glu | Val | Val | Ser |
| Ile 145 | Glu | Glu | Ser | Ile | Lys 150 | Ile | Leu | Leu | Leu | Gln 155 | Gln | Asn | Gly | Tyr | Asp 160 |
| Leu | Ala | Val | Trp | Gly 165 | Lys | Leu | Tyr | Pro | Val 170 | Ser | Phe | Phe | Glu 175 | Thr | Ile |
| Ser | Phe | Pro | Glu 180 | Gly | Lys | Leu | Tyr | Glu 185 | Asp | Met | Gly | Thr | Thr 190 | Tyr | Lys |
| Leu | Leu | Lys 195 | Leu | Ala | Ser | Glu | Val 200 | Val | Phe | Leu | Asp | Ala 205 | Tyr | Asp | Tyr |
| Ala | Tyr 210 | Val | Gln | Arg | Pro | Asn 215 | Ser | Ile | Met | Asn | Ser 220 | Ser | Phe | Asn | Leu |
| Lys 225 | Lys | Leu | Asp | Ile | Ile 230 | Glu | Met | Val | His | Glu 235 | Met | Glu | Asn | Asp | Ile 240 |
| Leu | Ala | Gln | Phe | Pro 245 | Asn | Leu | Ala | Leu | Tyr 250 | Val | Lys | Asn | Arg | Ala 255 | Phe |
| Ala | Ala | Glu | Val 260 | Lys | Ile | Phe | Leu | Glu 265 | Ile | Pro | Lys | Glu | Lys 270 | Glu | Phe |
| Glu | Gln | Ala | Gln 275 | Lys | Gln | Leu | Trp | His 280 | Asp | Ile | Lys | Lys | Asn 285 | Arg | Lys |

```
Ala Pro Phe Met Thr Lys Gly Ala Arg Leu Lys Asn Arg Leu Gly Ala
    290                 295                 300
Ser Leu Ser Phe Leu Gly Lys Ser Leu Phe Leu Thr Ile Gly Lys Gln
305                 310                 315                 320
Leu Val Asp Arg
```

( 2 ) INFORMATION FOR SEQ ID NO:11:

( i ) SEQUENCE CHARACTERISTICS:
        ( A ) LENGTH: 360 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Val Ile Tyr Phe Leu Leu Phe Pro Met Ile Ala Met Ile Tyr Leu
1               5                   10                  15
Met Thr Leu Leu Leu Arg Gln Lys Ala Gln Ile Gln Lys Thr Ile Phe
                20                  25                  30
Cys Val Leu Thr Phe Gly Thr Leu Gly Phe Ile Ser Ala Ser Arg Ala
            35                  40                  45
Ser Ser Val Gly Thr Asp Val Thr Leu Tyr Glu Asn Ile Phe Lys Ser
    50                  55                  60
Ile Asn Tyr Gly Ile Ser Ala Glu Asn Asn Trp Gly Tyr Val Ile Tyr
65                  70                  75                  80
Asn Lys Leu Ile Gly Ser Val Phe Gly Tyr Thr Gly His Glu Ile Thr
                85                  90                  95
Ala Ala Asn Ser Val Leu Ile Thr Ile Leu Ile Gly Ile Phe Ile Trp
            100                 105                 110
Lys Val Ala Glu His Tyr Phe Val Ala Thr Phe Leu Tyr Ile Ser Leu
        115                 120                 125
Phe Tyr Tyr Ala Thr Ser Phe Asn Ile Ser Arg Gln Phe Ile Ala Met
    130                 135                 140
Gly Leu Val Leu Val Ala Ile Ser Phe Ala Leu Asp Lys Lys Val Met
145                 150                 155                 160
Pro Trp Phe Ile Leu Thr Val Leu Ala Thr Leu Phe His Ala Thr Ala
                165                 170                 175
Ile Val Ala Phe Pro Val Tyr Trp Leu Thr Lys Val His Trp Asp Val
            180                 185                 190
Lys Lys Thr Leu Ser Ile Phe Pro Ile Thr Ile Phe Ala Ser Phe Ile
        195                 200                 205
Phe Asp Ala Ile Leu Asn Ile Phe Val Arg Phe Phe Pro His Tyr Glu
    210                 215                 220
Met Tyr Ile Thr Gly Thr Gln Phe Asn Ile Ser Asp Gln Gly Gln Gly
225                 230                 235                 240
Arg Val Val Leu Val Lys Ile Phe Ile Leu Leu Ile Leu Phe Thr Leu
                245                 250                 255
Phe Leu Phe Tyr Lys Lys Ser Tyr Ala Leu Ile Ser Glu Cys His Gln
            260                 265                 270
Ser Leu Ile Ala Leu Thr Thr Val Gly Leu Ser Ile Gly Ile Val Phe
        275                 280                 285
Tyr Asn Asn Ile Leu Leu Asn Arg Ile Glu Met Phe Tyr Ser Ile Leu
    290                 295                 300
Ser Ile Val Phe Ile Pro Ile Ala Ile Asp Tyr Ile Ser Leu Lys Phe
305                 310                 315                 320
```

| Lys | Gln | Lys | Asp | Ala | Val | Arg | Leu | Met | Leu | Thr | Ile | Gly | Ile | Leu | Leu |
|     |     |     |     | 325 |     |     |     |     | 330 |     |     |     |     | 335 |     |

| Ile | Thr | Leu | Val | Pro | Tyr | Tyr | Ile | Gln | Val | Ser | Gly | Asn | Tyr | Ser | Gly |
|     |     |     | 340 |     |     |     |     | 345 |     |     |     |     | 350 |     |     |

| Ile | Leu | Pro | Tyr | Val | Ile | Gln | Gln |
|     |     | 355 |     |     |     |     | 360 |

(2) INFORMATION FOR SEQ ID NO:12:

(i) SEQUENCE CHARACTERISTICS:
    (A) LENGTH: 316 amino acids
    (B) TYPE: amino acid
    (D) TOPOLOGY: linear (ii) MOLECULE TYPE: protein (xi) SEQUENCE DESCRIPTION: SEQ ID NO:12:

| Met | Glu | Asp | Arg | Lys | Lys | Gln | Val | Ile | Leu | Ile | Leu | Ser | His | Arg | Asn |
| 1   |     |     |     | 5   |     |     |     |     | 10  |     |     |     |     | 15  |     |

| Thr | Leu | Ala | Leu | Lys | Ser | Thr | Ile | Glu | Leu | Leu | Asp | Ser | Gln | Tyr | Phe |
|     |     |     | 20  |     |     |     |     | 25  |     |     |     |     | 30  |     |     |

| Asp | Phe | Phe | Leu | His | Ile | Asp | Lys | Lys | Ser | Arg | Ile | Gln | Asp | Phe | Phe |
|     |     | 35  |     |     |     |     | 40  |     |     |     |     | 45  |     |     |     |

| Tyr | Leu | Lys | Lys | Ile | Thr | Lys | Phe | Ser | Thr | Ile | His | Phe | Ser | Glu | Arg |
|     | 50  |     |     |     |     | 55  |     |     |     |     | 60  |     |     |     |     |

| Lys | Asn | Val | His | Trp | Gly | Gly | Phe | Ser | Met | Val | Glu | Ala | Met | Phe | Ala |
| 65  |     |     |     |     | 70  |     |     |     |     | 75  |     |     |     |     | 80  |

| Leu | Leu | Glu | Cys | Ala | Arg | Asp | Thr | Gly | Glu | Tyr | Ser | Tyr | Phe | His | Phe |
|     |     |     |     | 85  |     |     |     |     | 90  |     |     |     |     | 95  |     |

| Leu | Ser | Gly | Asp | Asp | Met | Pro | Ile | Lys | Asp | Asn | Glu | Ile | Val | Phe | Asn |
|     |     |     | 100 |     |     |     |     | 105 |     |     |     |     | 110 |     |     |

| Phe | Phe | Glu | Asn | Ser | Tyr | Pro | Lys | Asn | Phe | Ile | Asp | Ile | Leu | Asp | Phe |
|     |     | 115 |     |     |     |     | 120 |     |     |     |     | 125 |     |     |     |

| Glu | Asn | Val | Asn | Lys | Asn | Ser | Tyr | Phe | Tyr | Glu | Pro | Pro | Glu | Met | Ile |
|     | 130 |     |     |     |     | 135 |     |     |     |     | 140 |     |     |     |     |

| Glu | Glu | Arg | Val | Lys | Tyr | Tyr | Tyr | Pro | His | Met | Asp | Ile | Leu | Asn | Arg |
| 145 |     |     |     |     | 150 |     |     |     |     | 155 |     |     |     |     | 160 |

| Lys | Gly | Thr | Asn | Phe | Ile | Gly | Lys | Lys | Leu | Ile | Tyr | Leu | Gln | Lys | Leu |
|     |     |     |     | 165 |     |     |     |     | 170 |     |     |     |     | 175 |     |

| Leu | Lys | Val | Asn | Arg | Leu | Lys | Asn | Arg | Glu | Ile | Glu | Ile | Phe | Lys | Gly |
|     |     |     | 180 |     |     |     |     | 185 |     |     |     |     | 190 |     |     |

| His | Gln | Trp | Cys | Ser | Leu | Thr | Asn | Gln | Phe | Val | Asp | Ile | Leu | Leu | Asp |
|     |     | 195 |     |     |     |     | 200 |     |     |     |     | 205 |     |     |     |

| Lys | Glu | Glu | Arg | Arg | Val | Gly | Lys | Ser | Tyr | Phe | Ser | Ser | Ser | Leu | Ile |
|     | 210 |     |     |     |     | 215 |     |     |     |     | 220 |     |     |     |     |

| Pro | Asp | Glu | Cys | Tyr | Phe | Gln | Thr | Phe | Ala | Met | Ile | Lys | Lys | Val | Glu |
| 225 |     |     |     |     | 230 |     |     |     |     | 235 |     |     |     |     | 240 |

| Ile | Tyr | Gln | Gln | Lys | Asn | Met | Ser | Ala | Arg | Leu | Ile | Asp | Trp | Thr | Arg |
|     |     |     |     | 245 |     |     |     |     | 250 |     |     |     |     | 255 |     |

| Gly | Lys | Pro | Tyr | Ile | Trp | Arg | Gln | Asp | Asp | Phe | Phe | Glu | Ile | Met | Asn |
|     |     |     | 260 |     |     |     |     | 265 |     |     |     |     | 270 |     |     |

| Asp | Lys | Asp | Ser | Met | Phe | Ser | Arg | Lys | Phe | Asp | Glu | Asn | Val | Asp | Arg |
|     |     | 275 |     |     |     |     | 280 |     |     |     |     | 285 |     |     |     |

| Lys | Ile | Ile | Glu | Glu | Ile | Tyr | Ile | Lys | Ile | Arg | Gly | Arg | Ser | Thr | Asp |
|     | 290 |     |     |     |     | 295 |     |     |     |     | 300 |     |     |     |     |

| Glu | Ala | Asn | Lys | Ile | Lys | Asp | Lys | Arg | Phe | Thr | Lys |

(2) INFORMATION FOR SEQ ID NO:13:

(i) SEQUENCE CHARACTERISTICS:
        (A) LENGTH: 473 amino acids
        (B) TYPE: amino acid
        (D) TOPOLOGY: linear (ii) MOLECULE TYPE: protein (xi) SEQUENCE DESCRIPTION: SEQ ID NO:13:

```
Met Asn Lys Tyr Lys Lys Leu Leu Ser Asn Ser Leu Val Phe Thr Ile
 1               5                  10                  15

Gly Asn Leu Gly Ser Lys Leu Leu Val Phe Leu Leu Val Pro Leu Tyr
            20                  25                  30

Thr Tyr Ala Met Thr Pro Gln Glu Tyr Gly Met Ala Asp Leu Tyr Gln
        35                  40                  45

Thr Thr Ala Asn Leu Leu Leu Pro Leu Ile Thr Met Asn Val Phe Asp
    50                  55                  60

Ala Thr Leu Arg Phe Ala Met Glu Lys Ser Met Thr Lys Glu Ser Val
65                  70                  75                  80

Leu Thr Asn Ser Leu Val Val Trp Cys Phe Ser Ala Val Phe Thr Cys
                85                  90                  95

Leu Gly Ala Cys Ile Ile Tyr Ala Leu Asn Leu Ser Asn Lys Trp Tyr
            100                 105                 110

Leu Ala Leu Leu Leu Thr Phe Asn Leu Phe Gln Gly Gly Gln Ser Ile
            115                 120                 125

Leu Ser Gln Tyr Ala Arg Gly Ile Gly Lys Ser Lys Ile Phe Ala Ala
130                 135                 140

Gly Gly Val Ile Leu Thr Phe Leu Thr Gly Ala Leu Asn Ile Leu Phe
145                 150                 155                 160

Leu Val Tyr Leu Pro Leu Gly Ile Thr Gly Tyr Leu Met Ser Leu Val
                165                 170                 175

Leu Ala Asn Val Gly Thr Ile Leu Phe Phe Ala Gly Thr Leu Ser Ile
            180                 185                 190

Trp Lys Glu Ile Ser Phe Lys Ile Ile Asp Lys Lys Leu Ile Trp Gln
            195                 200                 205

Met Leu Tyr Tyr Ala Leu Pro Leu Ile Pro Ser Ser Ile Leu Trp Trp
    210                 215                 220

Leu Leu Asn Ala Ser Ser Arg Tyr Phe Val Leu Phe Phe Leu Gly Ala
225                 230                 235                 240

Gly Ala Asn Gly Leu Leu Ala Val Ala Thr Lys Ile Pro Ser Ile Ile
                245                 250                 255

Ser Ile Phe Asn Thr Ile Phe Thr Gln Ala Trp Gln Ile Ser Ala Ile
            260                 265                 270

Glu Glu Tyr Asp Ser His Gln Lys Ser Lys Tyr Tyr Ser Asp Val Phe
            275                 280                 285

His Tyr Leu Ala Thr Phe Leu Leu Leu Gly Thr Ser Ala Phe Met Ile
    290                 295                 300

Val Leu Lys Pro Ile Val Glu Lys Val Val Ser Ser Asp Tyr Ala Ser
305                 310                 315                 320

Ser Trp Gln Tyr Val Pro Phe Phe Met Leu Ser Met Leu Phe Ser Ser
                325                 330                 335

Phe Ser Asp Phe Phe Gly Thr Asn Tyr Ile Ala Ala Lys Gln Thr Lys
            340                 345                 350
```

```
Gly  Val  Phe  Met  Thr  Ser  Ile  Tyr  Gly  Thr  Ile  Val  Cys  Val  Leu  Leu
          355                      360                     365

Gln  Val  Val  Leu  Leu  Pro  Ile  Ile  Gly  Leu  Asp  Gly  Ala  Gly  Leu  Ser
370                           375                     380

Ala  Met  Leu  Gly  Phe  Leu  Thr  Thr  Phe  Leu  Leu  Arg  Val  Lys  Asp  Thr
385                      390                     395                      400

Gln  Lys  Phe  Val  Val  Ile  Gln  Ile  Lys  Trp  Arg  Ile  Phe  Ile  Ser  Asn
                    405                      410                     415

Leu  Leu  Ile  Val  Leu  Ala  Gln  Ile  Leu  Cys  Leu  Phe  Tyr  Leu  Pro  Ser
               420                      425                     430

Glu  Phe  Leu  Tyr  Phe  Gly  Leu  Ala  Leu  Leu  Phe  Cys  Gly  Met  Leu  Val
          435                      440                     445

Val  Asn  Gln  Arg  Thr  Ile  Leu  Tyr  Ile  Ile  Met  Ala  Leu  Lys  Ile  Lys
450                           455                     460

Asn  Lys  Thr  Phe  Gly  Met  Lys  Ser  Ser
465                      470
```

(2) INFORMATION FOR SEQ ID NO:14:

(i) SEQUENCE CHARACTERISTICS:
      (A) LENGTH: 307 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:14:

```
Met  Lys  Gln  Ile  Lys  Ser  Lys  Ile  Arg  Asp  Leu  Gln  Asn  Asn  Phe  Thr
1                   5                        10                      15

Tyr  Val  Phe  Gly  Lys  Lys  Thr  Phe  Leu  Gly  Arg  Gly  Glu  Ala  Ile  Ile
               20                       25                      30

Ile  Asp  Glu  Pro  Glu  His  Gly  Asn  Leu  Gly  Asp  Gln  Ala  Ile  Ala  Phe
          35                       40                      45

Ala  Glu  Asn  Gln  Phe  Leu  Val  Asn  His  Val  Ser  Val  Arg  Asp  Val  Glu
     50                       55                      60

His  Leu  Ile  Glu  Ser  Lys  Thr  Ile  Ser  Glu  Ile  Lys  Ser  Ile  Lys  Lys
65                       70                      75                       80

Asn  Ile  Gly  Lys  Lys  Glu  Leu  Val  Phe  Phe  His  Gly  Gly  Asn  Phe
                    85                       90                      95

Gly  Thr  Leu  Tyr  Leu  Lys  Tyr  Glu  Arg  Ile  Arg  Arg  Leu  Ala  Val  Ser
               100                      105                     110

Lys  Leu  Pro  Phe  Asn  Lys  Met  Ile  Leu  Phe  Pro  Gln  Ser  Ile  Ser  Phe
          115                      120                     125

Glu  Asp  Ser  Arg  Phe  Gly  Gln  Lys  Gln  Leu  Asn  Lys  Ser  Lys  Lys  Ile
     130                      135                     140

Tyr  Ser  Gln  Asn  Thr  Asn  Phe  Ile  Leu  Thr  Ala  Arg  Glu  Pro  Lys  Ser
145                      150                     155                      160

Tyr  Gly  Leu  Met  Lys  Lys  Cys  Phe  Pro  Tyr  Asn  Lys  Val  Ile  Leu  Thr
               165                      170                     175

Pro  Asp  Ile  Val  Leu  Ser  Phe  Lys  Phe  Glu  Val  Thr  Ile  Ser  Asp  Thr
          180                      185                     190

His  Ile  Gly  Lys  Glu  Lys  Asp  Ser  Val  Ile  Thr  Tyr  Glu  Asn  Arg  Gln
     195                      200                     205

His  Tyr  Leu  Glu  Ile  Lys  Trp  Asp  Glu  Ile  Ala  Gln  His  Glu  Val  Ala
     210                      215                     220

Leu  Thr  Asp  Arg  Leu  His  Gly  Met  Ile  Phe  Ser  Tyr  Ile  Thr  Gly  Thr
```

```
225                      230                      235                      240
Pro  Cys  Val  Val  Leu  Ala  Asn  Asn  His  Lys  Ile  Glu  Gly  Thr  Tyr
               245                      250                      255
Lys  His  Trp  Leu  Asn  Glu  Val  Asn  Tyr  Ile  Arg  Phe  Ile  Glu  Asn  Pro
               260                      265                      270
Thr  Val  Glu  Asn  Ile  Leu  Asp  Ala  Ile  Asn  Asp  Leu  Lys  Gln  Ile  Glu
          275                      280                      285
Pro  His  Tyr  Ile  Asp  Leu  Ser  Asp  Lys  Phe  Gln  Pro  Leu  Ile  Asp  Ala
     290                      295                      300
Ile  Lys  Gly
305
```

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonuceotide"

( x i ) SEQUENCE DESCRIPTION: SEQ ID NO:15:

GTTGCGGCCG CGATAAAGTG TGATAAGTCC AG                                32

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:16:

ATAGCGGCCG CTTAGCTCAT GTTGATGCGG                                   30

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:17:

CCTGCGGCCG CGCTTCCTAA TTCTGTAATC G                                 31

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:18:

CTGGCGGCCG CTACTTCACG TTTCTTTGCA T                                 31

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:19:

TACGCGGCCG CACATAGAAT AAGGCTTTAC G        3 1